United States Patent
Takashino

(10) Patent No.: US 9,907,605 B2
(45) Date of Patent: *Mar. 6, 2018

(54) MEDICAL TREATMENT DEVICE, MEDICAL TREATMENT SYSTEM, AND MEDICAL TREATMENT METHOD

(75) Inventor: Tomoyuki Takashino, Fuchu (JP)

(73) Assignee: OLYMPUS CORPORATION (JP)

( * ) Notice: Subject to any disclaimer, the term of this patent is extended or adjusted under 35 U.S.C. 154(b) by 43 days.

This patent is subject to a terminal disclaimer.

(21) Appl. No.: 13/366,448

(22) Filed: Feb. 6, 2012

(65) Prior Publication Data

US 2012/0136345 A1  May 31, 2012

Related U.S. Application Data

(63) Continuation of application No. PCT/JP2009/064193, filed on Aug. 11, 2009.

(51) Int. Cl.
  *A61B 18/14* (2006.01)
  *A61B 18/18* (2006.01)
  *A61B 18/00* (2006.01)

(52) U.S. Cl.
  CPC ...... *A61B 18/1445* (2013.01); *A61B 18/1815* (2013.01); *A61B 2018/0063* (2013.01); *A61B 2018/00345* (2013.01); *A61B 2018/00404* (2013.01); *A61B 2018/00619* (2013.01); *A61B 2018/1412* (2013.01); *A61B 2018/1455* (2013.01)

(58) Field of Classification Search
  USPC ..................... 606/8, 37–40, 49–52
  See application file for complete search history.

(56) References Cited

U.S. PATENT DOCUMENTS

| 6,626,901 B1* | 9/2003 | Treat et al. ............ 606/29 |
| 7,238,195 B2* | 7/2007 | Viola ............ 606/219 |
| 2002/0062123 A1* | 5/2002 | McClurken ............ A61B 18/14 606/34 |

(Continued)

FOREIGN PATENT DOCUMENTS

| EP | 2 465 458 | 6/2012 |
| EP | 2 491 880 | 8/2012 |

(Continued)

OTHER PUBLICATIONS

International Search Report dated Nov. 17, 2009 in corresponding PCT International Application No. PCT/JP2009/064193, along with English translation thereof.
Written Opinion dated Nov. 17, 2009 in corresponding PCT International Application No. PCT/JP2009/064193.

(Continued)

*Primary Examiner* — Lynsey Eiseman
(74) *Attorney, Agent, or Firm* — Ostrolenk Faber LLP

(57) ABSTRACT

A medical treatment device to treat and join body tissues, includes at least a pair of holding members which is configured to hold the body tissues to be treated, an energy output portion provided on at least one of the pair of holding members and connected to an energy source to form a joined portion by supplying energy to the body tissues held by the pair of holding members to join the body tissues, and a join condition maintenance assistance portion capable of applying a substance which prevents infiltration of the fluid to the body tissues to be treated to provide assistance so that a joined state of the body tissues is maintained.

12 Claims, 62 Drawing Sheets

(56) References Cited

U.S. PATENT DOCUMENTS

| | | | |
|---|---|---|---|
| 2003/0195513 A1* | 10/2003 | Truckai et al. | 606/51 |
| 2003/0236518 A1* | 12/2003 | Marchitto et al. | 606/27 |
| 2006/0009802 A1 | 1/2006 | Modesitt | |
| 2007/0066969 A1* | 3/2007 | McGreevy et al. | 606/32 |
| 2008/0195091 A1* | 8/2008 | Takashino | A61B 18/1445 606/41 |
| 2008/0230583 A1* | 9/2008 | Heinrich | 227/176.1 |
| 2008/0294222 A1* | 11/2008 | Schechter | 607/50 |

FOREIGN PATENT DOCUMENTS

| | | |
|---|---|---|
| JP | 7-023970 | 1/1995 |
| JP | 10-191902 | 7/1998 |
| JP | 2001-514541 | 9/2001 |
| JP | 2001-327520 | 11/2001 |
| JP | 2004-525718 | 8/2004 |
| JP | 2008-505697 | 2/2008 |
| WO | WO 01/12090 | 2/2001 |
| WO | WO 02/085218 | 10/2002 |
| WO | WO 03/094743 | 11/2003 |
| WO | WO 2006/080523 | 8/2006 |

OTHER PUBLICATIONS

Office Action issued by the Japanese Patent Office dated Mar. 21, 2012 in connection with corresponding Japanese Patent Application No. 2011-526660.

Translation of Office Action issued by the Japanese Patent Office dated Mar. 21, 2012 in connection with corresponding Japanese Patent Application No. 2011-526660.

Office Action issued by the Chinese Patent Office dated Feb. 11, 2014 in connection with corresponding Chinese Patent Application No. 2009-80161891.6.

Translation of Office Action issued by the Chinese Patent Office dated Feb. 11, 2014 in connection with corresponding Japanese Patent Application No. 2009-80161891.6.

English translation of the International Preliminary Report on Patentability for corresponding International Application No. PCT/JP2009/064193 dated Mar. 22, 2012.

Search Report issued by European Patent Office dated Apr. 22, 2014 in connection with corresponding EP patent application No. 09 84 8263.

Office Action issued by Chinese Patent Office dated Sep. 30, 2014 in connection with corresponding Chinese Patent Application No. 200980161891.6 with English Translation thereof.

Jun. 29, 2016 Office Action in corresponding application filed in China, with English translation.

* cited by examiner

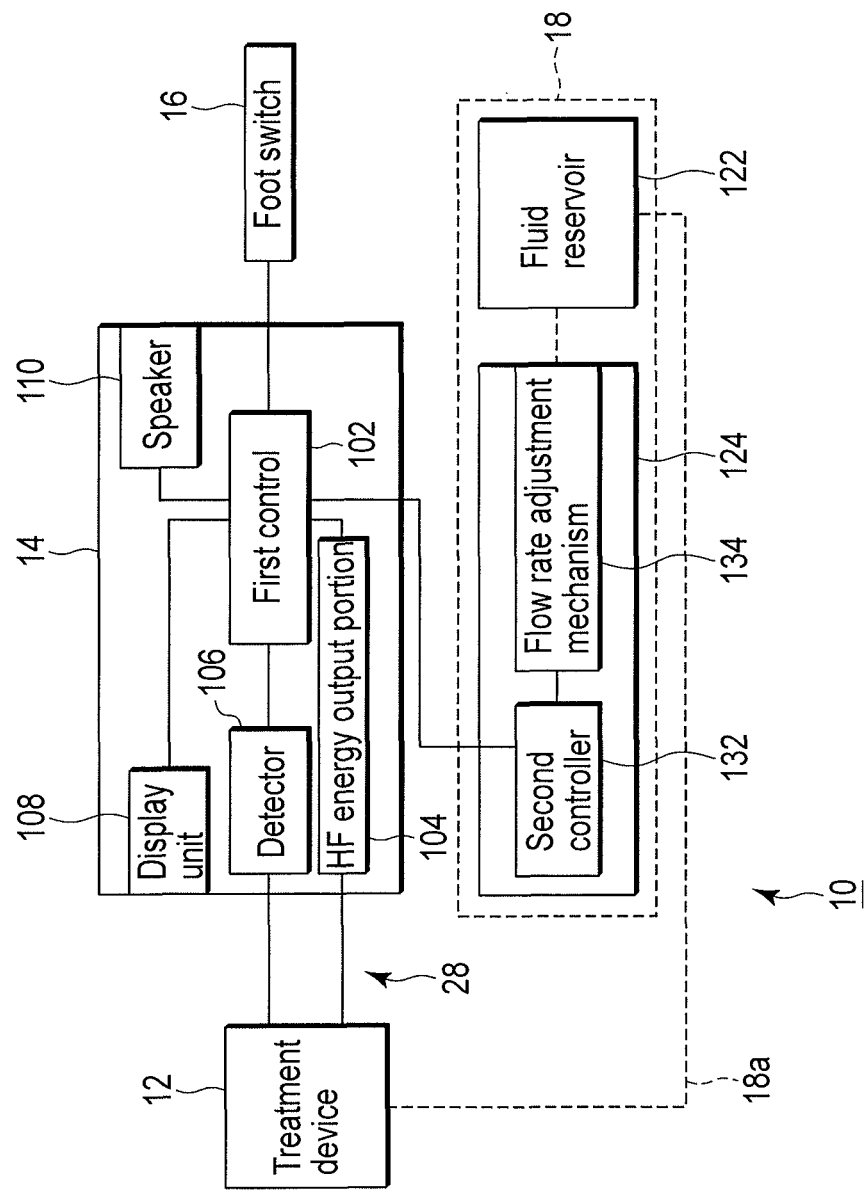
F I G. 2

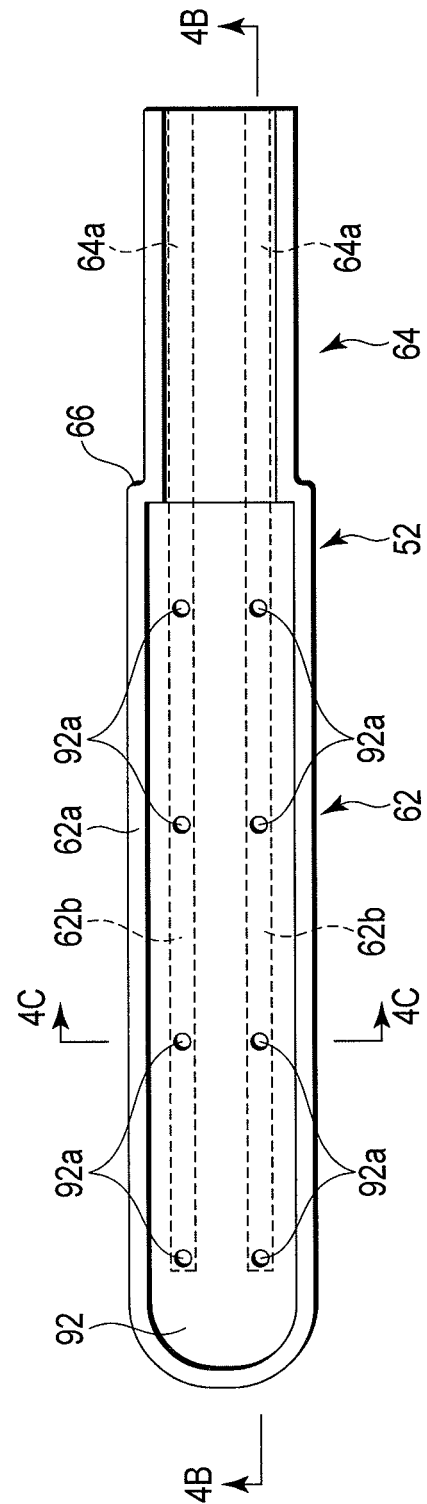
F I G. 4A

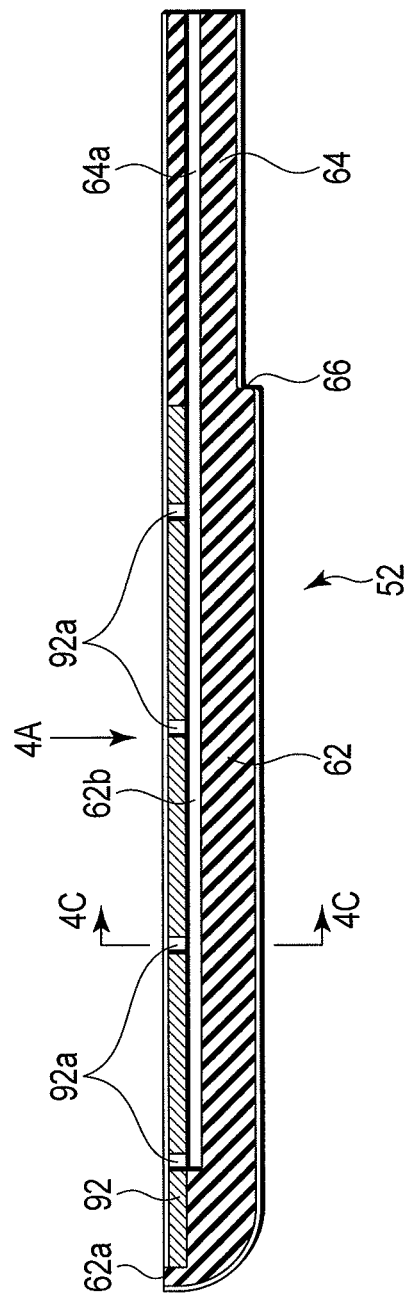
F I G. 4 B

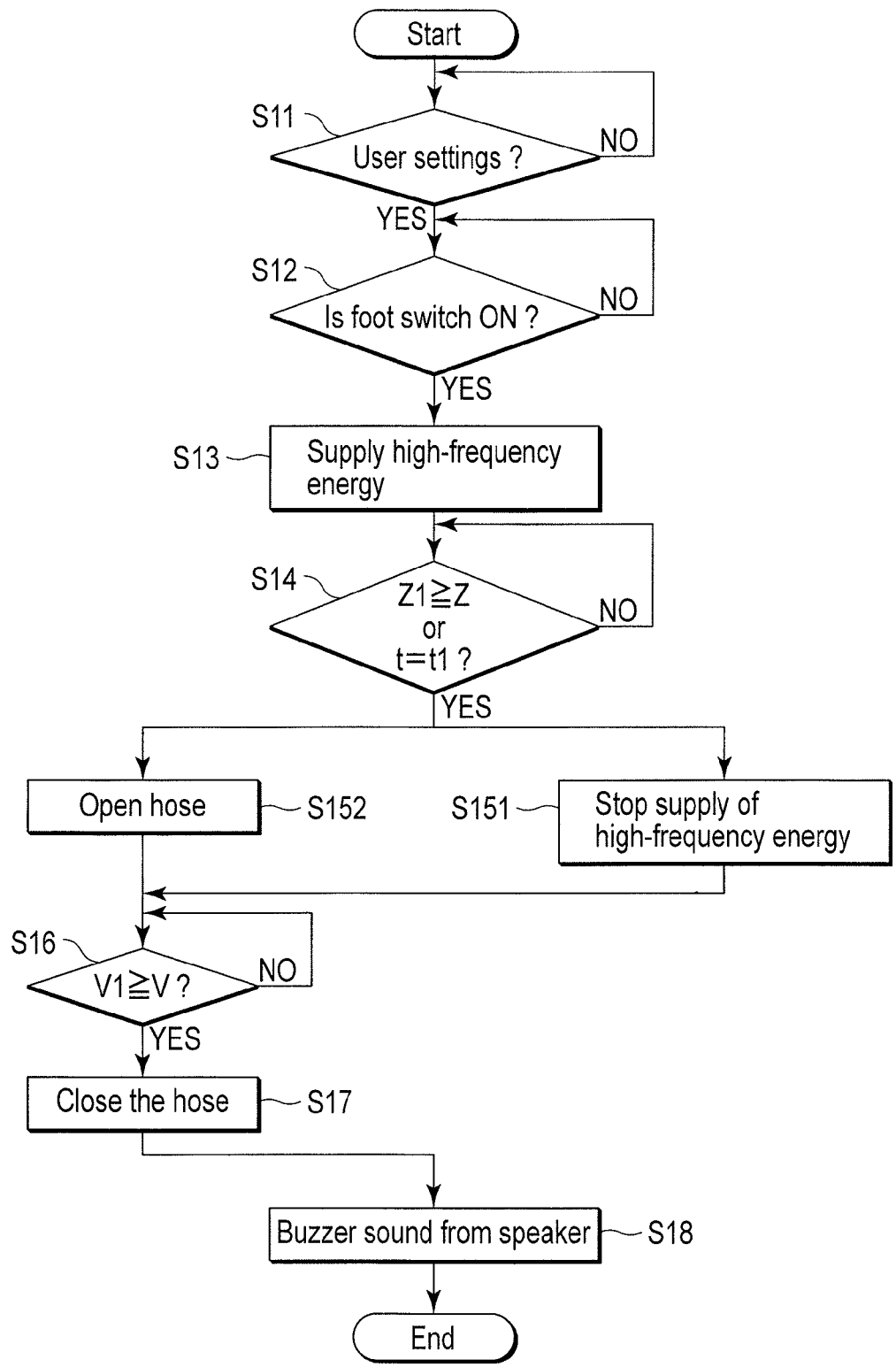
F I G. 6

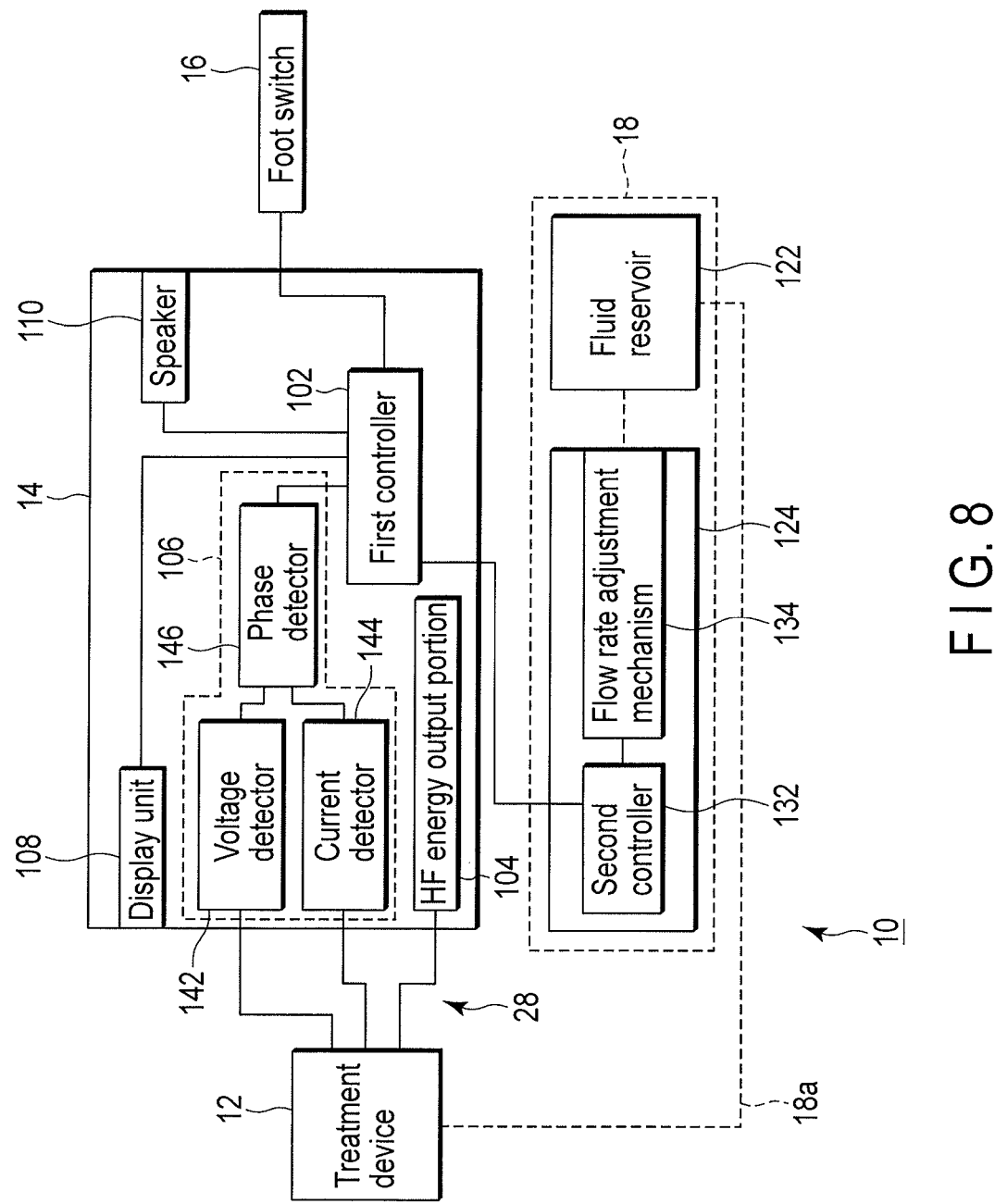
F I G. 8

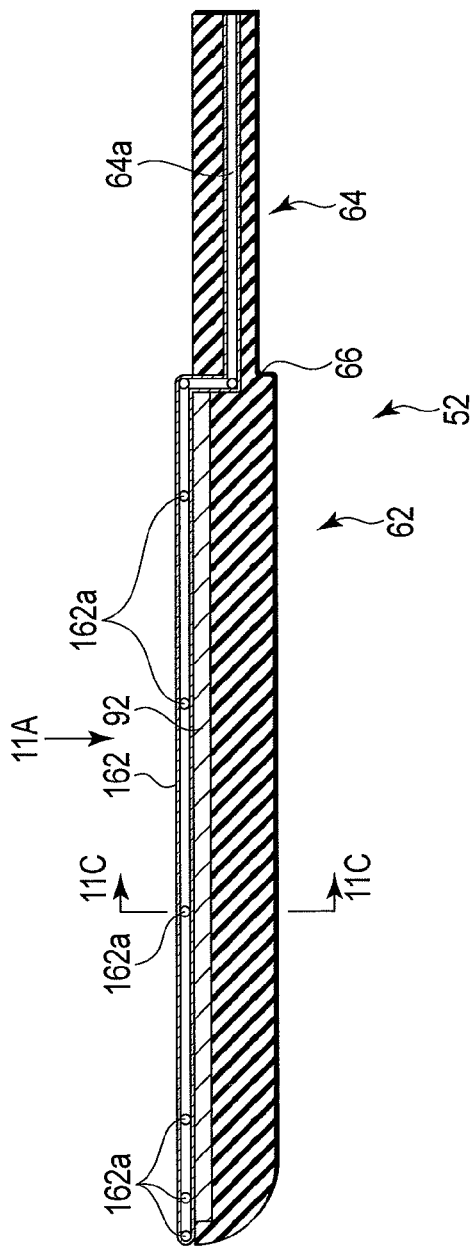
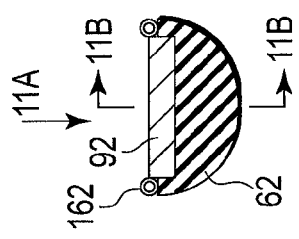
FIG. 11B
FIG. 11C

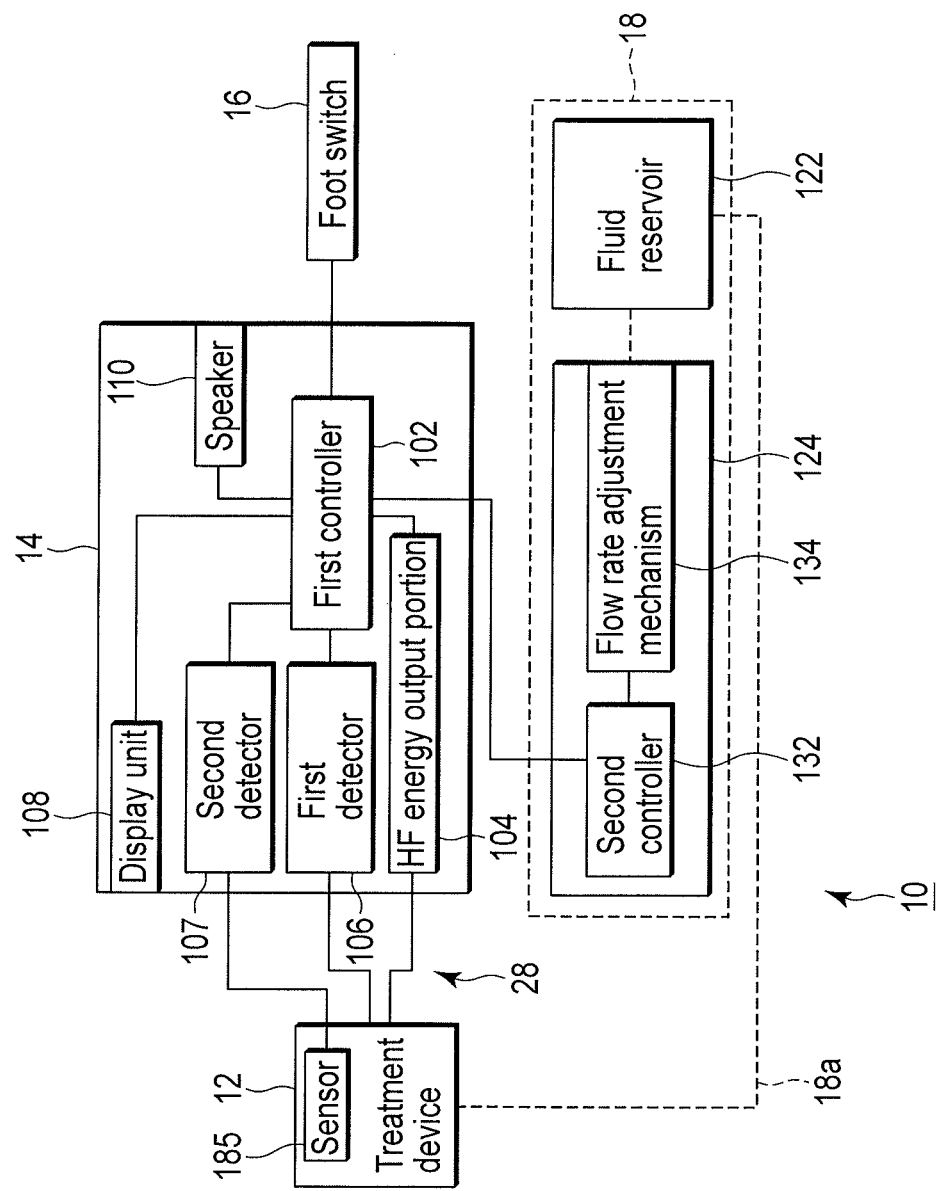
F I G. 13

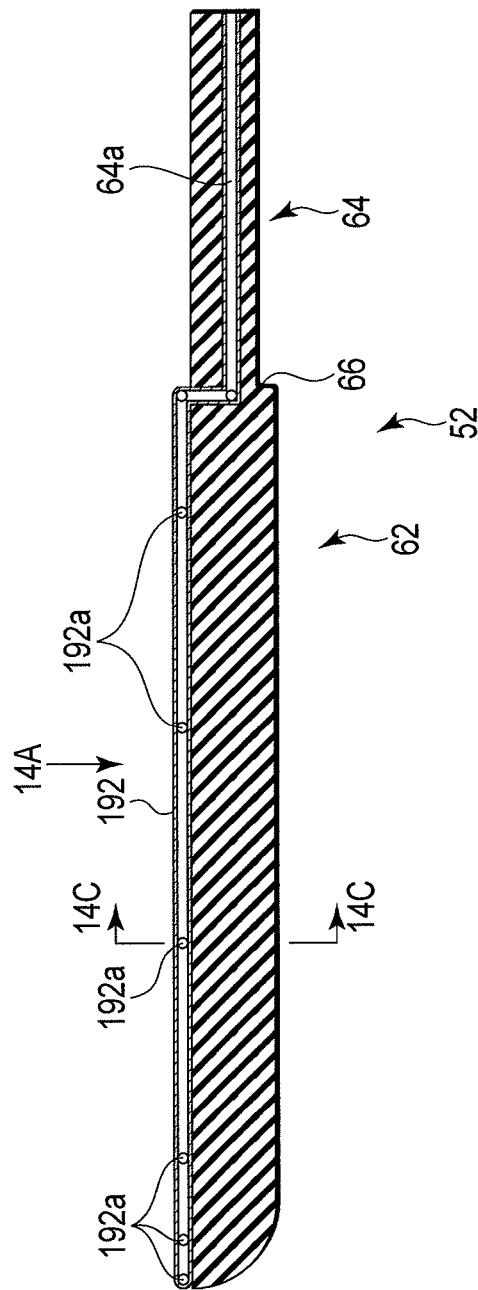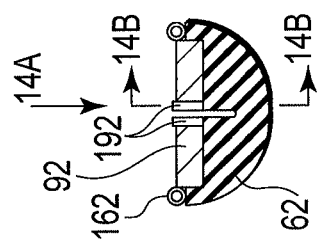
FIG. 14B
FIG. 14C

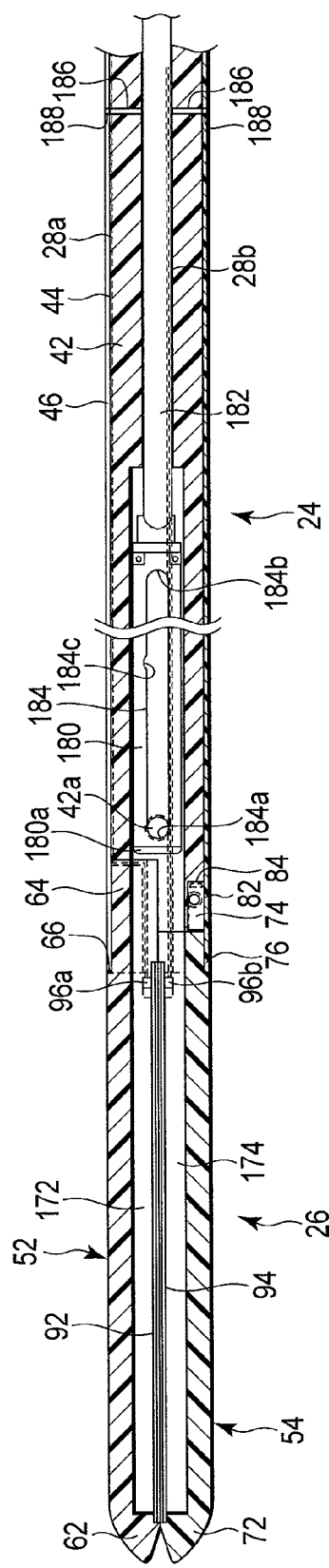
F I G. 15A

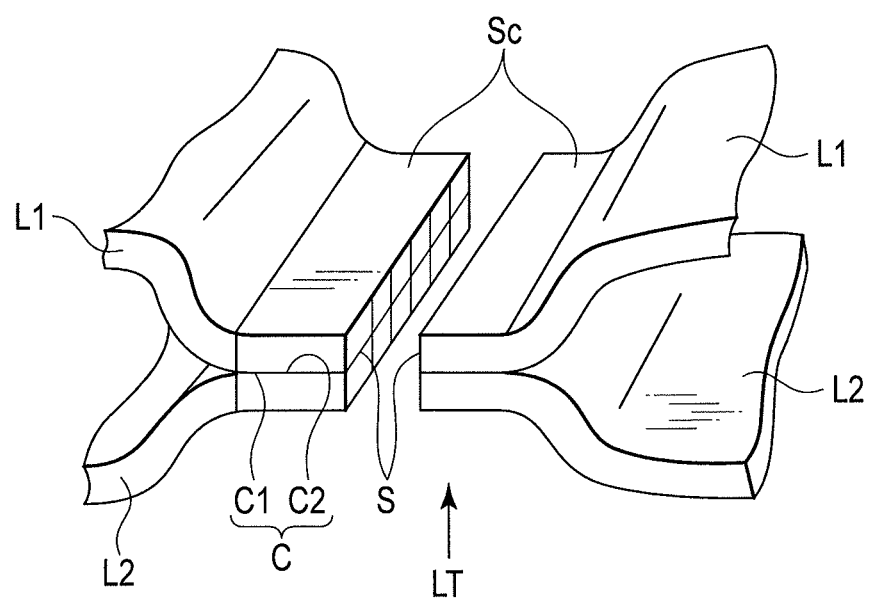
F I G. 17

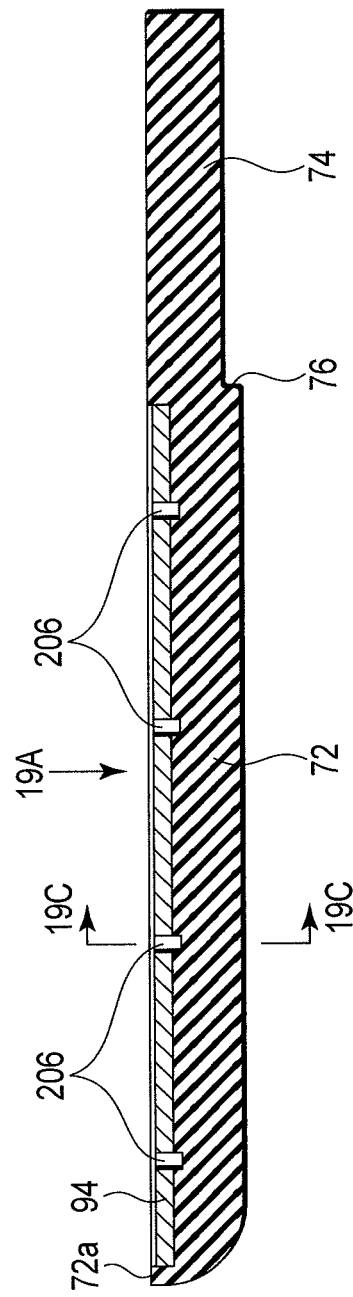
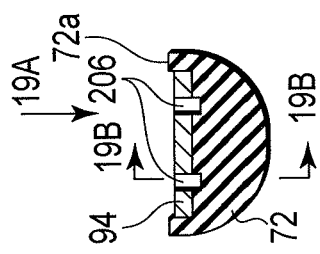
FIG. 19B
FIG. 19C

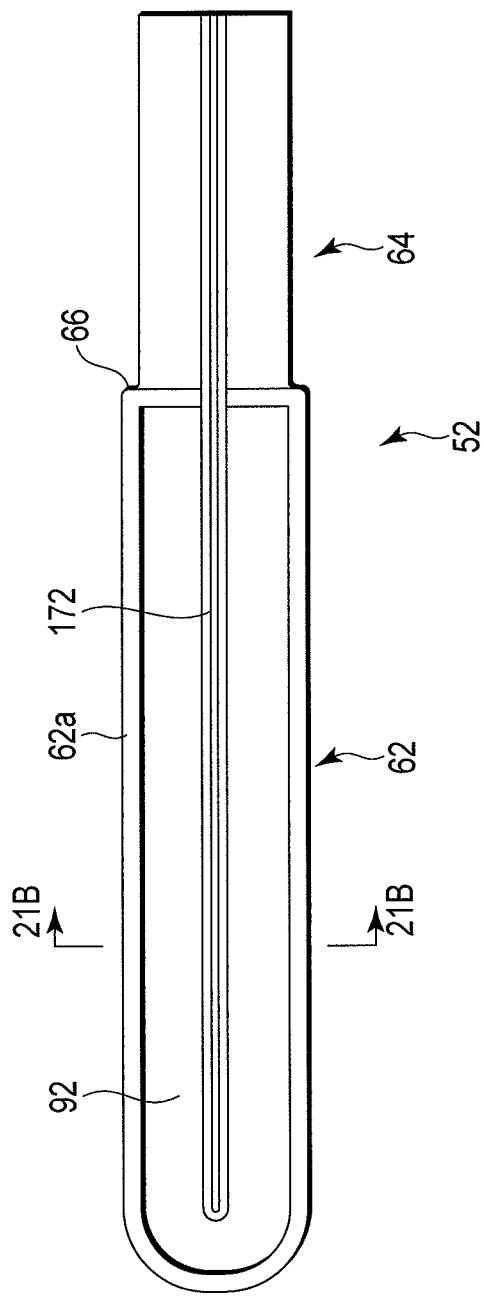
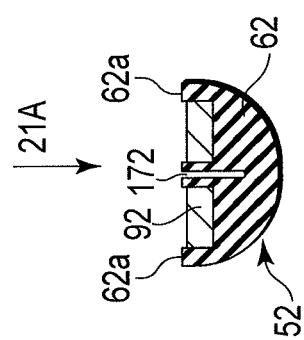
FIG. 21A
FIG. 21B

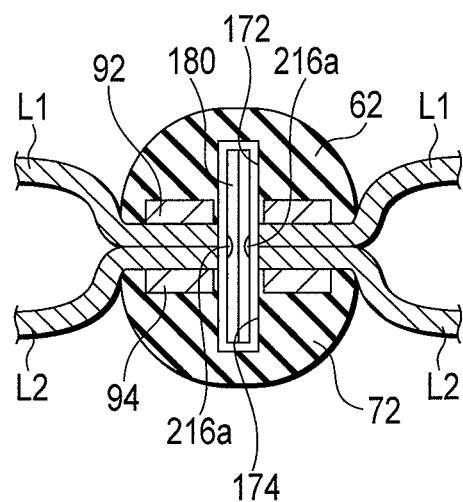
F I G. 24 C
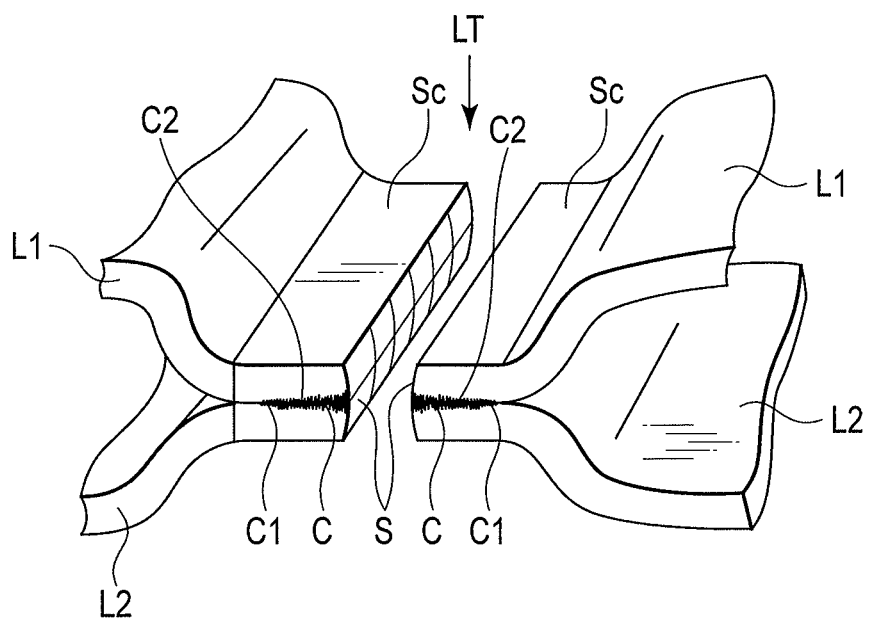
F I G. 24 D

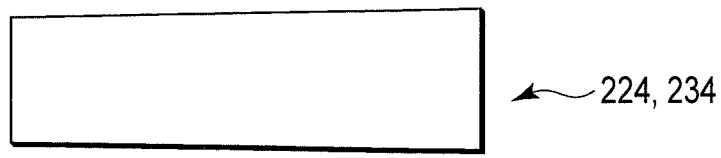
F I G. 2 8 A
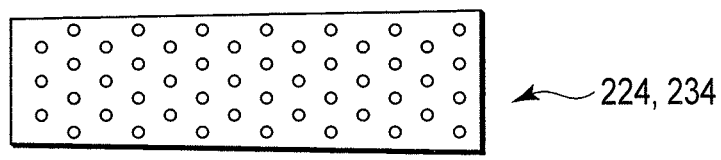
F I G. 2 8 B
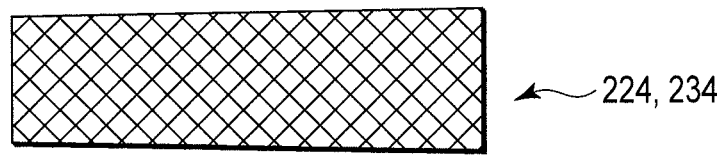
F I G. 2 8 C

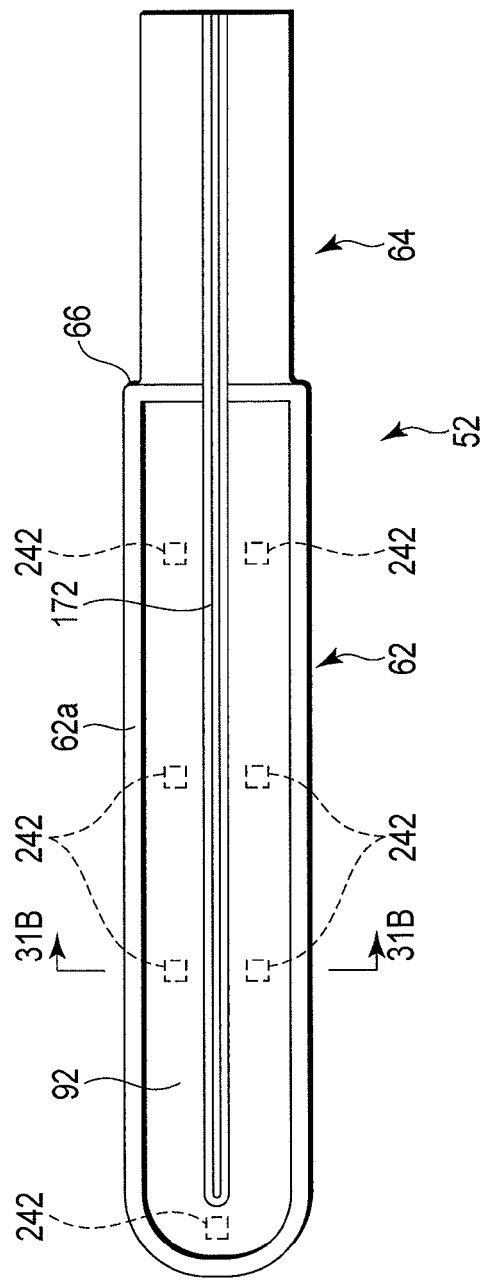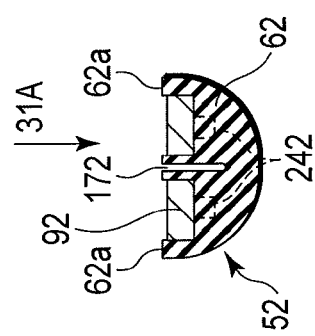
FIG. 31A
FIG. 31B

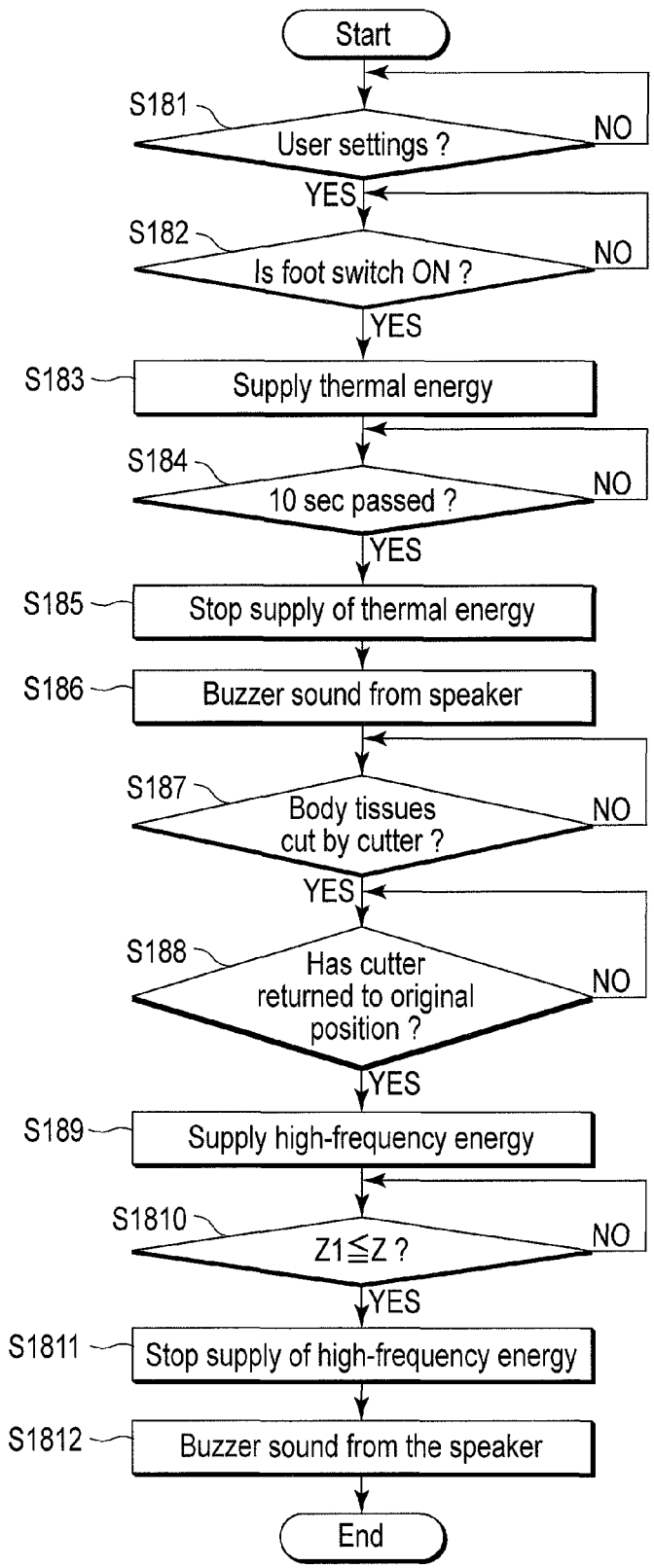
F I G. 32

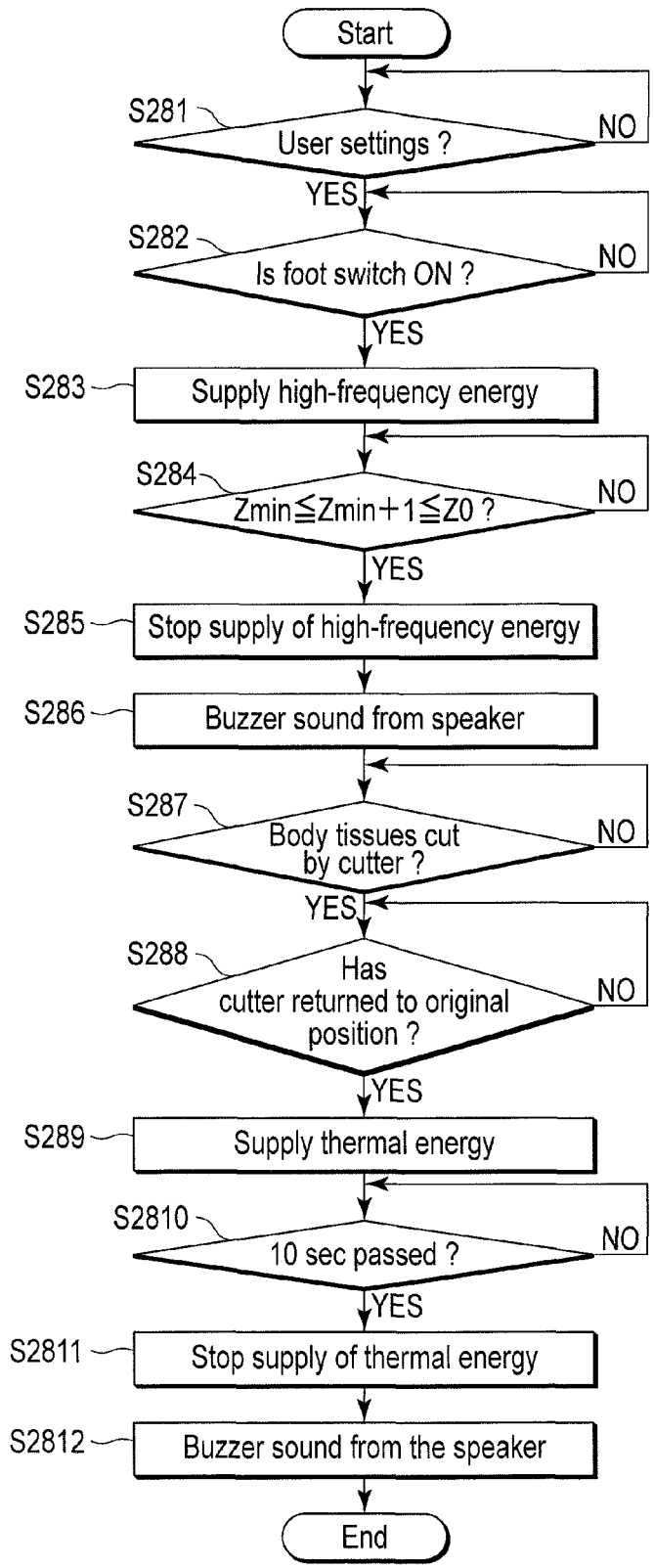
F I G. 34

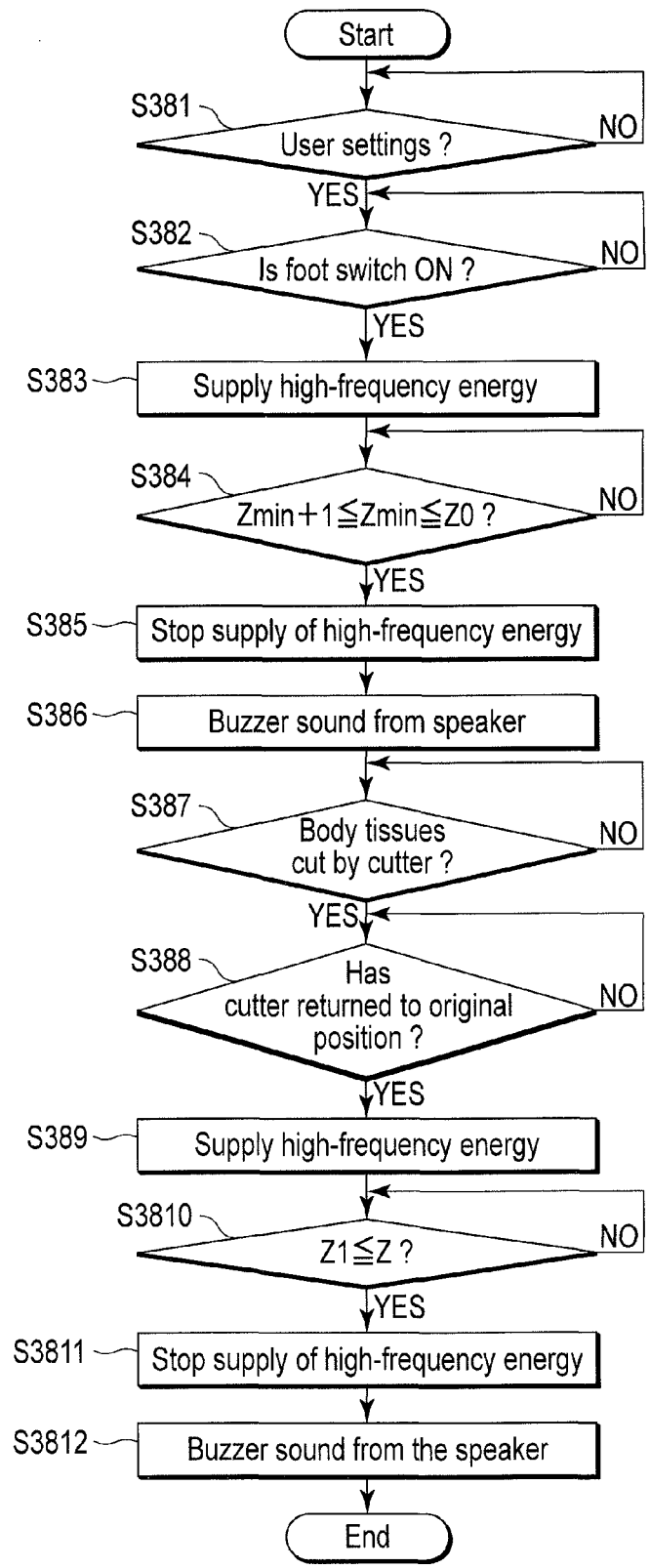
F I G. 3 5

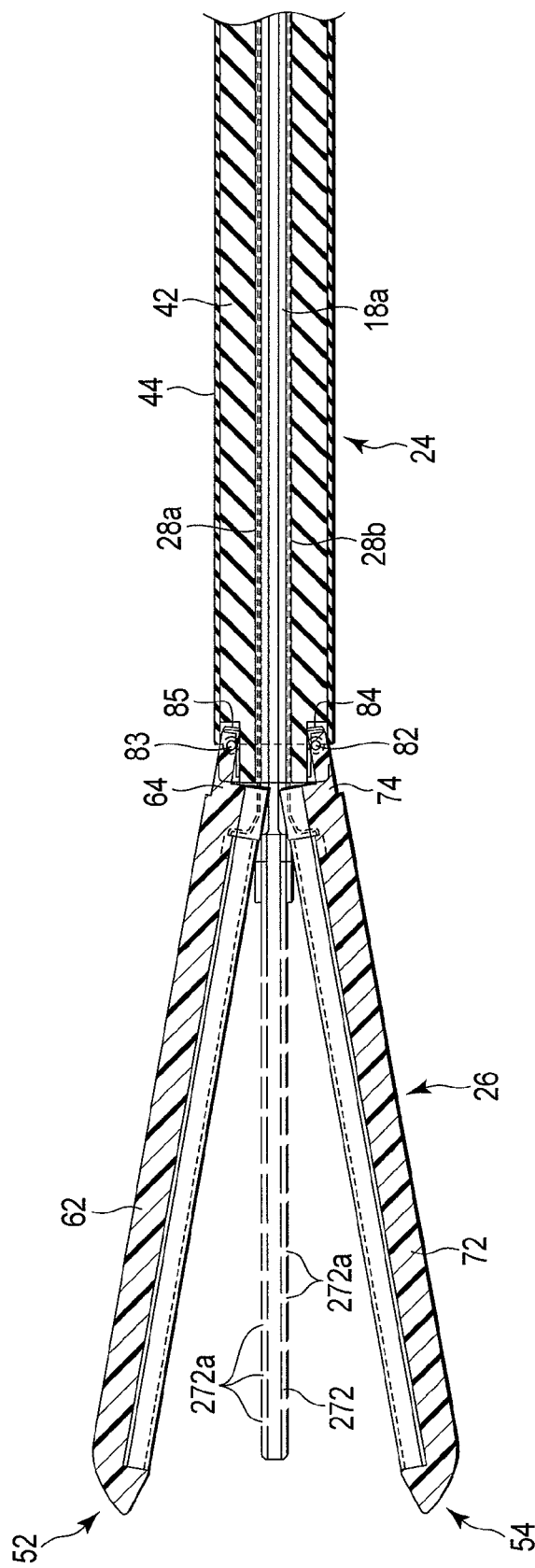
F I G. 39 B

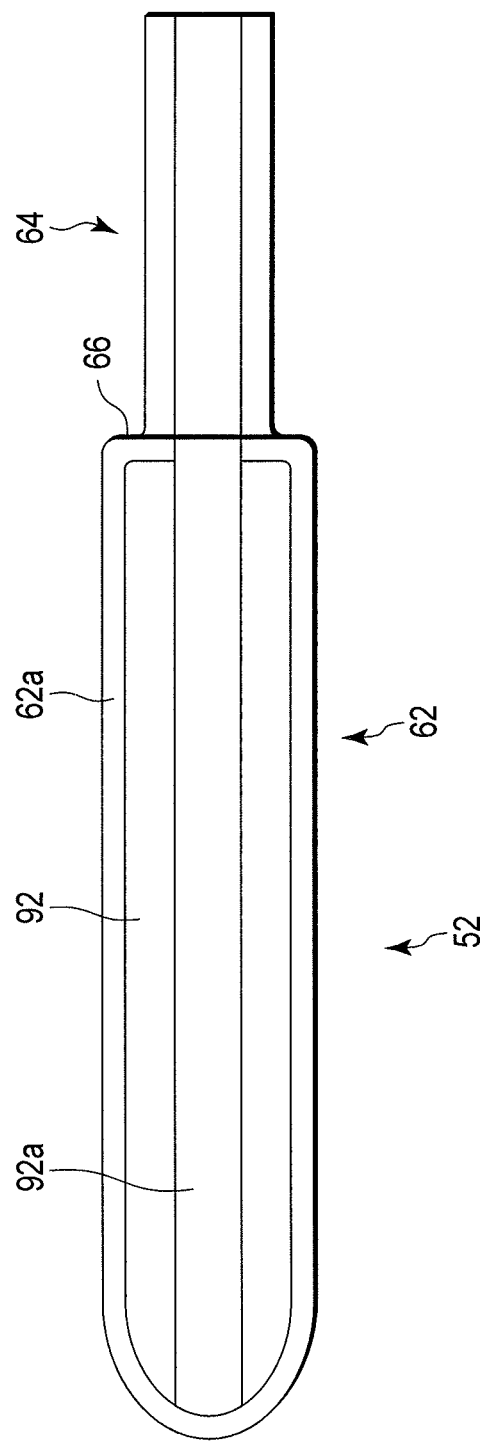
F I G. 40A

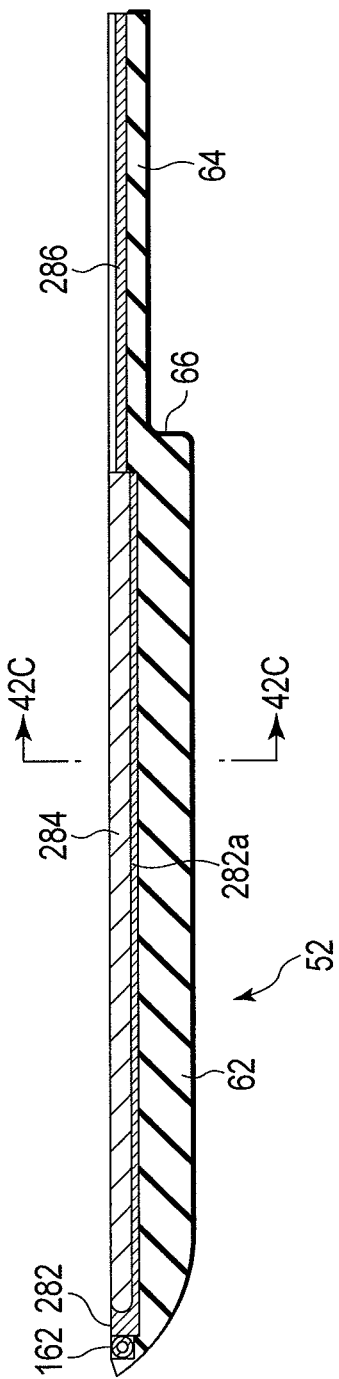
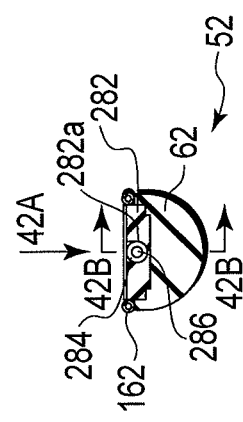
FIG. 42B
FIG. 42C

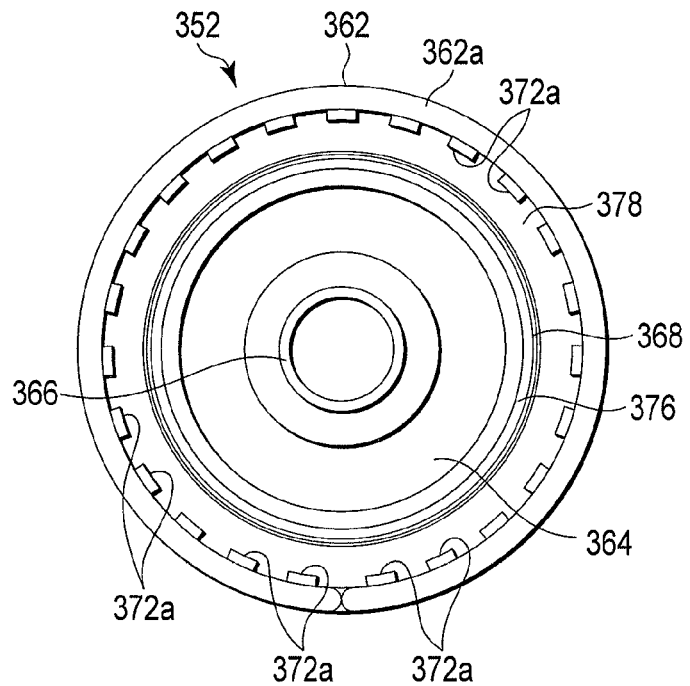
F I G. 4 5
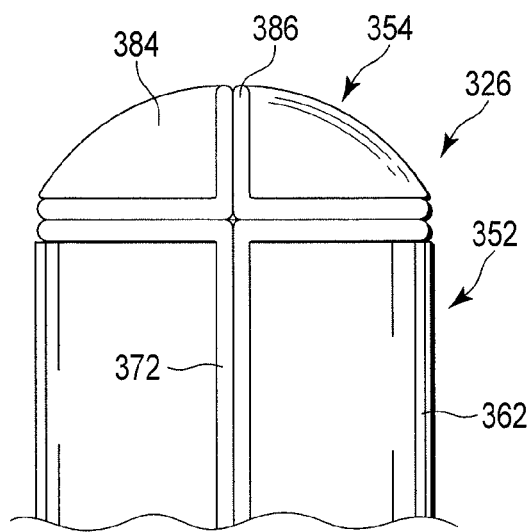
F I G. 4 6 A

MEDICAL TREATMENT DEVICE, MEDICAL TREATMENT SYSTEM, AND MEDICAL TREATMENT METHOD

CROSS REFERENCE TO RELATED APPLICATIONS

This application is a Continuation Application of PCT Application No. PCT/JP2009/064193, filed Aug. 11, 2009, the entire contents of which are incorporated herein by reference.

BACKGROUND OF THE INVENTION

1. Field of the Invention

The present invention relates to a medical treatment device, a medical treatment system, and a medical treatment method to cure/treat body tissues.

2. Description of the Related Art

It is generally known that body tissues can be joined by (1) bringing body tissues to be joined into contact, (2) denaturing proteins of target tissues, and (3) removing fluid present between target tissues. This is join using a so-called hydrogen bond, which is a linkage using polarity of a polar group of amino acids constituting proteins. Such a description can be found in, for example, U.S. Pat. No. 6,626,901.

Note that denaturing proteins denotes inducing a conformational change, which is one of features of proteins, that is, dissociating the linkage of polar groups linked with certain regularity to form the conformational structure of proteins. It becomes possible to promote a new linkage with a polar group present in adjacent proteins by using the polar group freed by dissociating the linkage of polar groups and so a linkage of proteins and accordingly, conjugation of body tissues can be induced.

To induce the phenomenon, various forms of energy such as high frequencies, heat, ultrasonic, and laser light are used by medical treatment devices. By using such forms of energy, the temperature of joining target tissues is raised to denature proteins and to remove moisture ($H_2O$) present between target tissues simultaneously. Conjugation of tissues is thereby achieved. Energy devices currently used as blood vessel sealing devices use this phenomenon.

An effect brought about by removing fluid ($H_2O$) will be described. It is generally known that a water molecule $H_2O$ has a strong polarity. Due to the strong polarity, the water molecule is known to be easily linked to a polar group having a polarity. The linkage is also established between water molecules $H_2O$, thereby inducing a phenomenon specific to water molecules $H_2O$. For example, while the heat of vaporization of helium is 0.0845 kJ/mol, the heat of vaporization of the water molecule $H_2O$ is a high value of 40.8 kJ/mol (9.74666 kcal/mol). It is a known fact that such a high value is a result of the hydrogen bonding acting between water molecules $H_2O$. As described above, the water molecule $H_2O$ is easily linked to a molecule having a polar group due to the strong polarity. That is, the water molecule $H_2O$ is also easily linked to proteins having a polar group. This fact makes conjugation of tissues difficult in the presence of water molecules $H_2O$.

BRIEF SUMMARY OF THE INVENTION

In an aspect of the present invention, there is provided a medical treatment device to treat and conjugate body tissues, includes at least a pair of holding members which is configured to hold the body tissues to be treated, an energy output portion provided in at least one of the pair of holding members and connected to an energy source to form a joined portion by supplying energy to the body tissues held by the pair of holding members to join the body tissues, and a conjugation maintenance assistance portion capable of applying a substance which prevents infiltration of the fluid to the body tissues to be treated to provide assistance so that a joined state of the body tissues is maintained.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic block diagram showing the medical treatment system according to the first embodiment.

FIG. 4A is a schematic plan view viewed from an arrow 4A direction in FIGS. 4B and 4C, and shows a first holding member of the treatment portion of the energy treatment device of the medical treatment system according to the first embodiment.

FIG. 4B is a schematic longitudinal sectional view along a 4B-4B line in FIGS. 4A and 4C, and shows the first holding member of the treatment portion of the energy treatment device of the medical treatment system according to the first embodiment.

FIG. 6 is a flow chart showing a state of control of the medical treatment system exercised by an energy source, a foot switch, and a fluid source when body tissues are joined and an outer circumference of the joined body tissue is coated by using the medical treatment system according to the first embodiment.

FIG. 8 is a schematic block diagram showing the medical treatment system when a change of the phase difference is used as a threshold of supplying the high-frequency energy/stopping the supply of the high-frequency energy for treatment according to the modification of the first embodiment.

FIG. 11B is a schematic longitudinal sectional view along a 11B-11B line in FIGS. 11A and 11C, and shows the first holding member of the treatment portion of the energy treatment device of the medical treatment system according to the second embodiment.

FIG. 11C is a schematic transverse sectional view along a 11C-11C line in FIGS. 11A and 11B, and shows the first holding member of the treatment portion of the energy treatment device of the medical treatment system according to the second embodiment.

FIG. 13 is a schematic block diagram showing the medical treatment system according to the third embodiment.

FIG. 14B is a rough longitudinal sectional view along a 14B-14B line in FIGS. 14A and 14C, and shows the first holding member of the treatment portion of the energy treatment device of the medical treatment system according to the third embodiment.

FIG. 14C is a schematic transverse sectional view along a 14C-14C line in FIGS. 14A and 14B, and shows the first holding member of the treatment portion of the energy treatment device of the medical treatment system according to the third embodiment.

FIG. 15A is a schematic longitudinal sectional view showing the closed treatment portion and a shaft of a bipolar type energy treatment device of the medical treatment system according to the third embodiment.

FIG. 17 is a rough perspective view showing the state of body tissues immediately after being treated by using the energy treatment device of the medical treatment system according to the third embodiment.

FIG. 19B is a rough longitudinal sectional view along a 19B-19B line in FIGS. 19A and 19C, and shows the second holding member of the treatment portion of the energy treatment device of the medical treatment system according to the fourth embodiment.

FIG. 19C is a rough transverse sectional view along a 19C-19C line in FIGS. 19A and 19B, and shows the second holding member of the treatment portion of the energy treatment device of the medical treatment system according to the fourth embodiment.

FIG. 21A is a rough plan view viewed from an arrow 21A direction in FIG. 21B, and shows a first holding member of a treatment portion of an energy treatment device of a medical treatment system according to a fifth embodiment.

FIG. 21B is a rough transverse sectional view along a 21B-21B line in FIG. 21A, and shows the first holding member of the treatment portion of the energy treatment device of the medical treatment system according to the fifth embodiment.

FIG. 24C is a rough transverse sectional view showing the state of treating and conjugating body tissues while being held by the treatment portion of the energy treatment device of the medical treatment system and being cut by the cutter according to the sixth embodiment.

FIG. 24D is a rough perspective view showing the state of body tissues immediately after being treated by using the energy treatment device of the medical treatment system according to the sixth embodiment.

FIG. 28A is a rough perspective view showing a sheet-shaped coating member disposed on the main body of the first and second holding members of the treatment portion of the energy treatment device of the medical treatment system according to the seventh embodiment.

FIG. 28B is a rough perspective view showing a porous coating member disposed on the main body of the first and second holding members of the treatment portion of the energy treatment device of the medical treatment system according to the seventh embodiment.

FIG. 28C is a rough perspective view showing a mesh-shaped coating member disposed on the main body of the first and second holding members of the treatment portion of the energy treatment device of the medical treatment system according to the seventh embodiment.

FIG. 31A is a rough plan view viewed from an arrow 31A direction in FIG. 31B, and shows a first holding member of a treatment portion of an energy treatment device of a medical treatment system according to an eighth embodiment.

FIG. 31B is a rough transverse sectional view along a 31B-31B line in FIG. 31A, and shows the first holding member of the treatment portion of the energy treatment device of the medical treatment system according to the eighth embodiment.

FIG. 32 is a flow chart showing the state of control of the medical treatment system exercised by an energy source, a foot switch, and a fluid source when body tissues are treated by using the medical treatment system according to the eighth embodiment.

FIG. 34 is a flow chart showing the state of control of the medical treatment system exercised by the energy source, the foot switch, and the fluid source when body tissues are treated by using the medical treatment system according to the eighth embodiment.

FIG. 35 is a flow chart showing the state of control of the medical treatment system exercised by the energy source, the foot switch, and the fluid source when body tissues are treated by using the medical treatment system according to the eighth embodiment.

FIG. 39B is a rough longitudinal sectional view showing the open treatment portion and the shaft of the energy treatment device of the medical treatment system according to the tenth embodiment.

FIG. 40A is a rough plan view showing a first holding member of the treatment portion of the energy treatment device of the medical treatment system according to the tenth embodiment.

FIG. 42B is a rough longitudinal sectional view along a 42B-42B line in FIGS. 42A and 42C, and shows the first holding member of the treatment portion of the energy treatment device of the medical treatment system according to the eleventh embodiment.

FIG. 42C is a rough transverse sectional view along a 42C-42C line in FIGS. 42A and 42B, and shows the first holding member of the treatment portion of the energy treatment device of the medical treatment system according to the eleventh embodiment.

FIG. 45 is a rough plan view viewed from an arrow 45 direction in FIG. 44A, and shows the main body-side holding member of the treatment portion of the energy treatment device of the medical treatment system according to the twelfth embodiment.

FIG. 46A is a rough front view showing the state in which the main body-side holding member and the detachable-side holding member of the treatment portion of the bipolar type energy treatment device of the medical treatment system are closed according to the twelfth embodiment.

DETAILED DESCRIPTION OF THE INVENTION

The best mode for carrying out the present invention will be described below with reference to drawings.

First Embodiment

The first embodiment will be described with reference to FIGS. 1 to 6.

For example, a linear-type surgical treatment device 12 for treatment through the abdominal wall is taken as an example of the energy treatment device (medical treatment device).

Figure 1:
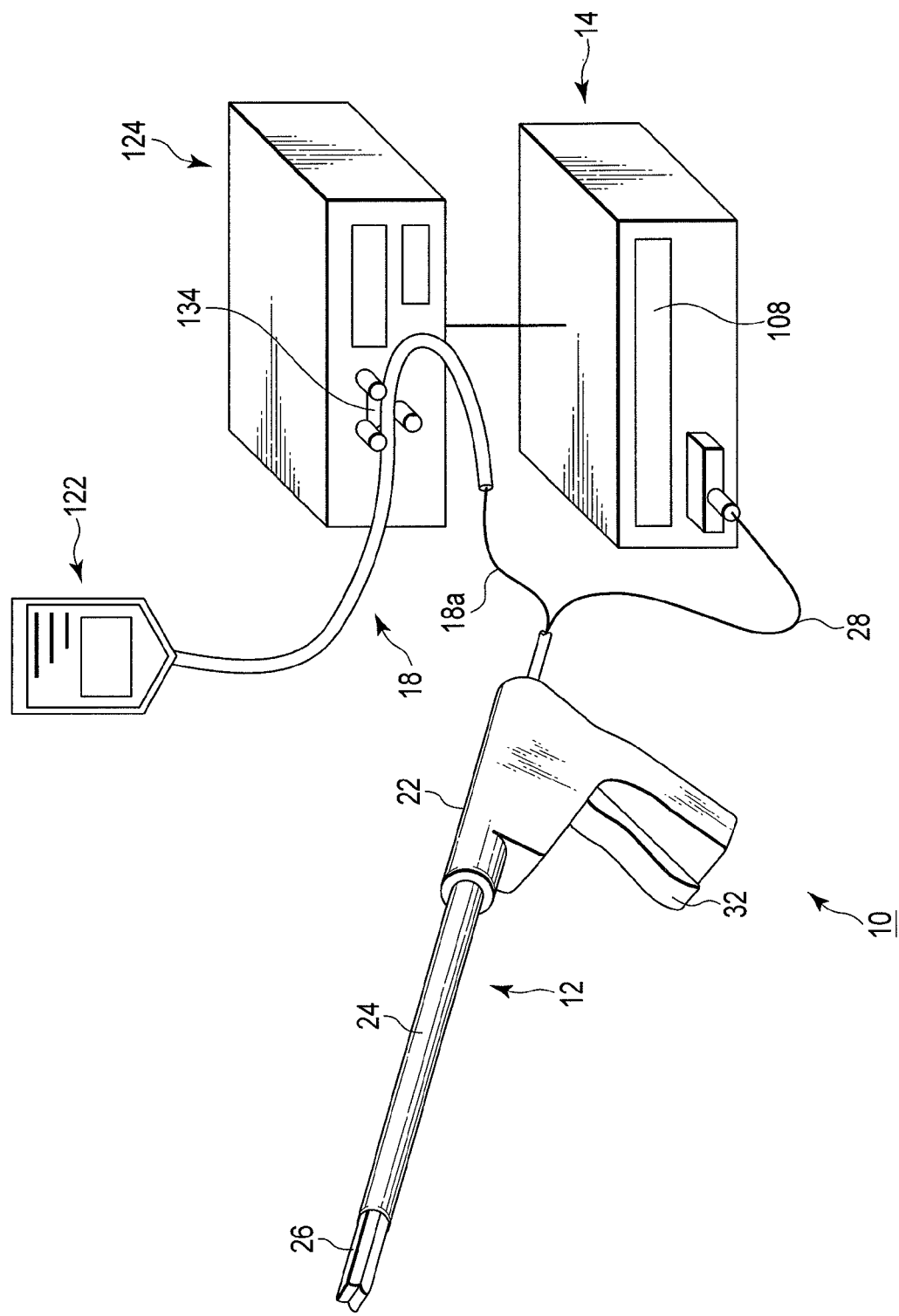
FIG. 1 is a schematic diagram showing a medical treatment system according to a first embodiment.

As shown in FIGS. 1 and 2, a medical treatment system 10 includes the energy treatment device 12, an energy source (control section) 14, a foot switch (or a hand switch) 16, and a fluid source 18.

As shown in FIG. 1, the energy treatment device 12 includes a handle 22, a shaft 24, and a treatment portion (holding portion) 26 which is able to be opened and closed. The handle 22 is connected to the energy source 14 via a cable 28. As shown in FIG. 2, the foot switch 16 is connected to the energy source 14.

The foot switch 16 includes a pedal (not shown). A series of operations such as ON/OFF of the supply of energy (high-frequency energy in the present embodiment) from the energy source 14 to the surgical treatment device 12 and further, whether to make a fluid (conjugation adjunct) flow described later can be switched by the pedal of the foot switch 16 being operated (pressed/released) by an operator. While the pedal is pressed, high-frequency energy is output based on an appropriately set state (state in which the output quantity of energy, timing of energy output and the like are controlled). When pedal pressing is released, the output of high-frequency energy is forced to stop. In addition, a fluid of a predetermined flow rate is made to flow while the pedal is pressed and the flow of the fluid stops when pedal pressing is released.

As shown in FIG. 1, the handle 22 is formed in a shape that makes it easier for the operator to grip and is formed, for example, in a substantially L shape. The shaft 24 is disposed at one end of the handle 22. The cable 28 described above is extended from a proximal end of the handle 22 which is coaxial with the shaft 24. Electrical connection lines 28a, 28b of high-frequency electrodes 92, 94 described later are inserted into the cable 28.

On the other hand, the other end side of the handle 22 is a gripper extending in a direction away from an axial direction of the shaft 24 and gripped by the operator. The handle 22 includes a treatment portion opening/closing knob 32 being arranged side by side. The treatment portion opening/closing knob 32 is coupled to the proximal end of a sheath 44 (see FIGS. 3A and 3B) described later of the shaft 24 in a substantially center portion of the handle 22. If the treatment portion opening/closing knob 32 is moved closer to or away from the other end of the handle 22, the sheath 44 moves along the axial direction thereof.

Figure 3A:
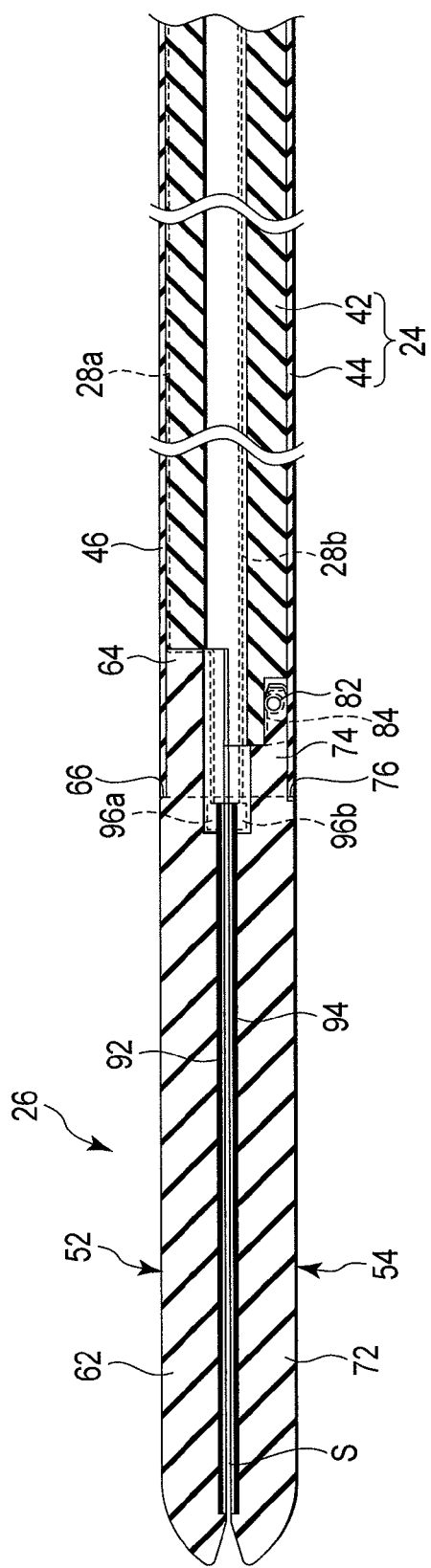
FIG. 3A is a schematic longitudinal sectional view showing a closed treatment portion and a shaft of a bipolar type energy treatment device of the medical treatment system according to the first embodiment.
Figure 3B:
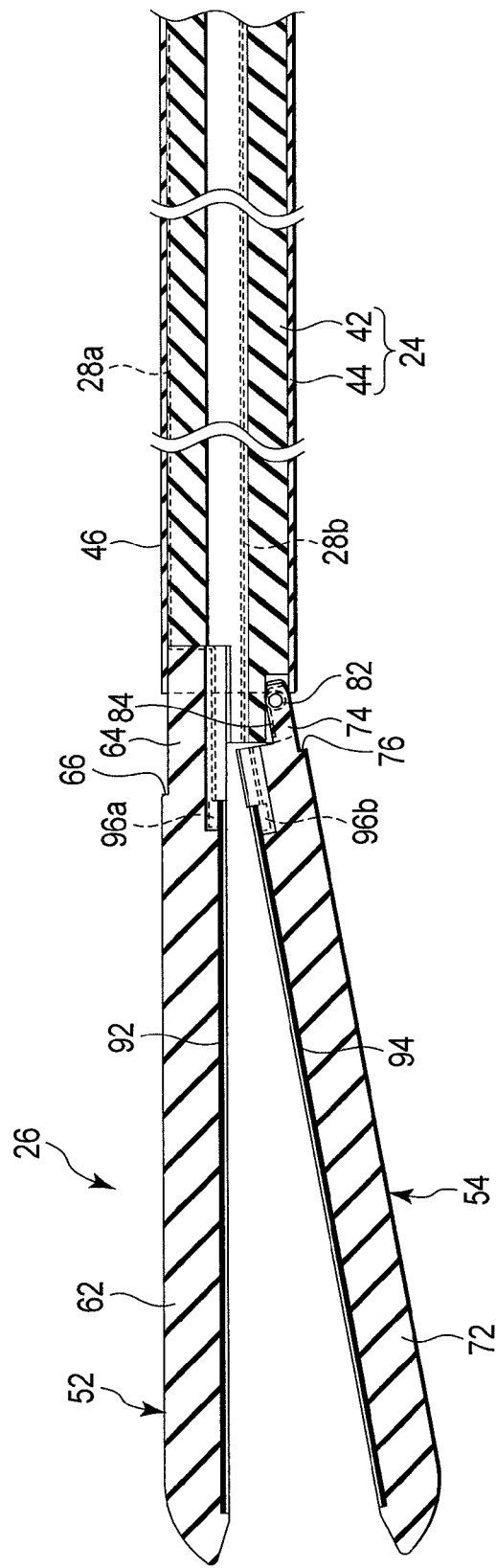
FIG. 3B is a schematic longitudinal sectional view showing the open treatment portion and the shaft of the energy treatment device of the medical treatment system according to the first embodiment.

As shown in FIGS. 3A and 3B, the shaft 24 includes a pipe 42 and the sheath 44 slidably disposed on the outer side of the pipe 42. The base end of the pipe 42 is fixed to the handle 22 (see FIG. 1). The sheath 44 is slidable along the axial direction of the pipe 42.

A recess 46 is formed on the outer side of the pipe 42 along the axial direction thereof. An electrode connection line 28a connected to the high-frequency electrode (energy output portion) 92 described later is disposed in the recess 46. An electrode connection line 28b connected to the high-frequency electrode (energy output portion) 94 described later is inserted into the pipe 42.

As shown in FIG. 1, the treatment portion 26 is disposed at the tip of the shaft 24. As shown in FIGS. 3A and 3B, the treatment portion 26 includes a pair of holding members 52, 54, that is, the first holding member (first jaw) 52 and the second holding member (second jaw) 54.

Figure 4C:
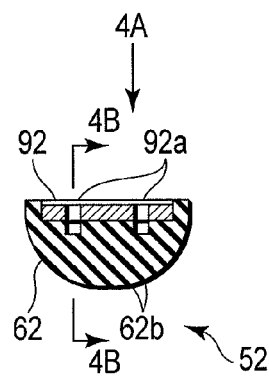
FIG. 4C is a schematic transverse sectional view along a 4C-4C line in FIGS. 4A and 4B, and shows the first holding member of the treatment portion of the energy treatment device of the medical treatment system according to the first embodiment.

The first and second holding members 52, 54 shown in FIGS. 3A and 3B each have suitably insulating properties as a whole. As shown in FIGS. 4A to 4C, the first holding member 52 integrally includes a first holding member main body (hereinafter, referred to mainly as a main body) 62 and a base 64 provided in the proximal end of the main body 62. The main body 62 is a portion which holds body tissues L1, L2 shown in FIG. 5B in collaboration with a main body 72 described later of the second holding member 54 and has a holding surface (edge) 62a. The base 64 is a portion coupled to the tip of the shaft 24. The main body 62 and the base 64 of the first holding member 52 are disposed coaxially. Then, a step 66 is formed between the main body 62 and the base 64.

The second holding member 54 integrally includes, though not illustrated in detail like the first holding member 52 shown in FIGS. 4A to 4C, a second holding member body (hereinafter, referred to mainly as a main body) 72 and a base 74 provided in the proximal end of the main body 72. The main body 72 is a portion that holds the body tissues L1, L2 in collaboration with the main body 62 of the first holding member 52 and has a holding surface (edge) 72a. The base 74 is a portion coupled to the tip of the shaft 24. The main body 72 and the base 74 of the second holding member 54 are disposed coaxially. Then, a step 76 is formed between the main body 72 and the base 74.

In the present embodiment and embodiments described below, the main body 62 of the first holding member 52 and the main body 72 of the second holding member 54 have the same shape. Though the base 74 of the second holding member 54 is different from the base 64 of the first holding member 52 in that the base 74 of the second holding member 54 is formed, as will be described later, so as to be pivotally supported by the pipe 42 of the shaft 24, the base 64 of the first holding member 52 and the base 74 of the second holding member 54 have the same structure in other respects and thus, the description thereof is omitted when appropriate.

As shown in FIG. 4C, an exterior surface of the main body 62 of the first holding member 52 is formed as a smooth curved surface. Though not shown, the exterior surface of the base 64 of the first holding member 52 is also formed as a smooth curved surface. In a state in which the second holding member 54 is closed with respect to the first holding member 52, the transverse section of the treatment portion 26 is formed in a substantially circular shape or a substantially elliptic shape along with the transverse sections of the main bodies 62, 72 and the bases 64, 74. In a state in which the second holding member 54 is closed with respect to the first holding member 52, the holding surfaces (edges) 62a, 72a of the main bodies 62, 72 of the first and second holding members 52, 54 are mutually opposite to each other and in contact. Incidentally, in this state, the outside diameter of the base end of the main bodies 62, 72 of the first and second holding members 52, 54 is formed larger than the outside diameter of the bases 64, 74. Then, the steps 66, 76 described above are formed between the main bodies 62, 72 and the bases 64, 74, respectively.

The first holding member 52 has the base 64 thereof fixed to the tip portion of the pipe 42 of the shaft 24. On the other hand, the second holding member 54 has the base 74 thereof rotatably supported on the tip portion of the pipe 42 of the shaft 24 by a support pin 82 disposed in a direction perpendicular to the axial direction of the shaft 24. The second holding member 54 can be opened and closed with respect to the first holding member 52 by being rotated around the axis of the support pin 82. The second holding member 54 is energized by, for example, an elastic member 84 such as a plate spring so as to be opened with respect to the first holding member 52.

The first and second holding members 52, 54 are formed in a closed state of the second holding member 54 with respect to the first holding member 52 in such a way that an outer circumferential surface in a substantially circular shape or a substantially elliptic shape together with the bases 64, 74 thereof is substantially flush with the outer circumferential surface of the tip portion of the pipe 42 or slightly larger. Thus, the sheath 44 can be slid with respect to the pipe 42 so as to cover the bases 64, 74 of the first and second holding members 52, 54 with the tip of the sheath 44.

In this state, as shown in FIG. 3A, the second holding member 54 is closed with respect to the first holding member 52 against an energizing force of the elastic member 84. On the other hand, if the sheath 44 is slid to the proximal end side of the pipe 42 from the state in which the bases 64, 74 of the first and second holding members 52, 54 are covered with the tip of the sheath 44, as shown in FIG. 3B, the second holding member 54 is opened with respect to the first holding member 52 due to an energizing force of the elastic member 84.

As shown in FIGS. 4A to 4C, the main bodies 62, 72 of the first and second holding members 52, 54 have channels 62b, 72b formed in a concave shape in two rows that are preferably in parallel respectively. That is, the channels 62b, 72b of the main bodies 62, 72 are open to the outside. The tip end of the channels 62b, 72b is blocked.

The bases 64, 74 have ducts 64a, 74a in two rows that are preferably in parallel, respectively. That is, the ducts 64a, 74a of the bases 64, 74 are closed from the outside excluding both ends. The channels 62b, 72b of the main bodies 62, 64 and the ducts 64a, 74a of the bases 64, 74 are formed successively. The tip end of a hose 18a inserted into the shaft 24 and having flexibility is connected to the proximal end of the ducts 64a, 74a of the bases 64, 74. The proximal end of the hose 18a is extended to the outside of the energy treatment device 12 through the handle 22 to be connected to the fluid source 18. Thus, a fluid described later such as a liquid reserved in the fluid source 18 can be led to the ducts 64a, 74a of the bases 64, 74 of the first and second holding members 52, 54 and the channels 62b, 72b of the main bodies 62, 72 through the hose 18a. A transparent or translucent flexible tube is preferably used as the hose 18a outside the energy treatment device 12. By using such a transparent or translucent tube, the flow of a liquid can visually be recognized.

When a liquid is led from the fluid source 18 to the treatment portion 26, the hose 18a is preferably branched out into two or four in positions close to the bases 64, 74 of the first and second holding members 52, 54.

When a liquid is supplied to the first and second holding members 52, 54 through the hose 18a, depending on the viscosity of the liquid led from the fluid source 18 to the treatment portion 26, the supply may be assisted by using pneumatic pressure or the like.

The plate-like high-frequency electrodes (joining members) 92, 94 are disposed as an output member and an energy discharge portion inside the holding surfaces (edges) 62a, 72a of the main bodies 62, 72 of the first and second holding members 52, 54. These high-frequency electrodes 92, 94 are electrically connected to the tip of the electrical connection lines 28a, 28b via connectors 96a, 96b. Then, these electrical connection lines 28a, 28b are connected to a high-frequency energy output portion 104 described later of the energy source 14. Thus, the body tissues L1, L2 are heated and denatured by passing power through the body tissues L1, L2 held between the high-frequency electrodes 92, 94 to generate Joule heat in the body tissues L1, L2.

These high-frequency electrodes 92, 94 are to cap the channels 62b, 72b in a groove shape each in two rows of the main bodies 62, 72 and form each of the channels 62b, 72b as a duct. The high-frequency electrodes 92, 94 have a plurality of openings (a join condition maintenance assistance portion) 92a, 94a formed along each of the channels 62b, 72b. Thus, the fluid from the fluid source 18 described above can be caused to ooze out from the openings 92a, 94a of the high-frequency electrodes 92, 94. Incidentally, the openings 92a, 94a are preferably arranged so that the same quantity of liquid is oozed out from each of the openings 92a, 94a by, for example, equidistant arrangement thereof or adjusting an opening diameter.

Figure 7:
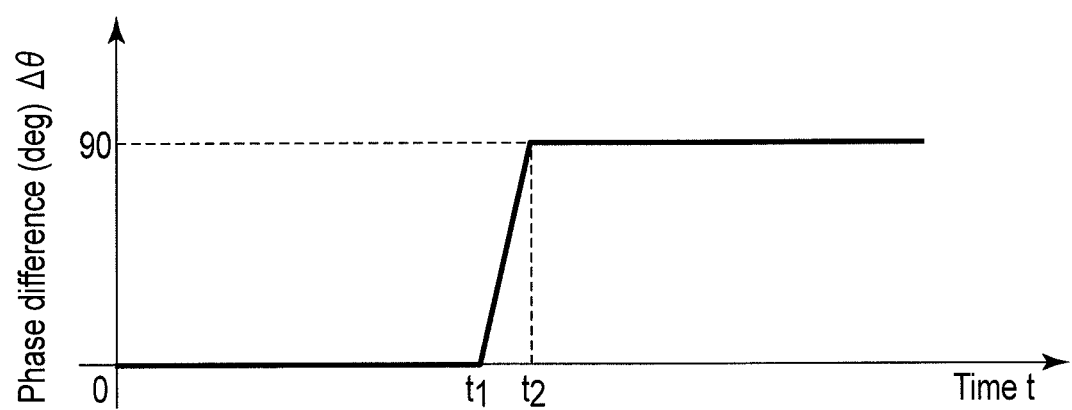
FIG. 7 is a schematic graph showing the relationship between the time and a phase difference when body tissues are held by the treatment portion of the energy treatment device of the medical treatment system and the high-frequency energy is applied to the held body tissues according to a modification of the first embodiment.

These high-frequency electrodes 92, 94 can be used, in addition to treatment of the body tissues L1, L2 by high-frequency energy, as a sensor to measure an impedance Z (see FIG. 5A) between the body tissues L1, L2 or a phase θ (see FIG. 7). The high-frequency electrodes 92, 94 can transmit/receive a signal to/from a detector 106 described later of the energy source 14 through, for example, the electrical connection lines 28a, 28b. It is assumed here that the impedance Z is measured by the detector 106.

As shown in FIG. 2, the energy source 14 includes a first controller (energy control unit) 102, the high-frequency energy output portion (first high-frequency energy output unit) 104, the detector 106, a display unit 108, and a speaker 110. The high-frequency energy output portion 104, the detector 106, the display unit 108, and the speaker 110 are connected to the first controller 102 so that the high-frequency energy output portion 104, the detector 106, the display unit 108, and the speaker 110 are controlled by the first controller 102.

The high-frequency energy output portion 104 generates energy and supplies the energy to the high-frequency electrodes 92, 94 via the electrical connection lines 28a, 28b. Incidentally, the high-frequency energy output portion 104 also functions as an energy output portion that supplies energy to heaters 222, 232 (see FIGS. 26A and 26B) that will be described in the seventh embodiment.

The detector 106 detects measurement results obtained by the high-frequency electrodes 92, 94 holding the body tissues L1, L2 through the electrical connection lines 28a, 28b to calculate the impedance Z. The display unit 108 is a unit in which various settings are made such as the setting of a threshold Z1 of the impedance Z while a setting is checked through the display. The speaker 110 has a sound source (not shown) and produces a sound when a treatment is finished or a problem arises. The sound used to tell the end of treatment and the sound used to tell an occurrence of problem have different tones. The speaker 110 can also produce a distinct sound during treatments, for example, a sound to tell the end of the first step of the treatment and a sound to tell the end of the second step of the treatment.

The foot switch 16 is connected to the first controller 102 of the energy source 14 and also a second controller (flow rate control unit) 132 described later of the fluid source 18 is connected thereto. Thus, if the foot switch 16 is operated, the energy source 14 works and also the fluid source 18 works.

If the foot switch 16 is changed to ON (a pedal not shown is pressed), a treatment by the energy treatment device 12 is carried out and if the foot switch 16 is changed to OFF (the pedal is released), the treatment stops. The display unit 108 functions as a setting unit (controller) when an output quantity (the output quantity itself or what kind of treatment to adopt (treatment for the purpose of joining the body tissues L1, L2, treatment for the purpose of sealing openings of the body tissues or the like)) of the high-frequency energy output portion 104 or output timing of energy is controlled by the first controller 102. It is needless to say that the display unit 108 has a display function to display what is set.

The detector 106 can detect (calculate) the impedance Z of the body tissues L1, L2 between the first and second high-frequency electrodes 92, 94 through the first and second high-frequency electrodes 92, 94 that output high-frequency energy. That is, the detector 106 and the first and second high-frequency electrodes 92, 94 have a sensor function to measure the impedance Z of the body tissues L1, L2 between the first and second high-frequency electrodes 92, 94.

The fluid source 18 includes a fluid reservoir 122 and a flow rate adjuster 124. The flow rate adjuster 124 includes a second controller (flow rate control unit) 132 and a flow rate adjustment mechanism 134.

The fluid reservoir 122 shown in FIG. 1 is formed from, for example, a transparent bag to store a fluid. The proximal end of the hose 18a is removably connected to the fluid reservoir 122. The second controller 132 of the flow rate adjuster 124 is connected to the first controller 102 of the energy source 14. Therefore, the second controller 132 works by being linked to the energy source 14. The flow rate adjustment mechanism 134 is formed from, for example, a pinch cock so as to adjust the flow rate of a fluid flowing into the energy treatment device 12 through the hose 18a. That is, the second controller 132 controls the flow rate of a fluid such as a liquid supplied from the fluid reservoir 122 to the first and second holding members 52, 54 via the hose 18a by operating the flow rate adjustment mechanism 134.

A substance (conjugation adjunct), for example, an adhesive to prevent fluid from infiltrating a body tissue $L_T$ when applied to an exterior surface Sc of the body tissue $L_T$ treated by high-frequency energy can be stored in the fluid reservoir 122. The substance to prevent fluid from infiltrating the body tissue $L_T$ is preferably a bioabsorbable substance which infiltrates body tissues when applied to the body tissues. The substance to be stored in the fluid reservoir 122 may be, in addition to liquids, for example, gel substances. That is, the substance stored in the fluid reservoir 122 may be any fluid that can be passed through the hose 18a. The substance which prevents fluid from penetrating the body tissue $L_T$ contains a compound. The compound is a substance that coats or joins the body tissue $L_T$ by a physical action, a chemical action, or both actions. The compound preferably contains at least one of protein, glucide, polymer, and hardener. The protein suitably contains at least one of fibrin, albumin, collagen, and gelatin. The glucide suitably contains at least one of starch, hyaluronic acid, and chitosan. The polymer is suitably polyethylene glycol, polyglycolic acid, polylactic acid, or polycaprolactam. The hardener is suitably an acrylate derivative, aldehyde derivative, succinimide derivative, or isocyanate derivative. That is, for example, an organic adhesive, inorganic adhesive, bonding biomaterial, crosslinking agent, and monomer/polymer resins can be cited as a substance (joining adjunct) to prevent fluid from penetrating body tissues. When an adhesive is used, various types thereof such as a two-component type can be used.

Further, for example, a liquid or gel substance of adhesive stored in the fluid reservoir 122 may contain an antibiotic, growth promoter and the like.

Table 1 shows main components of eight auxiliary joining members used for experiments to join the body tissues L1, L2 described below and corresponding types of the auxiliary joining members. It is needless to say that main components and types of the auxiliary joining members are not limited to the main components and types shown in Table 1.

TABLE 1

Main components and types of the auxiliary joining members used for experiments to join body tissues

| No. | Main component | Type |
|---|---|---|
| (1) | Cyanoacrylate monomer | Cyanoacrylate adhesive |
| (2) | Fibrinogen Thrombin | Fibrin adhesive |
| (3) | Glutaraldehyde (crosslinking agent) Albumin (main agent) | Aldehyde adhesive |
| (4) | Formaldehyde (crosslinking agent) Glutaraldehyde (crosslinking agent) Gelatin (main agent) | |
| (5) | Organic succinimide (crosslinking agent) Albumin (main agent) | Succinimide adhesive |
| (6) | PEG succinimide (crosslinking agent) Albumin (main agent) | |
| (7) | Polyglycolic acid | Biodegrative polymer |
| (8) | Polycaprolactam | Biodegrative polymer |

If a liquid substance is stored in the fluid reservoir 122, the liquid substance can be led to the ducts 64a, 74a of the bases 64, 74 and the channels 62b, 72b of the main bodies 62, 72 of the first and second holding members 52, 54 of the energy treatment device 12 through the hose 18a connected to the fluid reservoir 122. If a gel substance is stored in the fluid reservoir 122, the gel substance can be led to the duct 64a of the base 64 and the channel 62b of the main body 62 of the first holding member 52 of the energy treatment device 12 through the hose 18a connected to the fluid reservoir 122 by applying, for example, pneumatic pressure or the like to the fluid reservoir 122.

Figure 5A:
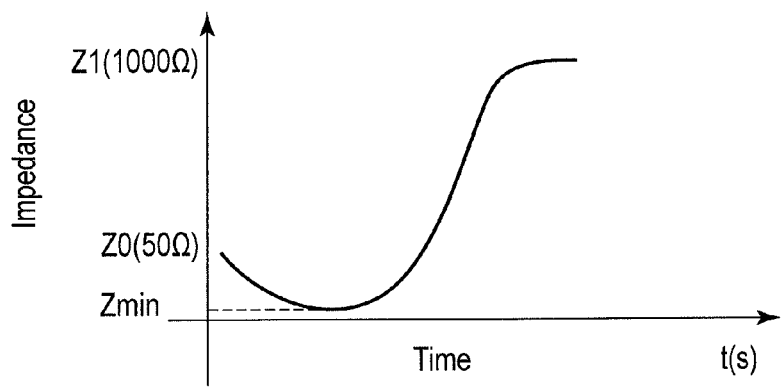
FIG. 5A is a schematic graph showing a relationship between the time and impedance when body tissues are held by the treatment portion of the energy treatment device of the medical treatment system according to the first embodiment and high-frequency energy is applied to the held body tissues.

FIG. 5A shows a relationship between an energy supply time t of the body tissues L1, L2 between the high-frequency electrodes 92, 94 and the impedance Z between the body tissues L1, L2 when desired energy is supplied from the high-frequency energy output portion 104 to the high-frequency electrodes 92, 94 and high-frequency treatment of the body tissues L1, L2 is carried out. FIG. 6 shows an example of the control flow of the surgical treatment device 12 by the high-frequency energy output portion 104.

Next, the action of the medical treatment system 10 according to the present embodiment will be described.

A fluid with which the outer circumference of the body tissue $L_T$ obtained by joining the two body tissues L1, L2 is coated after the body tissues L1, L2 are joined by treatment with high-frequency energy is put into the fluid reservoir 122 of the fluid source 18. It is assumed here that the fluid is an adhesive for the body tissue $L_T$. Particularly, the adhesive suitably has a quick-drying capability with which, for example, the adhesive dries quickly after being exposed to the air. The hose 18a connected to the fluid reservoir 122 is closed by the flow rate adjustment mechanism 134 so that the adhesive does not normally flow from the fluid reservoir 122 toward the energy treatment device 12.

The operator operates the display unit 108 of the energy source 14 in advance to set output conditions for the medical treatment system 10 (step S11). The operator checks the output (set power Pset [W]) from the high-frequency energy output portion 104, the threshold Z1 [Ω] of the impedance Z by the detector 106, a maximum energy supply time t1 [sec] and the like through the display unit 108. If the output from the high-frequency energy output portion 104 or the threshold Z1 of the impedance Z by the detector 106 should be set to a different value, the operator sets the value as desired and checks the value through the display unit 108. The operator also sets a flow rate V1 to be passed from the fluid reservoir 122 to the energy treatment device 12 through the hose 18a. Further, the operator sets a longest time t-max in which the hose 18a is opened. That is, even if the flow rate V1 is not reached after the hose 18a is opened, the hose 18a is automatically closed after the time t-max passes.

As shown in FIG. 3A, the treatment portion 26 and the shaft 24 of the surgical treatment device 12 are inserted into the abdominal cavity through, for example, the abdominal wall in the state in which the second holding member 54 is closed to the first holding member 52. The treatment portion 26 of the surgical treatment device 12 is opposed to the body tissues L1, L2 to be treated (to be held).

The operator operates the treatment portion opening/closing knob 32 of the handle 22 to hold the body tissues L1, L2 to be treated by the first holding member 52 and the second holding member 54. With this operation, the sheath 44 is moved to the side of the proximal end of the shaft 24 with respect to the pipe 42. The space between the bases 64, 74 can no longer be maintained in a cylindrical shape due to the energizing force of the elastic member 84 and the second holding member 54 is opened with respect to the first holding member 52.

The body tissues L1, L2 to be joined (to be treated) are arranged between the high-frequency electrodes 92, 94 of the first and second holding members 52, 54. The treatment portion opening/closing knob 32 of the handle 22 is operated in this state. In this case, the sheath 44 is moved to the distal side of the shaft 24 with respect to the pipe 42. The space between the bases 64, 74 is closed by the sheath 44 against the energizing force of the elastic member 84 and to make it into a cylindrical shape. Thus, the main body 62 of the first holding member 52 formed integrally with the base 64 and the main body 72 of the second holding member 54 formed integrally with the base 74 are closed. That is, the second holding member 54 is closed with respect to the first holding member 52. In this manner, the body tissues L1, L2 to be joined are held between the first holding member 52 and the second holding member 54.

In this case, the body tissue L1 to be treated is in contact with the high-frequency electrode 92 of the first holding member 52 and the body tissue L2 to be treated is in contact with the high-frequency electrode 94 of the second holding member 54. Peripheral tissues of the body tissues L1, L2 to be joined are closely in contact with both opposite contact surfaces of the holding surface (edge) 62a of the main body 62 of the first holding member 52 and the holding surface (edge) 72b of the main body 72 of the second holding member 54. Incidentally, a contact surface C1 of the body tissue L1 and a contact surface C2 of the body tissue L2 are in contact in such a way that pressure is applied to each other.

Thus, the operator operates the pedal of the foot switch 16 while the body tissues L1, L2 are held between the first holding member 52 and the second holding member 54. A signal is input into the first controller 102 from the foot switch 16 and the first controller 102 of the energy source 14 determines whether the switch 16 is changed to ON by pressing the pedal thereof through the operation of the operator (S12).

If the first controller 102 determines that the switch 16 is changed to ON by pressing the pedal thereof, a signal is input into the high-frequency energy output portion 104 from the first controller 102. The high-frequency energy output portion 104 generates energy and supplies the energy to the body tissues L1, L2 between the high-frequency electrodes 92, 94 through the electrical connection lines 28a, 28b (S13). At this point, the high-frequency energy output portion 104 supplies the set power Pset [W] set in advance through the display unit 108, for example, power of about 20 [W] to 80 [W] to between the high-frequency electrode 92 of the first holding member 52 and the high-frequency electrode 94 of the second holding member 54.

Thus, the high-frequency energy output portion 104 passes a high-frequency current to the body tissues L1, L2 to be joined between the high-frequency electrode 92 of the first holding member 52 and the high-frequency electrode 94 of the second holding member 54. That is, the high-frequency energy output portion 104 applies high-frequency energy to the body tissues L1, L2 held between the high-frequency electrodes 92, 94. Thus, the body tissues L1, L2 are heated by generating Joule heat in the body tissues L1, L2 held between the high-frequency electrodes 92, 94. Cell membranes inside the body tissues L1, L2 held between the high-frequency electrodes 92, 94 are destroyed by the action of Joule heat to release substances inside the cell membrane so that the substances are equalized with components outside the cell membrane including collagen. Since a high-frequency current is being passed to the body tissues L1, L2 between the high-frequency electrodes 92, 94, further Joule heat is acted on the equalized body tissues L1, L2 to conjugate, for example, the contact surfaces C1, C2 of the body tissues L1, L2 or layers of tissues. Therefore, if a high-frequency current is passed to the body tissues L1, L2 between the high-frequency electrodes 92, 94, the body tissues L1, L2 are heated and so the inside of the body tissues L1, L2 is denatured (the body tissues L1, L2 are burned) while the body tissues L1, L2 are dehydrated, generating a joined portion C after the contact surfaces C1, C2 are brought into close contact. In this manner, the two body tissues L1, L2 are joined to form the body tissue $L_T$ having the joined portion C.

With an increasing level of denaturation of the body tissues L1, L2, a fluid (for example, a liquid (blood) and/or a gas (vapor)) is released from the body tissues L1, L2. In this case, the holding surfaces 62a, 72a of the main bodies 62, 72 of the first and second holding members 52, 54 have higher adhesiveness to the body tissues L1, L2 than the high-frequency electrodes 92, 94. Thus, the holding surfaces 62a, 72a function as a barrier portion (dam) that inhibits a fluid from the body tissues L1, L2 from escaping to the outside of the first holding member 52 and the second holding member 54. That is, a thermal spread can be prevented from being generated in body tissues other than the body tissues L1, L2 to be treated and joined.

In this case, the high-frequency electrodes 92, 94 of the first and second holding members 52, 54 have a sensor function and thus transmit information (impedance Z) about between the held body tissues L1, L2 to the detector 106 through the electrical connection lines 28a, 28b. As shown in FIG. 5A, an initial value Z0 of the impedance Z when treatment is started (when the supply of high-frequency energy to between the body tissues L1, L2 is started) is, for example, about 50 [Ω] to 60 [Ω]. As the body tissues L1, L2 are increasingly burned by the high-frequency current flowing into the body tissues L1, L2, the impedance Z drops to Zmin (for example, about 10 [Ω]) and then gradually rises.

The first controller 102 controls the detector 106 so that information about the body tissues L1, L2 between the high-frequency electrodes 92, 94 is calculated at equal time intervals (for example, a few milliseconds). The first controller 102 determines whether the impedance Z during high-frequency energy output operated based on a signal from the detector 106 is equal to or more than the threshold Z1 (here, as shown in FIG. 5A, about 1000 [Ω]) set (S11) in advance through the display unit 108 (S14). It is, needless to say, that the threshold Z1 of the impedance Z can appropriately be set.

For example, the threshold Z1 is preferably larger than the initial value Z0 and in a position (see FIG. 5A) where the rate of rise of the value of the impedance Z slows down. If the first controller 102 determines that the impedance Z has reached the threshold Z1 or exceeded the threshold Z1, a signal is conveyed from the first controller 102 to the high-frequency energy output portion 104. Then, the output from the high-frequency energy output portion 104 to the high-frequency electrodes 92, 94 of the first and second holding members 52, 54 is stopped (S151).

On the other hand, if the impedance Z has not reached the threshold Z1, the output of energy is continued. If the first controller 102 determines that the impedance Z between the body tissues L1, L2 is smaller than the threshold Z1, high-frequency energy for treatment will continue to be given to the body tissues L1, L2 held between the high-frequency electrodes 92, 94 of the first and second holding members 52, 54. Then, if the impedance Z between the body tissues L1, L2 reaches the threshold Z1 or a predetermined time t passes after the start of energy supply from the high-frequency energy output portion 104, the high-frequency energy output portion 104 is caused to stop the output of energy. At this point, the body tissue $L_T$ is joined by the joined portion C.

Then, the pedal of the foot switch 16 continues to be pressed. The body tissue $L_T$ maintains a state in which the body tissue $L_T$ is held by the holding members 52, 54.

The supply of energy from the high-frequency energy output portion 104 to the high-frequency electrodes 92, 94 is stopped by the first controller 102 (S151) and at the same time, a signal is conveyed from the first controller 102 to the second controller 132. The second controller 132 causes the flow rate adjustment mechanism 134 to operate to open the hose 18a (S152). Thus, an adhesive is supplied from the fluid reservoir 122 to the energy treatment device 12 through the hose 18a. That is, the adhesive is supplied from the fluid reservoir 122 to the ducts 64a, 74a of the bases 64, 74 and the channels 62b, 72b of the main bodies 62, 72 of the first and second holding members 52, 54 by the hose 18a through inner portions of the handle 22 and the shaft 24. Thus, the adhesive is oozed out from the openings 92a, 94a of the high-frequency electrodes 92, 94 formed along the channels 62b, 72b of the main bodies 62, 72.

The adhesive oozed out from the openings 92a, 94a of the high-frequency electrodes 92, 94 is spread and applied to coat the outer circumferential surface of joined body tissues. That is, the adhesive is applied to the entire surface through which the high-frequency electrodes 92, 94 and body tissues are in contact. Then, the adhesive is gradually hardened with the passage of time if, for example, exposed to the air. The adhesive preferably has a quick-drying capability and has waterproof when hardened. Thus, the exterior surface Sc of the body tissue $L_T$ joined with hardening of the adhesive is coated. Therefore, a liquid can be prevented from infiltrating from the exterior surface Sc of the joined body tissue $L_T$ into the joined portion C (between the contact surfaces C1, C2).

Adhesives have naturally different properties depending on the type of adhesive and the reason why the adhesive in the present embodiment is applied after the body tissues L1, L2 are joined is that an adhesive for body tissues can display an effective adhesive action when applied in as dry a state of the body tissues L1, L2 as possible. That is, if an adhesive is applied in a state in which a sufficient amount of moisture is not removed, it becomes more difficult to remove moisture from the body tissues L1, L2 even if energy is provided, but such a state can be prevented by applying the adhesive after the body tissues L1, L2 are joined. In addition, if an adhesive is applied in a state in which a sufficient amount of moisture is not removed, the adhesive may be mixed with fluid, but such a state can be prevented by applying the adhesive after the body tissues L1, L2 are joined.

When the adhesive of a predetermined flow rate is passed from the fluid reservoir 122 through the hose 18a (S16) or after the hose 18a is opened for a predetermined time, the second controller 132 causes the flow rate adjustment mechanism 134 to operate again to close the hose 18a (S17).

When a predetermined time (for example, a few seconds) passes after the hose 18a is closed, a sound such as a buzzer from the speaker 110 is emitted to tell the completion of treatment (conjugation treatment of body tissues and treatment to prevent fluid from infiltrating into the joined contact surfaces C1, C2) (S18). Then, after making sure that the treatment has completed with the sound from the speaker 110 or the display of the display unit 108, a medical doctor or the like releases the pedal by removing his or her foot from the pedal of the foot switch 16.

The treatment continues from "Start" to "End" shown in FIG. 6 while the pedal of the foot switch 16 is kept pressed, but if the pedal is released at some point between "Start" and "End", the first controller 102 forces the treatment to stop when pressing of the pedal is released. That is, if the supply of high-frequency energy should be stopped in midstream or the supply of adhesive should be stopped in midstream, pressing of the pedal of the foot switch 16 is released by removing a foot from the pedal before a sound such as a buzzer is emitted from the speaker 110. When pressing of the pedal is released, the first controller 102 forces to stop the output of energy from the high-frequency energy output portion 104 to electrodes 92, 94 if the energy is output from the high-frequency energy output portion 104. When the hose 18a is opened, the second controller 132 forces to stop supply of a fluid by causing the flow rate adjustment mechanism 134 to operate to close the hose 18a.

Figure 5B:
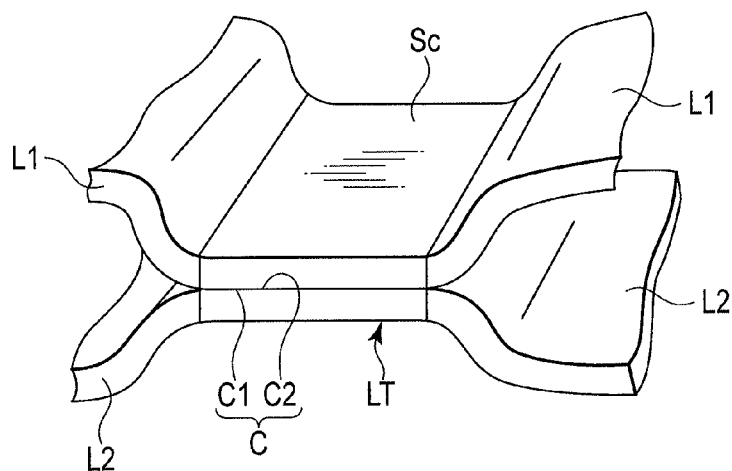
FIG. 5B is a schematic perspective view showing a state of body tissues immediately after being treated by using the energy treatment device of the medical treatment system according to the first embodiment.

After checking the buzzer sound from the speaker 110, the medical doctor operates the treatment portion opening/closing knob 32 to release the body tissue $L_T$. In this case, as shown in FIG. 5B, the contact surfaces C1, C2 of body tissues are joined to form the joined portion C. Moreover, the adhesive having bioabsorbability is hardened while infiltrating from the exterior surface Sc to the joined portion C in the body tissue $L_T$ and thus, the body tissue $L_T$ is in a state of being coated with the adhesive. Because the adhesive has bioabsorbability, the adhesive oozed out from the openings 92a, 94a may also be applied to the side face of the body tissues L1, L2 shown in FIG. 5B.

According to the present embodiment, as described above, the following effect is achieved.

Close contact of the contact surfaces C1, C2 of the body tissues L1, L2 can be made more reliable by treating and joining the body tissues L1, L2 while the impedance Z of the body tissues L1, L2 is measured. After the body tissues L1, L2 are treated for conjugation, fluid can be prevented from seeping through into the joined portion C of the body tissue $L_T$ treated for conjugation by coating the outer circumference of the body tissue $L_T$ treated for conjugation with an adhesive or the like. Therefore, a state in which the contact surfaces C1, C2 of the body tissues L1, L2 can closely be in contact (state in which the body tissue $L_T$ is joined) for a long time.

If a two-component adhesive is used as a fluid substance to coat the outer circumference of the joined body tissue $L_T$ after the body tissues L1, L2 are joined, two types of liquids may be provided side by side in the fluid source 18. In this case, the two hoses 18a are extended from the fluid source 18 to the energy treatment device 12 side by side to supply liquids to the channels 62b, 72b of the main bodies 62, 72 of the first and second holding members 52, 54 through the handle 22 and the shaft 24 independently. Then, two liquids are made to be mixed when oozed out from the openings 92a, 94a of the high-frequency electrodes 92, 94. In this manner, the adhesive can be prevented from being hardened inside the hose 18a or the first and second holding members 52, 54. When a two-component adhesive is used, it is also preferable to form two channels (not shown) in a hose 18a.

While an example in which the impedance Z (see FIG. 5A) is used as living body information detected by the detector 106 is described in the above embodiment, it is also preferable to use the amount of change of the phase (phase difference $\Delta\theta$) (see FIG. 7) as living body information. When the phase difference $\Delta\theta$ is used, as shown in FIG. 8, the detector 106 includes a voltage detector 142, a current detector 144, and a phase detector 146. The phase detector 146 is connected to the first controller 102. The voltage detector 142 and the current detector 144 are connected to the energy treatment device 12 (high-frequency electrodes 92, 94) and also connected to the phase detector 146. This is not limited to the first embodiment and similarly applies to other embodiments described later.

If the high-frequency energy output portion 104 is caused to generate a high-frequency voltage, a high-frequency current having a predetermined frequency and peak value based on the high-frequency voltage of the high-frequency energy output portion 104 is output to the surgical treatment device 12 via the current detector 144. The voltage detector 142 detects the peak value of the high-frequency voltage through the high-frequency energy output portion 104 and outputs the detected peak value to the phase detector 146 as output voltage value information. The current detector 144 detects the peak value of the high-frequency current generated based on the high-frequency voltage through the high-frequency energy output portion 104 and outputs the detected peak value to the phase detector 146 as output current value information.

After detecting the phase of the high-frequency voltage output through the high-frequency energy output portion 104 based on output voltage value information output from the voltage detector 142, the phase detector 146 outputs the detected phase to the first controller 102 as output voltage phase information along with output voltage value information. Also after detecting the phase of the high-frequency current through the high-frequency energy output portion 104 based on output current value information output from the current detector 144, the phase detector 146 outputs the detected phase to the first controller 102 as output current phase information along with output current value information.

Based on output voltage value information, output voltage phase information, output current value information, and output current phase information output from the phase detector 146, the first controller 102 calculates the phase difference $\Delta\theta$ of the high-frequency voltage and high-frequency current output through the high-frequency energy output portion 104.

The first controller 102 controls the high-frequency energy output portion 104 to change the output state of the high-frequency current and high-frequency voltage to the ON state or OFF state based on an instruction signal output in accordance with an operation of the pedal of the foot switch 16 and the calculated phase difference Δθ.

As shown in FIG. 7, the phase difference Δθ of the high-frequency current or high-frequency voltage output through the high-frequency energy output portion 104 is 0° or substantially 0° in the initial stage of treatment on the body tissue $L_T$. Incidentally, the value of the phase difference Δθ is set to 90° or a value close thereto through the display unit 108.

As the pedal of the foot switch 16 is pressed uninterruptedly and treatment of the body tissues L1, L2 held between the high-frequency electrodes 92, 94 of the first and second holding members 52, 54 proceeds, the body tissues L1, L2 are dehydrated followed by being cauterized or coagulated. If the treatment proceeds in this manner, the phase difference Δθ of the high-frequency current or high-frequency voltage output through the high-frequency energy output portion 104 increases from the state of 0° or substantially 0°, for example, after a suitable time t1.

Then, if treatment of a desired region proceeds by the pedal of the foot switch 16 being further pressed uninterruptedly, the value of the phase difference Δθ calculated by the first controller 102 takes a fixed value near 90° shown in FIG. 7, for example, after the time t1.

In this modification, the first controller 102 is not limited to the above control exercised when detecting that the phase difference Δθ has become a fixed value near 90° and may be, for example, the above control exercised when detecting that the phase difference Δθ has become a fixed predetermined value greater than 45° and equal to or less than 90°.

Energy input into the body tissues L1, L2 may be switched by combining the change of the impedance Z and the change of the phase θ. That is, it is also preferable to appropriately set by the display unit 108 and use the change of the impedance Z and the change of the phase θ such as a value which is the earlier or the later of reaching a threshold.

As will be described later in the seventh embodiment (see FIGS. 26A and 26B), instead of the high-frequency electrodes 92, 94, thermal energy using the heaters 222, 232 may be used for treatment. In this case, the treatment proceeds while the temperature of body tissues in contact with the heaters 222, 232 is measured.

A case when the bipolar type energy treatment device 12 is used is described in the present embodiment, but a monopolar type treatment device (see FIG. 9) may also be used.

Figure 9:
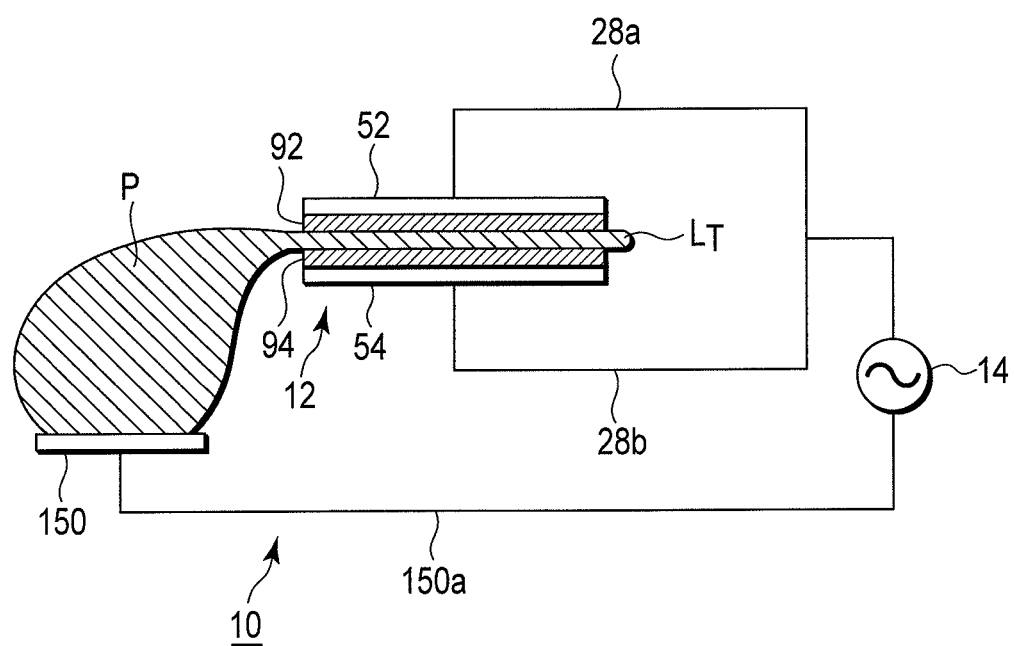
FIG. 9 is a schematic diagram showing the state of body tissues being treated by using the monopolar type energy treatment device of the medical treatment system according to the modification of the first embodiment.

In such a case, as shown in FIG. 9, a return electrode plate 150 is mounted on a patient P to be treated. The return electrode plate 150 is connected to the energy source 14 via an electrical connection line 150a. Further, the high-frequency electrode 92 disposed on the first holding member 52 and the high-frequency electrode 94 disposed on the second holding member 54 are in a state of the same electric potential in which the electrical connection lines 28a, 28b are electrically connected. In this case, each area of the body tissues L1, L2 in contact with the high-frequency electrodes 92, 94 is sufficiently smaller than the area where the return electrode plate 150 is in contact with the living body and so a current density is increased, but the current density in the return electrode plate 150 depresses. Thus, while the body tissues L1, L2 held by the first and second holding members 52, 54 are heated by Joule heat, heating of body tissues in contact with the return electrode plate 150 is so small to be ignorable. Therefore, among the body tissues L1, L2, grasped by the first and second holding members 52, 54, only a portion thereof in contact with the high-frequency electrodes 92, 94 at the same potential is heated and denatured.

In the present embodiment, a case when the body tissues L1, L2 are treated by using high-frequency energy has been described, but energy of, for example, a microwave may also be used. In such a case, the high-frequency electrodes 92, 94 can be used as microwave electrodes.

Figure 10:
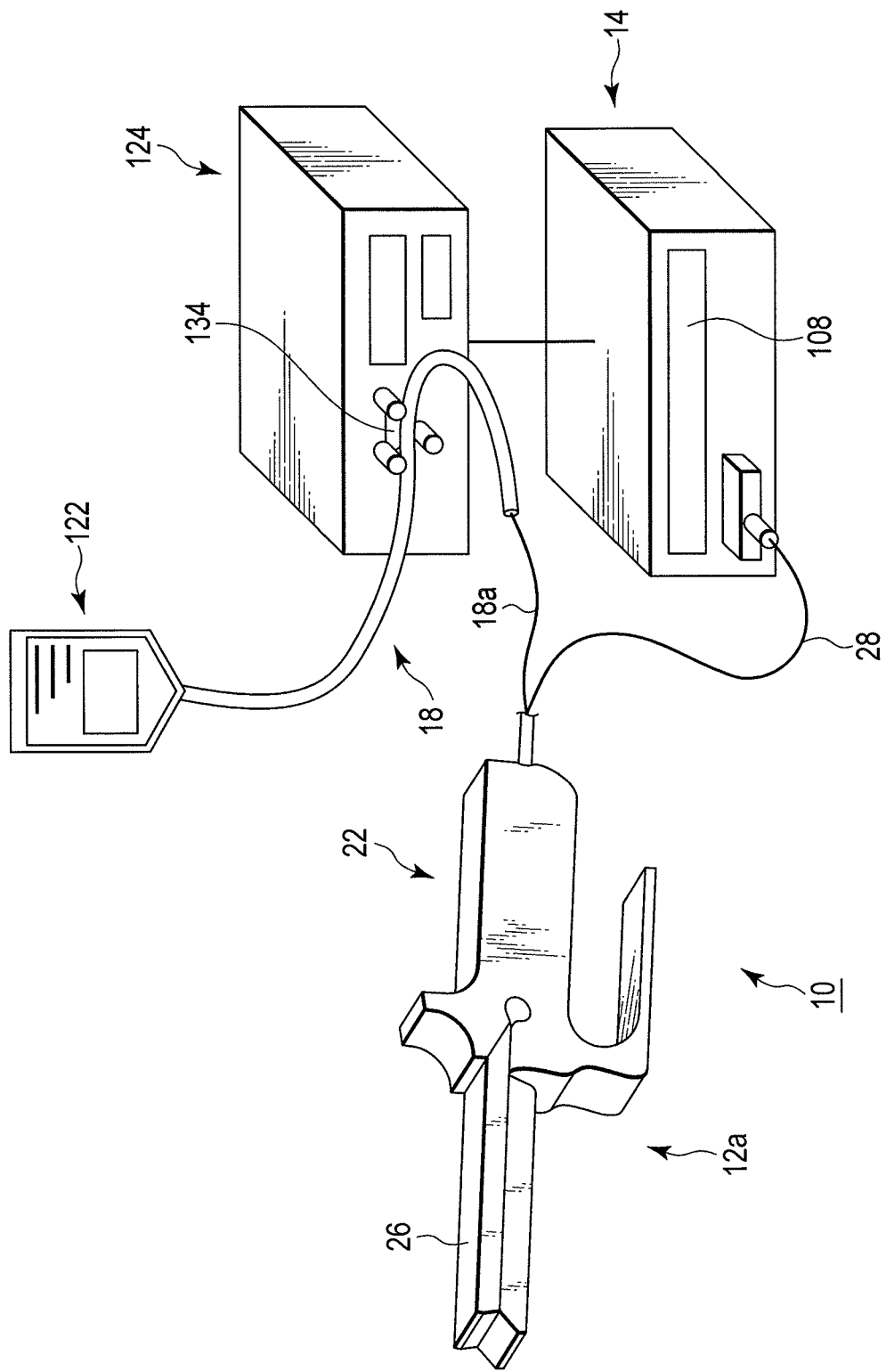
FIG. 10 is a schematic diagram showing the medical treatment system according to the modification of the first embodiment.

The present embodiment has been described by taking the linear-type energy treatment device 12 (see FIG. 1) to treat the body tissues L1, L2 in the abdominal cavity (in the body) through the abdominal wall as an example, but as shown, for example, in FIG. 10, an open linear-type energy treatment device (medical treatment device) 12a for treatment by taking tissues to be treated out of the body through the abdominal wall may also be used.

The energy treatment device 12a includes the handle 22 and the treatment portion (holding portion) 26. That is, in contrast to the energy treatment device 12 (see FIG. 1) for treatment through the abdominal wall, the shaft 24 is removed. On the other hand, a member having the same action as the shaft 24 is disposed inside the handle 22. Thus, the energy treatment device 12a shown in FIG. 10 can be used in the same manner as the energy treatment device 12 shown in FIG. 1 described above.

An adhesive may be directly supplied into body tissues by an injector such as a syringe instead of using the fluid reservoir 122. As a supply method of adhesive, the flow rate adjuster 124 may control the flow rate of adhesive into body tissues by using a rotary pump or the like. Though not specifically described, it is permitted to directly supply an adhesive or the like into body tissues by an injector such as a syringe also in embodiments described below.

Second Embodiment

Next, the second embodiment will be described using FIGS. 11A to 11C. The present embodiment is a modification of the first embodiment and the same reference numerals are attached to the same members as those used in the first embodiment or members achieving the same action as the action of those in the first embodiment and a description of such members is omitted.

Figure 11A:
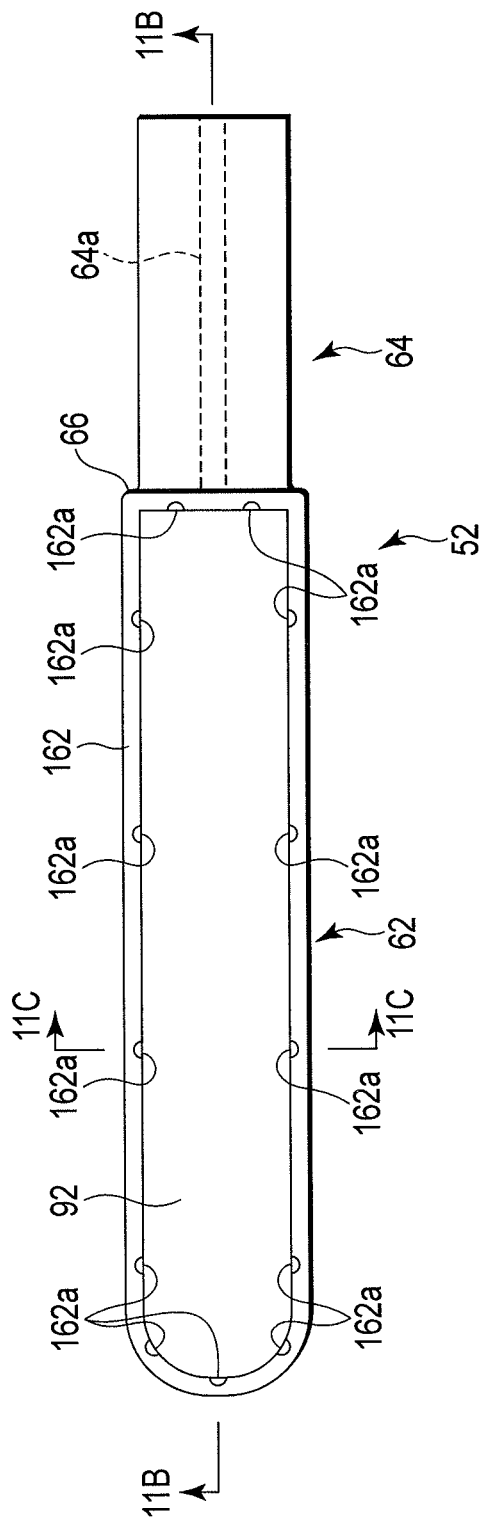
FIG. 11A is a schematic plan view viewed from an arrow 11A direction in FIGS. 11B and 11C, and shows a first holding member of a treatment portion of an energy treatment device of a medical treatment system according to a second embodiment.

Instead of a channel (recess) 62b (see FIGS. 4A to 4C), a fluid conduit 162 having insulating properties is disposed on a main body 62 of a first holding member 52 shown in FIGS. 11A to 11C. The openings 92a, 94a of the high-frequency electrodes 92, 94 described in the first embodiment are removed.

The fluid conduit 162 is disposed on a ring shape in a position close to the surface of the high-frequency electrode 92 along edges of the outer circumference of the main body 62. As shown in FIG. 11C, the transverse section of the fluid conduit 162 is formed, for example, in a circular shape or rectangular shape. The fluid conduit 162 preferably has an appropriate elasticity so as to be in close contact with an exterior surface of the body tissue L1 when the body tissues L1, L2 are held by the first and second holding members 52, 54. The fluid conduit 162 is connected to the duct 64a of the base 64 of the first holding member 52. Incidentally, the high-frequency electrode 92 is disposed inside the fluid conduit 162.

The fluid conduit 162 includes a plurality of openings (a join condition maintenance assistance portion) 162a at suitable intervals. As shown in FIGS. 11B and 11C, these openings 162a are directed toward the surface of the high-frequency electrode 92 and also directed toward the center axis of the high-frequency electrode 92. Thus, a fluid discharged from the openings 162a of the fluid conduit 162 can be passed along the surface of the high-frequency electrode 92 toward the center axis of the high-frequency electrode 92.

Because, as shown in FIG. 11A, the openings 162a of the fluid conduit 162 are positioned close to the surface of the high-frequency electrode 92, a portion of the fluid conduit 162 is projected from the surface of the high-frequency electrode 92. Thus, when the body tissues L1, L2 are treated using the high-frequency electrode 92, the fluid conduit 162 serves as a barrier portion that prevents a fluid such as a steam from being leaked to the outside, the fluid such as a steam being generated from the body tissues L1, L2 when the body tissues L1, L2 are treated using the high-frequency electrode 92.

Though not shown, a fluid conduit 164 having openings (a conjugation maintenance assistance portion) 164a is also disposed at edges of a main body 72 of the second holding member 54 symmetrically with respect to the first holding member 52. Thus, the fluid conduit 164 serves as a barrier portion that prevents a fluid such as a steam from being leaked to the outside, the fluid such as a steam being generated from the body tissues L1, L2 when the body tissues L1, L2 are treated using the high-frequency electrode 94. The fluid conduit 164 is connected to the duct 74a of the base 74 of the second holding member 54.

Though not shown, the fluid conduit 162 is preferably formed as a double lumen so that one (inner side) is a duct having the openings 162a and the other (outer side) is a duct that passes a gas or liquid as a refrigerant. In this case, a portion of the body tissues L1, L2 in contact with the fluid conduit 162 can be cooled by circulating a refrigerant through the other duct (duct on the outer side). Therefore, heat can be prevented from conducting to the outer side of the holding surfaces 62a, 72a of the first and second holding members 52, 54 through the body tissues L1, L2 so that the body tissues L1, L2 outside the body tissues L1, L2 to be treated can more reliably be prevented from being affected by heat.

The other structures and actions of the medical treatment system 10 are the same as those described in the first embodiment and thus, a description thereof is omitted.

Third Embodiment

Next, the third embodiment will be described using FIGS. 12 to 16. The present embodiment is a modification of the first and second embodiments and the same reference numerals are attached to the same members as those used in the first and second embodiments or members achieving the same action as the action of those in the first and second embodiments and a description of such members is omitted.

Figure 12:
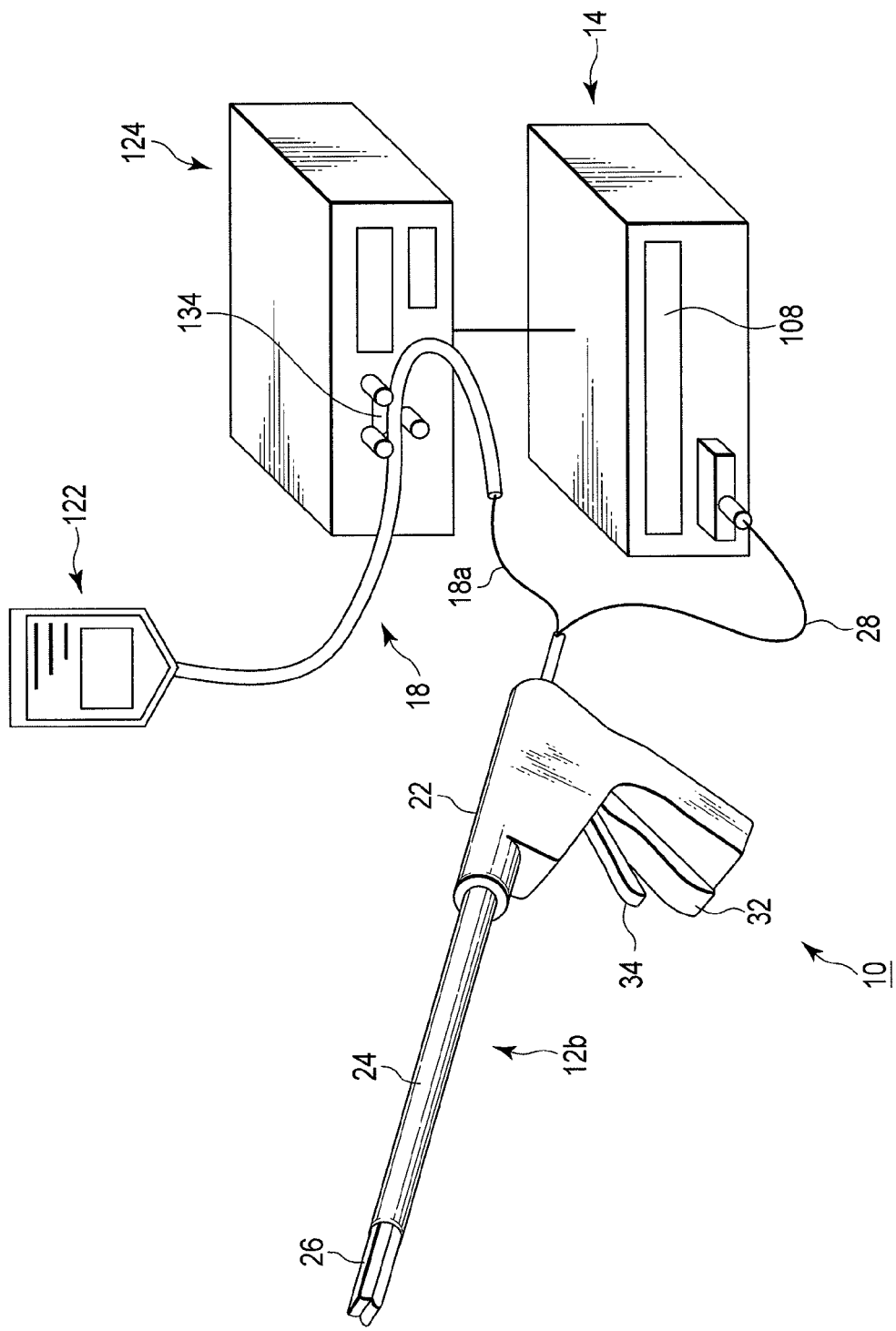
FIG. 12 is a schematic diagram showing a medical treatment system according to a third embodiment.

As shown in FIG. 12, a handle 22 of an energy treatment device 12b includes a cutter driving knob 34 to move a cutter (auxiliary treatment device) 180 described later while being installed adjacent to the treatment portion opening/closing knob 32.

As described in FIG. 13, in addition to a detector (called a first detector here) 106 described in the first embodiment, a second detector 107 is connected to a first controller 102 in an energy source 14. The second detector 107 is connected to a sensor 185 disposed in locking portions 184a, 184b, 184c of a long groove 184 described later of the cutter 180.

The external shapes of main bodies 62, 72 and bases 64, 74 of first and second holding members 52, 54 are formed similarly to the external shapes of the first and second holding members 52, 54 in the second embodiment except that cutter guiding grooves 172, 174 described later are formed.

As shown in FIGS. 14A to 15B, the straight cutter guiding groove 172 is formed on the main body 62 and the base 64 of the first holding member 52 closer to the second holding member 54. Similarly, the straight cutter guiding groove 174 is formed on the main body 72 and the base 74 of the second holding member 54 closer to the first holding member 52. A cutter 180 described later is configured to advance to/retreat from these cutter guiding grooves 172, 174.

Figure 14A:
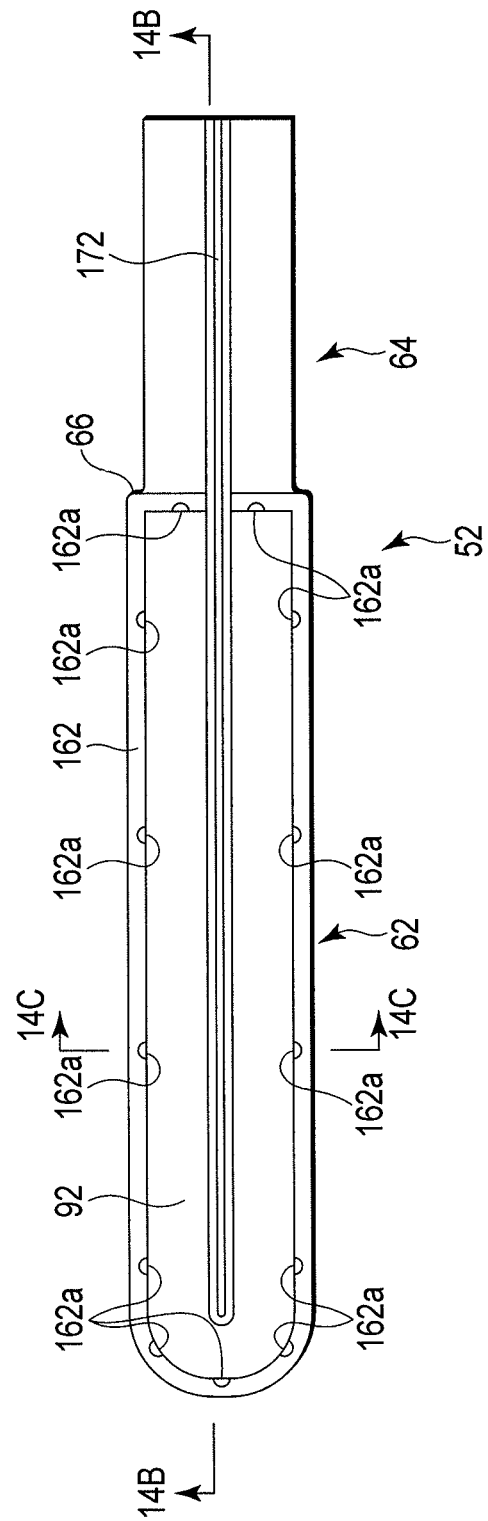
FIG. 14A is a rough plan view viewed from an arrow 14A direction in FIGS. 14B and 14C, and shows a first holding member of a treatment portion of an energy treatment device of the medical treatment system according to the third embodiment.

As shown in FIG. 14A, high-frequency electrodes 92, 94 disposed on the main bodies 62, 72 of the first and second holding members 52, 54 are formed, for example, in a substantial U shape and each have two ends in the proximal end of the main bodies 62, 72 of the first and second holding members 52, 54. That is, each of the high-frequency electrodes 92, 94 is formed continuously. The high-frequency electrodes 92, 94 have cutter guiding grooves (reference numerals 172, 174 are conveniently attached) to guide the cutter 180 formed together with the first and second holding members 52, 54.

The cutter guiding grooves 172, 174 of the first and second holding members 52, 54 are formed in a mutually opposite state along the axial direction of a shaft 24. Then, the cutter 180 can be guided by the two collaborating cutter guiding grooves 172, 174 of the first and second holding members 52, 54.

The cutter guiding groove 172 of the first holding member 52 is formed on the center axis of the main body 62 and the base 64 of the first holding member 52 and the cutter guiding groove 174 of the second holding member 54 is formed on the center axis of the main body 72 and the base 74 of the second holding member 54.

A driving rod 182 is movably disposed inside a pipe 42 of the shaft 24 along the axis direction thereof. The cutter driving knob 34 is disposed at the proximal end of the driving rod 182. The cutter (auxiliary treatment device) 180 in a thin plate shape is disposed at the tip end of the driving rod 182. Thus, if the cutter driving knob 34 is operated, the cutter 180 moves along the axial direction of the shaft 24 via the driving rod 182.

The cutter 180 has a cutting edge 180a formed at the tip end thereof and the tip end of the driving rod 182 is fixed to the proximal end thereof. A long groove 184 is formed between the tip end and the proximal end of the cutter 180. In the long groove 184, a movement regulation pin 42a extending in a direction perpendicular to the axial direction of the shaft 24 is fixed to the pipe 42 of the shaft 24. Thus, the long groove 184 of the cutter 180 moves along the movement regulation pin 42a. Therefore, the cutter 180 moves straight. At this point, the cutter 180 is disposed in the cutter guiding grooves (channels, fluid discharge grooves) 172, 174 of the first and second holding members 52, 54.

The locking portions 184a, 184b, 184c to control the movement of the cutter 180 by locking the movement regulation pin 42a are formed, for example, at three locations of one end, the other end, and therebetween. The sensor 185 capable of recognizing the position of the movement regulation pin 42a and also recognizing the direction of movement of the movement regulation pin 42a is disposed in the long groove 184 of the cutter 180. Various kinds of sensors such as a sensor using light and a contact type sensor are used as the sensor 185. Thus, it becomes possible to recognize that the cutting edge 180a of the cutter 180 is contained in the shaft 24 when the movement regulation pin 42a is positioned in the locking portion 184a at the one end (tip end) of the long groove 184 and the cutting edge 180a of the cutter 180 is disposed in the cutter guiding grooves 172, 174 through the tip end of the shaft 24 when the movement regulation pin 42a is positioned at the other end (rear end) 184b. Therefore, the second detector 107 can recognize the position of the cutting edge 180a of the cutter 180 with respect to the shaft 24 and a treatment portion 26 through the sensor 185 and can easily determine whether the cutting edge 180a of the cutter 180 is in a position to cut body tissues.

The pipe 42 and a sheath 44 of the shaft 24 of the energy treatment device 12 shown in FIGS. 15A and 15B include fluid discharge ports 186, 188 through which a fluid such as a steam (gas) or liquid (tissue fluid) described later is discharged formed respectively. These fluid discharge ports 186, 188 are formed on the rear end side of the shaft 24.

Though not shown, a connection mouthpiece is suitably provided on the outer circumferential surface of the fluid discharge port 188 of the sheath 44. At this point, the fluid described later is discharged through the cutter guiding grooves 172, 174, the fluid discharge port 186 of the pipe 42 of the shaft 24, the fluid discharge port 188 of the sheath 44 of the shaft 24, and the connection mouthpiece. In this case, a fluid such as a steam and liquid released from body tissues L1, L2 can easily be discharged from the fluid discharge ports 186, 188 by sucking from inside the connection mouthpiece.

The fluid discharge ports 186, 188 are suitably provided in the shaft 24, but may also be suitably provided in the handle 22.

As shown in FIGS. 14A to 14C, first fluid conduits 162, 164 (described simply as the fluid conduits 162, 164 in the second embodiment) are disposed on the main bodies 62, 72 of the first and second holding members 52, 54, which has been described in the second embodiment and a description thereof is omitted.

As shown in FIG. 14B, second fluid conduits 192, 194 having insulating properties are disposed at edges of the cutter guiding grooves 172, 174. The second fluid conduit 192 is connected to, for example, a duct 64a of the base 64 of the first holding member 52. Similarly, the other second fluid conduit 194 is connected to, for example, a duct 74a of the base 74 of the second holding member 54.

The second fluid conduits 192, 194 each have a plurality of openings (join condition maintenance assistance portions) 192a, 194a formed at suitable intervals. The openings 192a, 194a of the fluid conduits 192, 194 are oriented toward the same second fluid conduits 192, 194 opposite to each other across the cutter 180.

Incidentally, the second fluid conduits 192, 194 may each be a pair or respective individual conduit bents in a U shape.

Figure 16:
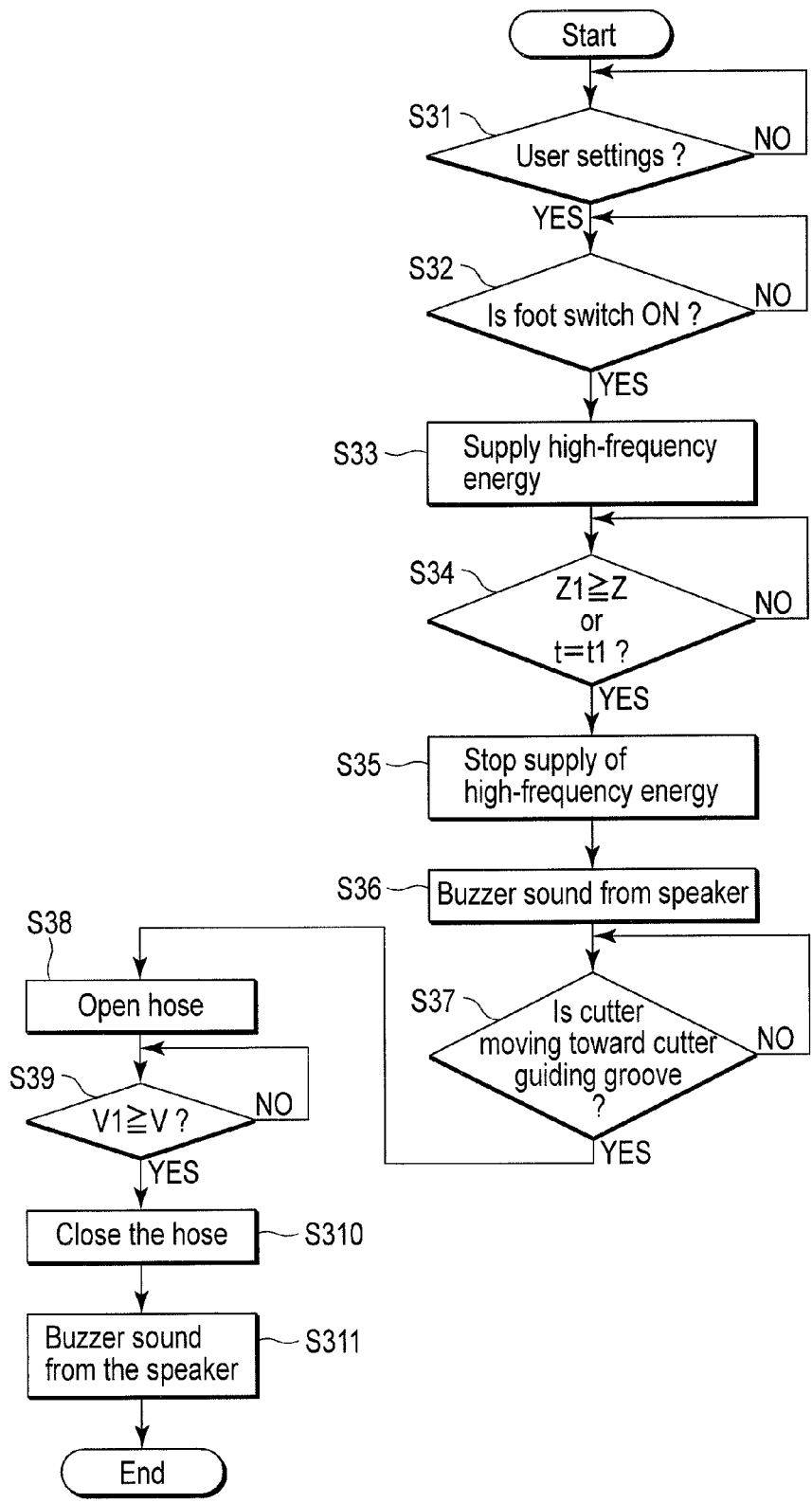
FIG. 16 is a flow chart showing the state of control of the medical treatment system exercised by an energy source, a foot switch, and a fluid source when body tissues are joined and the outer circumference of the joined body tissue is coated by using the medical treatment system according to the third embodiment.

Next, the action of a medical treatment system 10 according to the present embodiment will be described using FIG. 16.

As described in the first embodiment, a fluid (auxiliary joining agent) with which a joined body tissue $L_T$ obtained after joining the body tissues L1, L2 is coated is put into a fluid reservoir 122 of a fluid source 18. A hose 18a connected to the fluid reservoir 122 is closed by a flow rate adjustment mechanism 134 so that an adhesive should not flow toward the energy treatment device 12.

The operator operates a display unit 108 of the energy source 14 in advance to set output conditions for the medical treatment system 10 (S31). The operator checks the output (set power Pset [W]) from a high-frequency energy output portion 104, a threshold Z1 [Ω] of an impedance Z by the detector 106, an energy supply time t1 [sec] and the like through the display unit 108. If the output from the high-frequency energy output portion 104 or the threshold Z1 of the impedance Z by the detector 106 should be set to a different value, the operator sets the value as desired and checks the value through the display unit 108. The operator also sets a flow rate V1 passed from the fluid reservoir 122 to the energy treatment device 12 through the hose 18a.

As shown in FIG. 15A, the treatment portion 26 and the shaft 24 of the surgical treatment device 12 are inserted into the abdominal cavity through, for example, the abdominal wall while the second holding member 54 is closed with respect to the first holding member 52. To hold the body tissues L1, L2 to be treated by the first and second holding members 52, 54, the operator operates the treatment portion opening/closing knob 32 of the handle 22 to hold the body tissues L1, L2 to be treated between the first and second holding members 52, 54.

The operator operates the pedal of the foot switch 16 while the body tissues L1, L2 are held between the first and second holding members 52, 54. A signal is input into the first controller 102 from the foot switch 16 and the first controller 102 of the energy source 14 determines whether the switch 16 is changed to ON by the pedal thereof pressed through the operation of the operator (S32).

If the first controller 102 determines that the switch 16 is changed to ON by the pedal thereof pressed, a signal is input into the high-frequency energy output portion 104 from the first controller 102. The high-frequency energy output portion 104 supplies energy to the body tissues L1, L2 between the high-frequency electrodes 92, 94 through electrical connection lines 28a, 28b (S33). Then, a high-frequency current is passed to the body tissues L1, L2 between the high-frequency electrodes 92, 94. Thus, an inner portion of the body tissues L1, L2 is denatured (the body tissues L1, L2 are cauterized) while the body tissues L1, L2 are heated and dehydrated and contact surfaces C1, C2 of body tissues L1, L2 are joined to form a joined portion C. The first controller 102 determines whether the impedance Z has reached the threshold Z1 (S34) and stops the supply of the high-frequency energy when the impedance Z reaches the threshold Z1 (S35).

Then, a buzzer sound (first buzzer sound) to tell the end of conjugation treatment of the body tissues L1, L2 using high-frequency energy is emitted from a speaker 110 (S36).

Next, a medical doctor checks the first buzzer sound and then operates the cutter driving knob 34 shown in FIG. 12. That is, the medical doctor advances the cutter 180 along the cutter guiding grooves 172, 174 from the states shown in FIGS. 15A and 15B. As the cutter 180 advances, a region denatured and joined by the high-frequency electrodes 92, 94 will be cut. At this point, the sensor 185 detects, for example, relative positions of the locking portions 184a, 184b, 184c with respect to the movement regulation pin 42a and conveys the detected relative positions to the second detector 107. The second detector 107 recognizes the position and direction of movement of the cutter 180 with respect to the shaft 24 and the treatment portion 26 (S37).

If the direction of movement of the cutter 180 detected by the second detector 107 is recognized as a direction to cut the body tissue $L_T$, the first controller 102 delivers a signal to a second controller 132 to cause the flow rate adjustment mechanism 134 to operate so that the hose 18a is opened (S38).

Thus, after an adhesive passes through the hose 18a, the adhesive is oozed out from openings 162a, 164a of the fluid conduits 162, 164 of the first and second holding members 52, 54 and also oozed out from the openings 192a, 194a of the fluid conduits 192, 194. Then, the adhesive oozed out from the openings 162a, 164a of the fluid conduits 162, 164 is applied to a portion (exterior surface Sc of the joined body tissue $L_T$) of the high-frequency electrodes 92, 94 with which the adhesive comes into contact and the adhesive oozed out from the openings 192a, 194a of the fluid conduits 192, 194 is applied to the side face of the cutter 180. Thus, when the body tissue $L_T$ is cut, the adhesive is applied to a cut surface S of the body tissue $L_T$ by the cutter 180 by the side face of the cutter 180 brought into contact with the cut surface S of the body tissue $L_T$.

The first controller 102 determines whether a predetermined flow rate of adhesive has passed through the hose 18a (S39) and, if the predetermined flow rate of adhesive has passed, causes the flow rate adjustment mechanism 134 to operate to close the hose 18a (S310).

Then, a buzzer sound (second buzzer sound) to tell the end of application of the adhesive is emitted from the speaker 110 (S311).

The medical doctor releases the pedal of the foot switch 16 after recognizing the second buzzer sound from the speaker 110 and also operates the treatment portion opening/closing knob 32 of the handle 22 to release the body tissue $L_T$. At this point, as shown in FIG. 17, the body tissues L1, L2 are joined by the joined portion C and cut by the cut surface S. The surface Sc of the joined portion C and the cut surface S are coated after an adhesive is applied thereto.

According to the present embodiment, as described above, the following effect is achieved.

A fluid such as blood arising from the body tissues L1, L2 during treatment can be put into the cutter guiding grooves 172, 174. Then, the fluid put into the cutter guiding grooves 172, 174 can be led to outside the energy treatment device 12b from the fluid discharge ports 186, 188 formed in the pipe 42 of the shaft 24 and the sheath 44. Thus, fluid can be prevented from remaining on a joint surface of the joined portion C of the body tissues L1, L2 as much as possible so that conjugation treatment of the body tissues L1, L2 can be quickened. Therefore, a sequence of the treatment to join the body tissues L1, L2 and to coat the joined portion C can be carried out more efficiently.

Moreover, fluid can be prevented from seeping through into the joined portion C of the body tissue $L_T$ because not only the outer circumferential surface of the body tissue $L_T$ to be joined can be coated with an adhesive, but also the adhesive can be applied to the cut surface S of the body tissue $L_T$ for coating of the joint surface.

Though, as described above, the hose 18a may be opened to allow an adhesive to flow while the cutter 180 is moving, and the hose 18a may also be opened after the movement regulation pin 42a of the pipe 42 reaches the other end 184b from the one end 184a of the long groove 184 of the cutter 180 through the intermediate portion 184c. In this case, the body tissue $L_T$ has already been cut by the cutting edge 180a of the cutter 180 (the cut surface S has been formed). Then, the adhesive is passed until the movement regulation pin 42a of the pipe 42 reaches the one end 184a from the other end 184b of the long groove 184 of the cutter 180 through the intermediate portion 184c. Then, when the cutting edge 180a of the cutter 180 is drawn into the shaft 24 from the cutter guiding grooves 172, 174 of the first and second holding members 52, 54, a space is formed by the cut surfaces S of the body tissue $L_T$. If the adhesive is oozed out from the openings 192a, 194a, the adhesive infiltrates to between the cut surfaces S. Since the movement of the movement regulation pin 42a of the pipe 42 between the one end 184a and the other end 184b of the long groove 184 of the cutter 180 can be detected by the sensor 185, the spatial relationship between the body tissue $L_T$ to be joined and the cutter 180 can easily be grasped. Thus, the timing to close the hose 18a by the flow rate adjustment mechanism 134 can also be set suitably.

The present embodiment has been described by taking a buzzer sound as a sound emitted from the speaker 110, but treatment content or treatment procedures may be told in speech. It is preferable to make each sound easily recognizable to know what kind of treatment is completed, like the first buzzer sound and the second buzzer sound in the embodiment, which are considerably different.

In the present embodiment, a case when the cutter 180 is manually operated by the cutter driving knob 34 has been described, meanwhile, it is also preferable to cut the body tissue $L_T$ by automatically causing the cutter 180 to operate without operating the cutter driving knob 34 after the body tissues L1, L2 are treated for conjugation by high-frequency energy. That is, a sequence of treatment from the start of treatment using high-frequency energy to join the body tissues L1, L2 to the end of treatment to coat the joined body tissue $L_T$ may automatically be carried out.

Fourth Embodiment

Next, the fourth embodiment will be described using FIGS. 18A to 20. The present embodiment is a modification of the first embodiment and the same reference numerals are attached to the same members as those described in the first embodiment or members achieving the same action as the action of those in the first embodiment and a detailed description thereof is omitted.

As described in the first embodiment, a main body 62 of a first holding member 52 has, as shown in FIGS. 17A to 17C, a recess 62b formed therein. A first high-frequency electrode 92 is disposed on the main body 62 of the first holding member 52. A plurality of projections (a join condition maintenance assistance portion) 202 is formed toward a second holding member 54 in a portion of the first high-frequency electrode 92 on the recess 62b of the main body 62 of the first holding member 52. The projection 202 is formed to a suitable length so as to form a hole P shown in FIG. 20 in body tissues L1, L2. The projection 202 does not necessarily need to pass through the body tissues L1, L2 and the tip end (far end with respect to the first high-frequency electrode 92) of the projection 202 is suitably positioned closer to a second high-frequency electrode 94 than contact surfaces C1, C2 of the body tissues L1, L2.

Figure 18A:
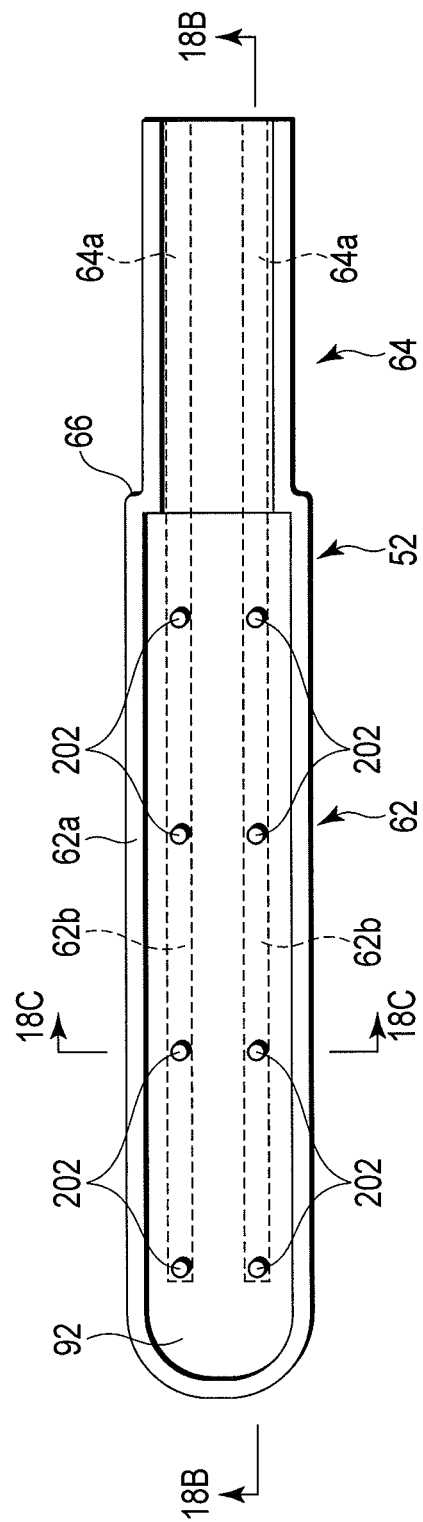
FIG. 18A is a rough plan view viewed from an arrow 18A direction in FIGS. 18B and 18C, and shows a first holding member of a treatment portion of an energy treatment device of a medical treatment system according to a fourth embodiment.
Figure 18B:
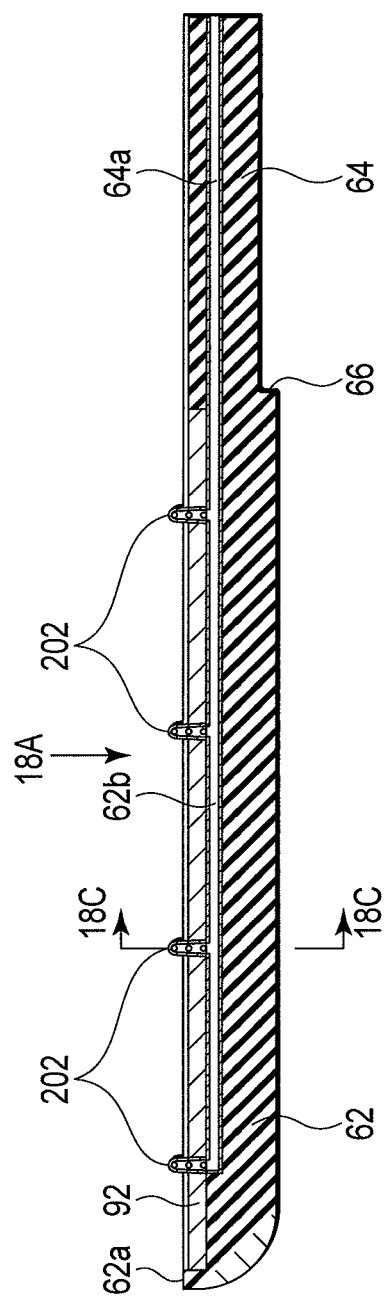
FIG. 18B is a rough longitudinal sectional view along a 18B-18B line in FIGS. 18A and 18C, and shows the first holding member of the treatment portion of the energy treatment device of the medical treatment system according to the fourth embodiment.
Figure 18C:
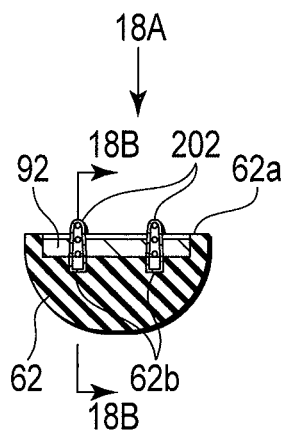
FIG. 18C is a rough transverse sectional view along a 18C-18C line in FIGS. 18A and 18B, and shows the first holding member of the treatment portion of the energy treatment device of the medical treatment system according to the fourth embodiment.
Figure 18D:
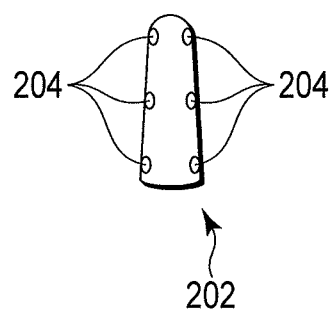
FIG. 18D is a rough perspective view showing a projection disposed on a high-frequency electrode of the first holding member of the treatment portion of the energy treatment device of the medical treatment system according to the fourth embodiment.

As shown in FIG. 18D, each of the projections 202 has one or a plurality of openings 204 formed therein. The plurality of openings 204 is preferably formed. The projection 202 is communicatively connected to the recess 62b and a fluid (conjugation adjunct) such as an adhesive can be oozed out through the recess 62b.

Figure 19A:
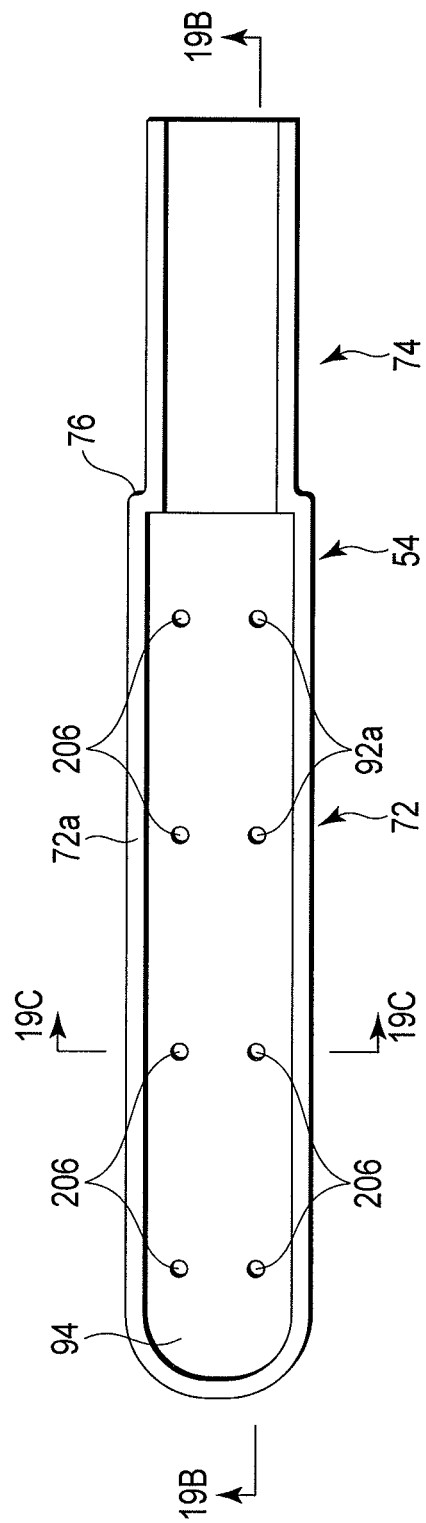
FIG. 19A is a rough plan view viewed from an arrow 19A direction in FIGS. 19B and 19C, and shows a second holding member of the treatment portion of the energy treatment device of the medical treatment system according to the fourth embodiment.
Figure 20:
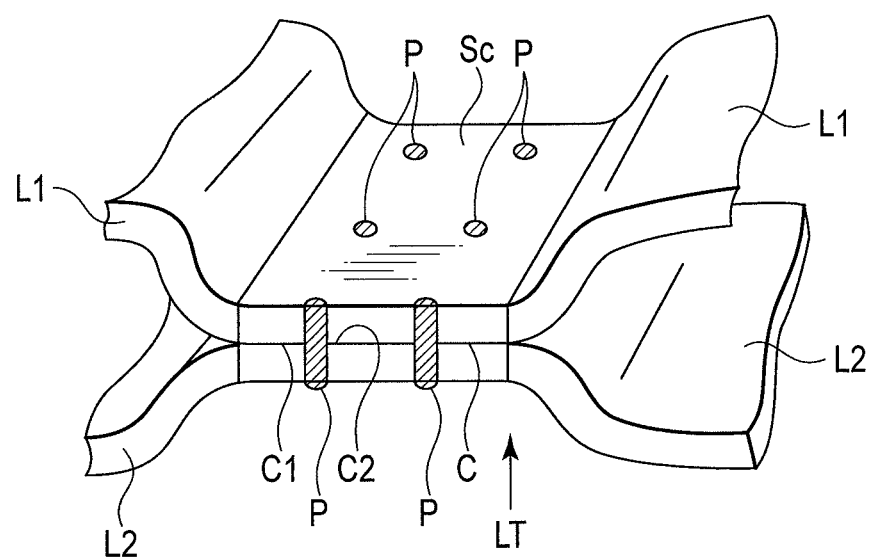
FIG. 20 is a rough perspective view showing the state of body tissues immediately after being treated by using the energy treatment device of the medical treatment system according to the fourth embodiment.

As shown in FIGS. 19A to 19C, a main body 72 of the second holding member 54 and the high-frequency electrode 94 have recesses (a join condition maintenance assistance portion) 206 formed therein. Each of the recesses 206 is formed so as to accommodate the projection 202 disposed on the first holding member 52 and projecting from the high-frequency electrode 92.

The surface of the high-frequency electrodes 92, 94 is positioned lower than edges 62a, 72a of the main bodies 62, 72 of the first and second holding members 52, 54. The length of the projection 202 of the first high-frequency electrode 92 is formed to a height that does not come into contact with the recess 206 of the second holding member 54. Thus, the first high-frequency electrode 92 and the second high-frequency electrode 94 are formed so as not to come into contact with each other even if the projection 202 of the first high-frequency electrode 92 is disposed in the recess 206 of the second high-frequency electrode 94.

Next, the action of a medical treatment system 10 according to the present embodiment will be described using FIG. 6.

Like in the first embodiment, the body tissues L1, L2 to be joined are held. In this case, the projections 202 are disposed on the high-frequency electrode 92 disposed on the first holding member 52 and thus, the projections 202 form the holes P by passing through the body tissues L1, L2 and also are accommodated in the recesses 206 disposed on the second holding member 54 and the high-frequency electrode 94.

In this state, the two body tissues L1, L2 are joined by high-frequency energy output from the high-frequency electrodes 92, 94 disposed on the first and second holding members 52, 54. At this point, the projections 202 provided on the high-frequency electrode 92 disposed on the first holding member 52 maintain a state of passing through the body tissues L1, L2 (state disposed in the hole P).

In this case, the projections 202 are disposed inside the body tissues L1, L2 and power is passed through body tissues between the projections 202 and the second high-frequency electrode 94 and therefore, treatment of the body tissues L1, L2 using high-frequency energy can be carried out efficiently.

After an impedance Z reaches a threshold Z1, a flow rate adjustment mechanism 134 is released to allow an adhesive to flow from a fluid reservoir 122 through a hose 18*a*. In this case, a duct 64*a* is provided in a base 64 of the first holding member 52 and the recess 62*b* is provided in the main body 62 and thus, an adhesive is oozed out from the openings 204 of the projections 202. In this case, the projections 202 are disposed in the holes P by passing through the joined body tissue $L_T$ and thus, a portion of the adhesive oozed out from the openings 204 is applied to the joined portion C of the body tissue $L_T$. A portion of the adhesive penetrates directly through the joint surface of the joined portion C. The adhesive has, in addition to the adhesive action, the coating action and thus, moisture can be prevented from infiltrating into the joined portion C and also the joined state can be maintained.

When a sequence of the treatment of the conjugation of the body tissues L1, L2 by high-frequency energy and the application of the adhesive to the joined portion C is completed, a sound such as a buzzer sound is emitted from a speaker 110 to let the medical doctor know completion of the treatment.

According to the present embodiment, as described above, the following effect is achieved.

Because Joule heat can be generated not only in the body tissues L1, L2 between the high-frequency electrodes 92, 94, but also in the body tissues L1, L2 between the projections 202 passing through the body tissues L1, L2 and the high-frequency electrode 94 and thus, it can be made easier for energy to penetrate the body tissues L1, L2 even if the body tissues L1, L2 are thick (if it is difficult for high-frequency energy to penetrate the body tissues L1, L2).

Because a fluid such as an adhesive can directly be supplied into the joined body tissue $L_T$ such as the joined portion C of the body tissues L1, L2 to be joined for infiltration by the projections 202 provided on the high-frequency electrode 92, the conjugation of the joined portion C can be made more reliable and also the coating action of the adhesive can be extended to the neighborhood of the joined portion C including the joint surface.

In the present embodiment, a case when the holes P are formed in the body tissues L1, L2 by the projections 202 of the first holding member 52 when body tissues are held by the first and second holding members 52, 54 has been described. However, when the body tissues L1, L2 are held by the first and second holding members 52, 54, the holes P do not necessarily need to be formed by the projections 202. That is, when the body tissues L1, L2 are held by the first and second holding members 52, 54, the projections 202 of the first holding member 52 may be provided in such a way that the body tissue L2 is pressed against the recesses 206 of the second holding member 54. Also in this case, with the supply of high-frequency energy to the body tissues L1, L2 between the first and second high-frequency electrodes 92, 94, the holes P will be formed in the body tissues L1, L2, that is, the projections 202 will be disposed in the holes P.

The projections 202 of the high-frequency electrode 92 of the first holding member 52 may be formed as a different body such as a hardening resin material having insulating properties. In this case, the projections 202 are permitted to come into contact with the high-frequency electrode 94 of the second holding member 54.

Fifth Embodiment

Next, the fifth embodiment will be described using FIGS. 21A to 23. The present embodiment is a modification of the third embodiment and the same reference numerals are attached to the same members as those described in the third embodiment or members achieving the same action as the action of those in the third embodiment and a detailed description thereof is omitted.

As shown in FIGS. 21A and 21B, recesses 62*b*, 72*b* (see FIGS. 4A to 4C) and ducts 64*a*, 74*a* (see FIGS. 4A to 4C) are removed from main bodies 62, 72 of first and second holding members 52, 54 in the present embodiment.

Figure 22A:
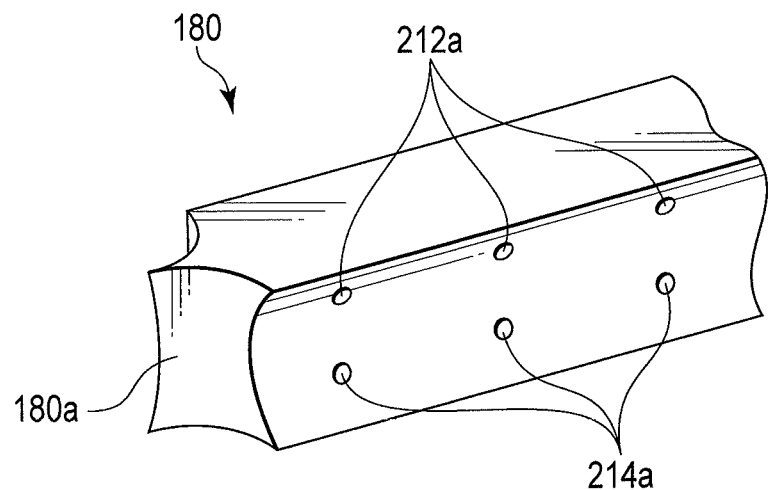
FIG. 22A is a rough perspective view showing a tip portion containing a cutting portion of a cutter disposed on the energy treatment device of the medical treatment system according to the fifth embodiment.
Figure 22B:
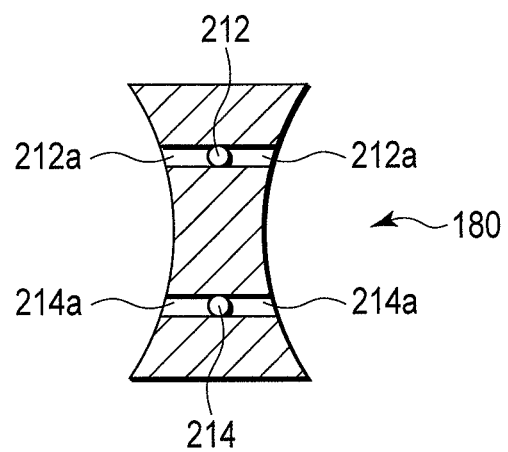
FIG. 22B is a rough transverse sectional view showing the cutter disposed on the energy treatment device of the medical treatment system according to the fifth embodiment.
Figure 22C:
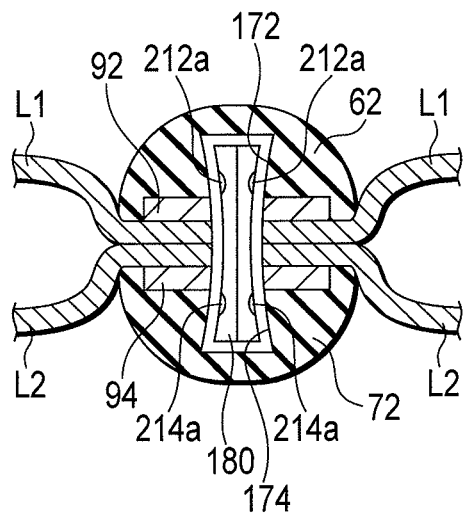
FIG. 22C is a rough transverse sectional view showing the state of treating and conjugating body tissues while being held by the treatment portion of the energy treatment device of the medical treatment system and cutting the body tissues by the cutter according to the fifth embodiment.
Figure 22D:
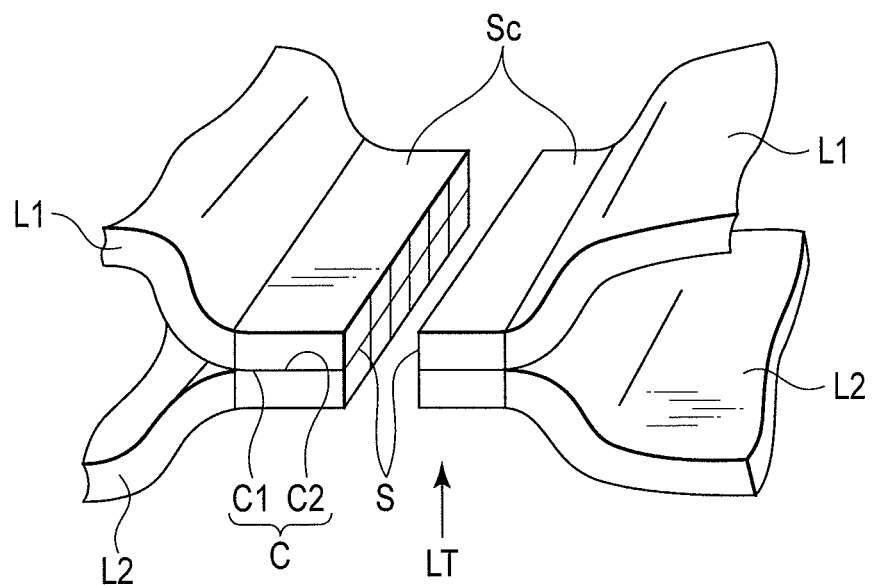
FIG. 22D is a rough perspective view showing the state of body tissues immediately after being treated by using the energy treatment device of the medical treatment system according to the fifth embodiment.

A cutter 180 shown in FIG. 22A has a cutting edge 180*a* at the tip end thereof. The cutter 180 has ducts 212, 214 formed, for example, shown in the upper and lower parts in FIG. 22B, inside along the longitudinal direction of the cutter 180. The ducts 212, 214 formed inside the cutter 180 are connected to a hose 18*a* through an inner portion of a driving rod 182. As shown in FIGS. 22A and 22B, a plurality of openings (conjugation maintenance assistance portions) 212*a*, 214*a* are formed at suitable intervals along the longitudinal direction of the cutter 180 on the side face of the cutter 180. These openings 212*a*, 214*a* are communicatively connected to the ducts 212, 214. Thus, a fluid infiltration prevention substance (conjugation adjunct) to a body tissue $L_T$ such as an adhesive can be discharged from the openings 212*a*, 214*a* through the ducts 212, 214.

Also in the present embodiment, a case when the cutter 180 automatically operates at an appropriate time during a sequence of treatment is described.

Figure 23:
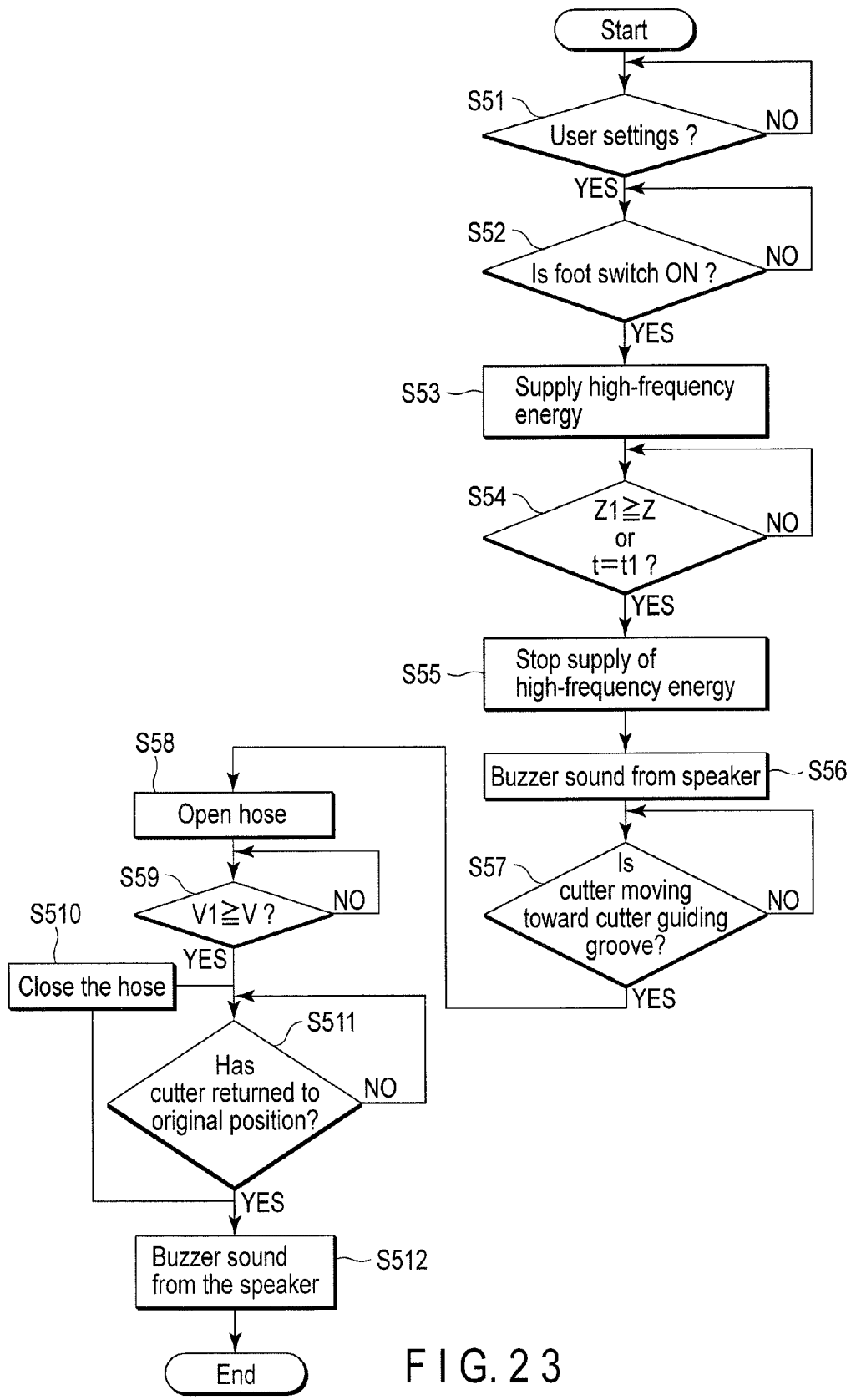
FIG. 23 is a flow chart showing the state of control of the medical treatment system exercised by an energy source, afoot switch, and a fluid source when body tissues are treated by using the medical treatment system according to the fifth embodiment.

Next, the action of a medical treatment system 10 according to the present embodiment will be described using FIG. 23.

As described in the first embodiment, contact surfaces C1, C2 of body tissues L1, L2 are joined by high-frequency energy emitted from high-frequency electrodes 92, 94 (S51 to S56).

Then, the cutter 180 is operated to cut the joined body tissue $L_T$ (S57). The hose 18a is opened by linking to the operation of the cutter 180 (S58). Thus, while the joined body tissue $L_T$ is cut, an adhesive is oozed out from the opening 212a of the cutter 180 to apply the adhesive to a cut surface S. That is, the adhesive oozed out from the opening 212a of the cutter 180 is applied as the body tissue $L_T$ is cut.

At this point, as shown in FIG. 22B, the openings 212a are formed in the upper and lower parts of the cutter 180 and if it is assumed that the body tissues L1, L2 have the same thickness, an adhesive is applied to a position deviating from the joint surface of a joined portion C. The applied adhesive flows in a suitable direction depending on orientations of the first and second holding members 52, 54 and thus, the adhesive is applied to the entire cut surface S by the cutter 180.

Incidentally, the adhesive is also applied to the surface of the body tissue $L_T$ in contact with the high-frequency electrodes 92, 94. Thus, the adhesive is applied to the entire exterior surface of the body tissue $L_T$.

If a predetermined flow rate of adhesive flows through the hose 18a, the hose 18a is closed (S510) and also the cutter 180 is returned to the original position thereof. Then, if the return of the cutter 180 to the original position thereof is recognized through a sensor 185 disposed in the cutter 180 (S511), a buzzer sound to tell the end of a sequence of treatment is emitted from a speaker 110 (S512).

Sixth Embodiment

Next, the sixth embodiment will be described using FIGS. 24A to 24D. The present embodiment is a modification of the fifth embodiment and the same reference numerals are attached to the same members as those described in the fifth embodiment or members achieving the same action as the action of those in the fifth embodiment and a detailed description thereof is omitted.

Figure 24A:
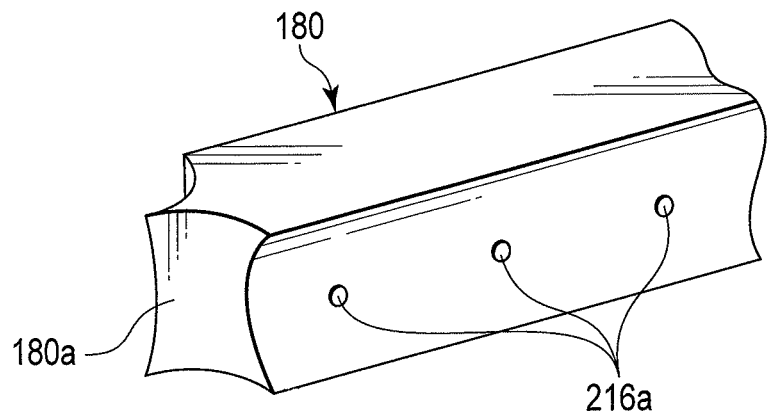
FIG. 24A is a rough perspective view showing a tip portion containing a cutting portion of a cutter disposed on an energy treatment device of a medical treatment system according to a sixth embodiment.
Figure 24B:
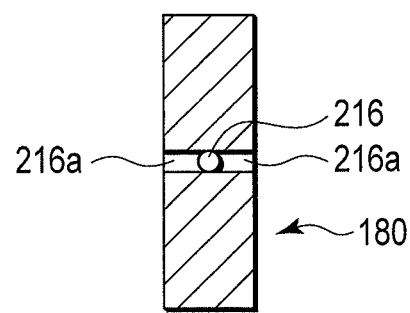
FIG. 24B is a rough transverse sectional view showing the cutter disposed on the energy treatment device of the medical treatment system according to the sixth embodiment.

As shown in FIG. 24B, a duct 216 is formed inside a cutter 180 along the longitudinal direction of the cutter 180. The duct 216 formed inside the cutter 180 is connected to a hose 18a through an inner portion of a driving rod 182. A plurality of openings (a conjugation maintenance assistance portion) 216a is formed in the center in a width direction on the side face of the cutter 180. Thus, a body tissue $L_T$ is cut and at the same time, an adhesive is applied to the neighborhood of the joint surface of a joined portion C. Therefore, the adhesive (conjugation adjunct) penetrates the joint surface of the joined portion C and is hardened. In this case, as shown in FIG. 24D, an increasing amount of adhesive penetrates with an adhesive being closer to the cut surface S and a decreasing amount of adhesive penetrates with an adhesive being further away from the cut surface S.

Seventh Embodiment

Next, the seventh embodiment will be described using FIGS. 25 to 30. The present embodiment is a modification of the first and fifth embodiments and the same reference numerals are attached to the same members as those described in the first and fifth embodiments or members achieving the same action as the action of those in the first and fifth embodiments and a detailed description thereof is omitted.

Figure 25:
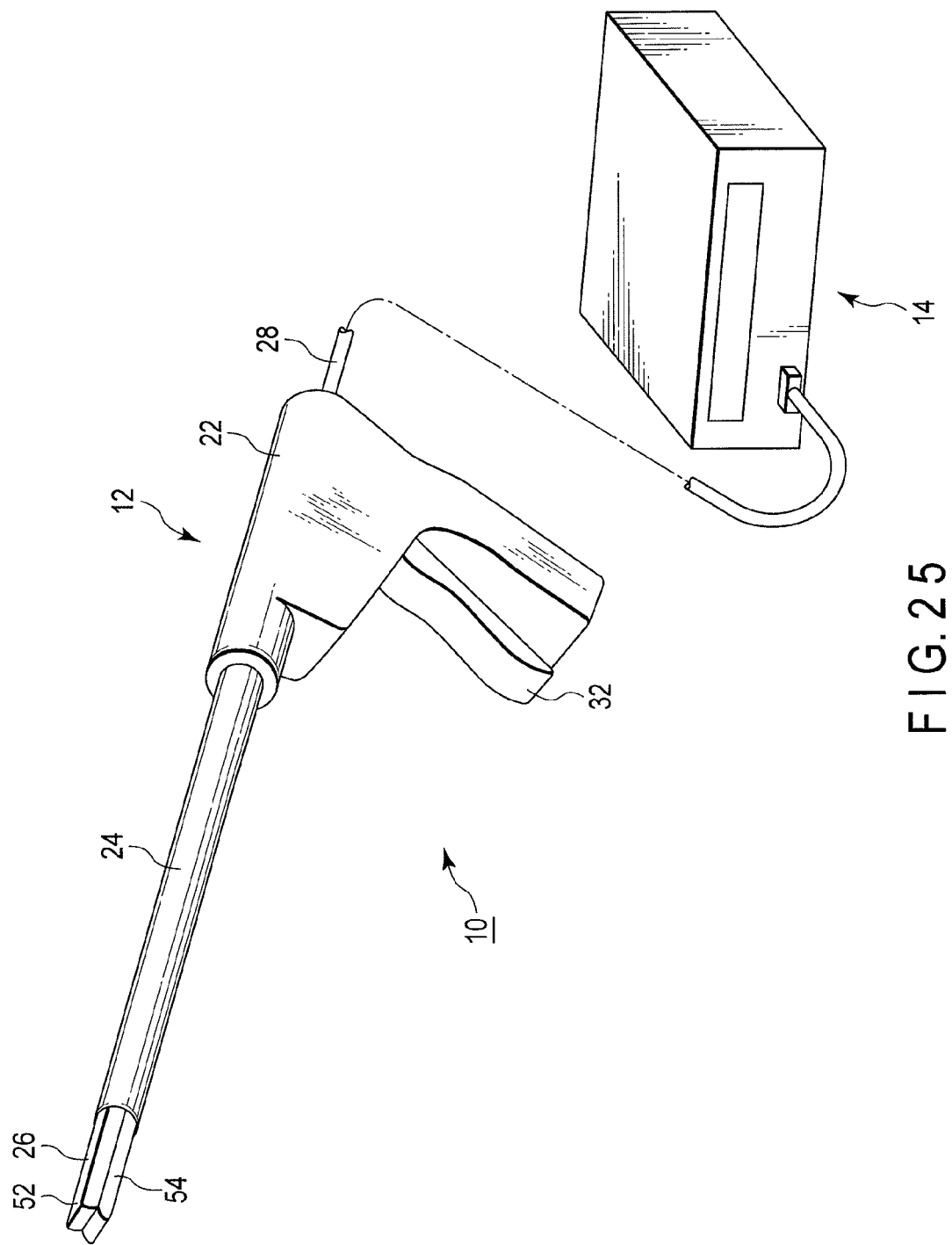
FIG. 25 is a schematic diagram showing a medical treatment system according to a seventh embodiment.

As shown in FIG. 25, a medical treatment system 10 according to the present embodiment includes an energy treatment device 12 and an energy source 14. Here, a case when a fluid source 18 is removed from the medical treatment system 10 will be described.

Figure 26A:
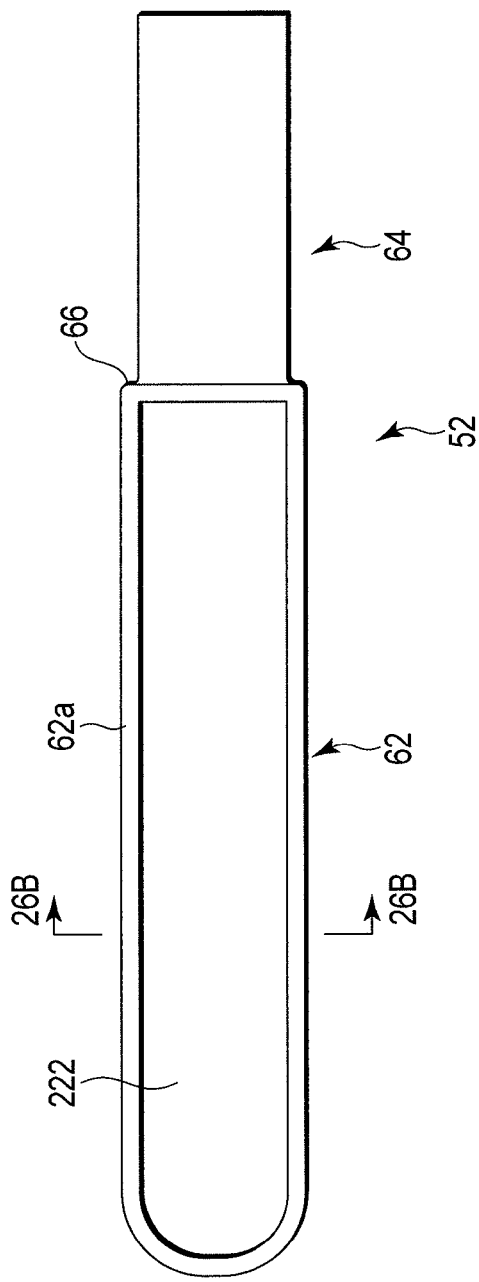
FIG. 26A is a rough plan view viewed from an arrow 26A direction in FIG. 26B, and shows a first holding member of a treatment portion of an energy treatment device of the medical treatment system according to the seventh embodiment.
Figure 26B:
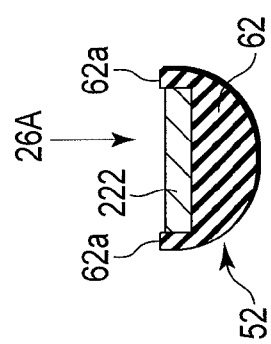
FIG. 26B is a rough transverse sectional view along a 26B-26B line in FIG. 26A, and shows the first holding member of the treatment portion of the energy treatment device of the medical treatment system according to the seventh embodiment.

As shown in FIGS. 26A and 26B, a plate-like heater (energy output portion) 222 is disposed on a main body 62 of a first holding member 52. The heater 222 is enclosed with a holding surface 62a of the main body 62. Though not shown, a plate-like heater (energy output portion) 232 is disposed on a main body 72 of a second holding member 54. The heater 232 is enclosed with a holding surface 72a of the main body 72.

Figure 27A:
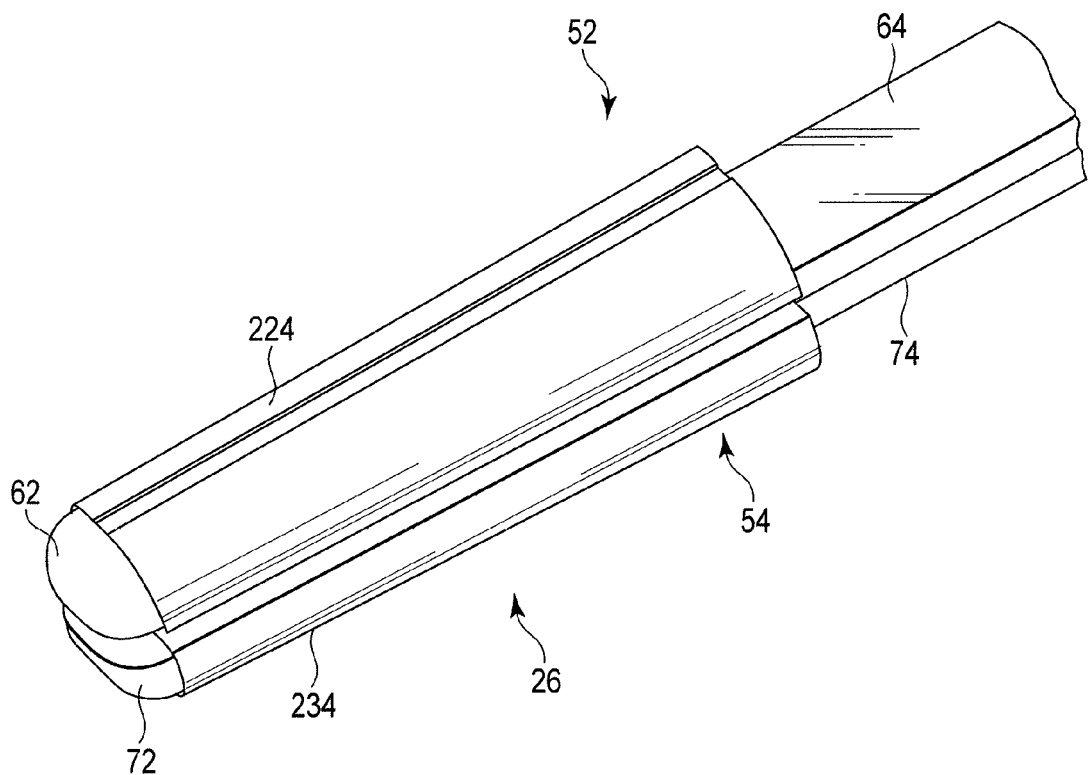
FIG. 27A is a rough perspective view showing the state in which a coating member is disposed on a main body of each of the first holding member and a second holding member of the treatment portion of the energy treatment device of the medical treatment system according to the seventh embodiment.
Figure 27B:
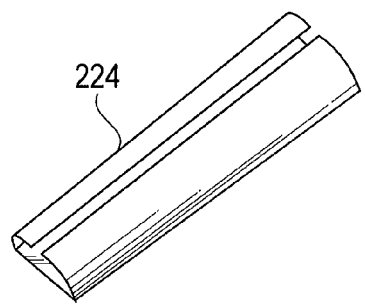
FIG. 27B is a rough perspective view showing the coating member disposed on the main body of the first holding member and the second holding member of the treatment portion of the energy treatment device of the medical treatment system according to the seventh embodiment.

As shown in FIG. 27A, a coating member (sheet-shaped member) 224 (see FIG. 27B) whose transverse section is formed in a C shape in advance is disposed on the outer circumference of the main body 62 of the first holding member 52.

As shown in FIGS. 28A to 28C, various types such as a nonporous sheet-shaped type, mesh-shaped type, or porous type of the coating member 224 are used for a portion thereof in contact with the heater 222. The coating member 224 contains a component of the conjugation adjunct described in the first embodiment. When the coating member 224 is heated to an appropriate temperature, a heated portion of the conjugation adjunct melts and the component of the conjugation adjunct is spread over the surface of body tissues and infiltrates the surface and when the coating member 224 is cooled, the conjugation adjunct is hardened in a state in which the conjugation adjunct spreads over and infiltrates the surface of body tissues. If the conjugation adjunct is hardened, as described in the first embodiment, an action to prevent fluid from penetrating the joint surface or the like described later from outside the body tissues is achieved.

Incidentally, the coating member 224 is suitably expandable at least in the circumferential direction (width direction perpendicular to the longitudinal direction of the main body 62 of the first holding member 52) before heating (for example, the nonporous sheet-shaped, mesh-shaped, or porous state). Then, when the coating member 224 is disposed on the main body 62 of the first holding member 52, the coating member 224 can be brought into close contact with the holding surface 62a of the main body 62 of the first holding member 52 and an exterior surface of the main body 62 separated from the second holding member 54.

The coating members (a join condition maintenance assistance portion) 224, 234 will be disposed between body tissues L1, L2 and the heaters 222, 232 when the body tissues L1, L2 are held by the main bodies 62, 72 of the first and second holding members 52, 54 and thus the coating members (a conjugation maintenance assistance portion) 224, 234 are pressed toward the heaters 222, 232 by the body tissues L1, L2. Therefore, when the body tissues L1, L2 are held by the first and second holding members 52, 54, the coating members 224, 234 are in contact with the heaters 222, 232.

Ends of the coating member 224 disposed on the first holding member 52 may be opposite to each other in positions of the main body 62 of the first holding member 52 separated from the main body 72 of the second holding member 54 or partially overlapped. The heater 232 and the coating member 234 are also disposed on the second holding member 54. In such a case, the heater 232 and the coating member 234 are suitably disposed on the same manner as in the first holding member 52.

Figure 29:
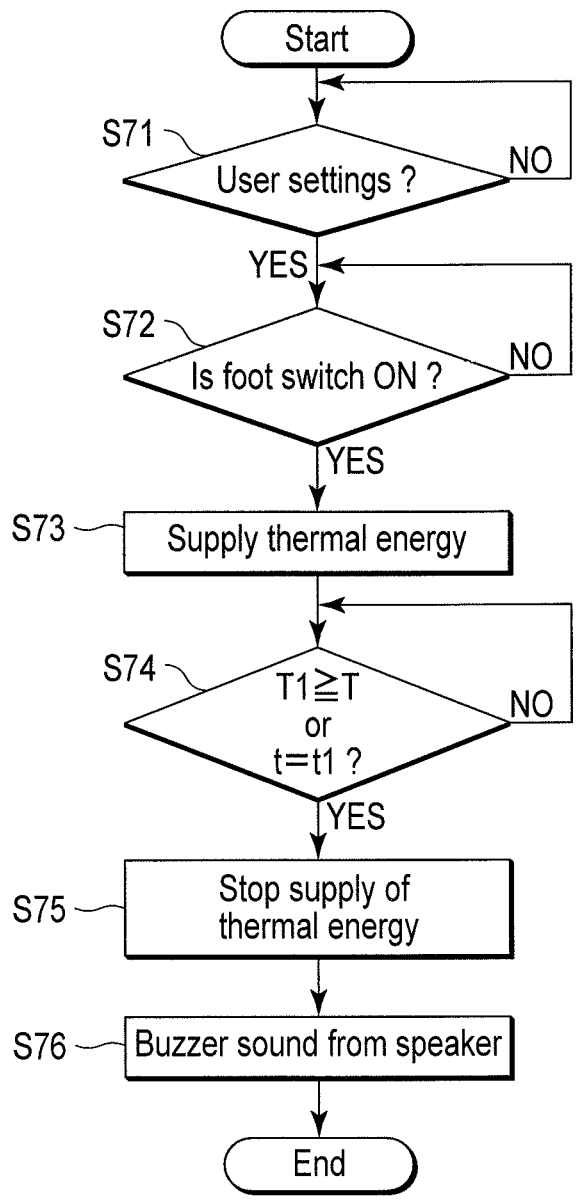
FIG. 29 is a flow chart showing the state of control of the medical treatment system exercised by an energy source, a foot switch, and a fluid source when body tissues are treated by using the medical treatment system according to the seventh embodiment.

Next, the action of a medical treatment system 10 according to the present embodiment will be described using FIG. 29.

First, a display unit 108 is operated to make various settings. For example, the maximum temperature of the heaters 222, 232, the output time of energy from a high-frequency energy output portion 104 to the heaters 222, 232, a threshold T1 of the end temperature of treatment of body tissues (here, the surface temperature of the body tissues L1, L2) are set (S71).

Then, the body tissues L1, L2 are held by the main bodies 62, 72 of the first and second holding members 52, 54 while the coating members 224, 234 are wound around the main bodies 62, 72 of the first and second holding members 52, 54, respectively. That is, the coating member 224 disposed on the first holding member 52 comes into contact with the surface of the body tissue L1 on the opposite side of the contact surface C1 coming into contact with the body tissue L2. The coating member 234 disposed on the second holding member 54 comes into contact with the surface of the body tissue L2 on the opposite side of the contact surface C2 coming into contact with the body tissue L1.

If the pedal of the foot switch 16 is pressed in this state (S72), energy is transmitted from the high-frequency energy output portion 104 to the heaters 222, 232 (S73) and the temperature of the heaters 222, 232 gradually rises (electric energy is converted into thermal energy). Then, a portion of the coating members 224, 234 in contact with the heaters 222, 232 melts due to thermal energy of the heaters 222, 232 and a fluid infiltration prevention material to the body tissue $L_T$ is applied to the exterior surface of the body tissues L1, L2. Also with the rise in temperature of the heaters 222, 232, heat of the heaters 222, 232 is extended to the body tissues L1, L2 to add heat to the body tissues L1, L2. Then, after an impedance Z is measured, a surface temperature T of the body tissues L1, L2 is measured or a predetermined time t1 passes (S74), the supply of energy from the high-frequency energy output portion 104 to the heaters 222, 232 is stopped (S75). Then, a buzzer sound that tells the end of a sequence of treatment is emitted from a speaker 110 (S76).

The substance that prevents wet from penetrating the body tissue $L_T$ is gradually hardened by, for example, being cooled due to stop of supply of energy. Then, the substance that prevents moisture from penetrating the body tissue $L_T$ is maintained in a state in which the joined body tissue $L_T$ is coated with the substance.

Incidentally, a portion of the coating members 224, 234 that is not in contact with the heaters 222, 232 preferably maintains the state of being disposed on the main bodies 62, 72 of the first and second holding members 52, 54. That is, the side of the coating member 224 disposed on the first holding member 52 separated from the holding surface 62a of the main body 62 with respect to the second holding member 54 maintains the state being disposed on the outer circumferential surface of the main body 62. Also, the side of the coating member 234 disposed on the second holding member 54 separated from the holding surface 72a of the main body 72 with respect to the first holding member 52 maintains the state being disposed on the outer circumferential surface of the main body 72.

If the porous coating members 224, 234 shown in FIG. 28B or the mesh-shaped coating members 224, 234 shown in FIG. 28C are used, instead of the heaters 222, 232, high-frequency electrodes 92, 94 can be used for treatment. If the porous coating members 224, 234 shown in FIG. 28B are used, a portion of the high-frequency electrodes 92, 94 comes into contact with the body tissues L1, L2. If the mesh-shaped coating members 224, 234 shown in FIG. 28C are used, a portion of the high-frequency electrodes 92, 94 comes into contact with the body tissues L1, L2. Therefore, when these porous or mesh-shaped coating members 224, 234 are used, any of the high-frequency electrodes 92, 94 or the heaters 222, 232 can be used.

On the other hand, the nonporous sheet-shaped coating members 224, 234 shown in FIG. 28A are used, the high-frequency electrodes 92, 94 do not come into contact with the body tissues L1, L2 and thus, in this case, it is preferable to use the heaters 222, 232. If the high-frequency electrodes 92, 94 can directly be brought into contact with the body tissues L1, L2 by providing holes in a portion of the nonporous sheet-shaped coating members 224, 234, as will be described below, treatment by high-frequency energy also becomes possible. Also, if the coating members 224, 234 are formed as an energizing member, as will be described below, treatment by high-frequency energy also becomes possible.

Next, the action of a medical treatment system 10 when the body tissues L1, L2 are treated using the high-frequency electrodes 92, 94, instead of the heaters 222, 232, will be described. Here, the porous coating members 224, 234 shown in FIG. 28B or the mesh-shaped coating members 224, 234 shown in FIG. 28C are used.

As shown in FIG. 27A, the body tissues L1, L2 are held by the main bodies 62, 72 of the first and second holding members 52, 54 in a state in which the coating members 224, 234 are wound around the main bodies 62, 72. At this point, the coating members 224, 234 are in contact with the exterior surface of the body tissues L1, L2 and because the coating members 224, 234 have holes, a portion of the high-frequency electrodes 92, 94 is also in contact with the exterior surface of the body tissues L1, L2. Thus, high-frequency energy is supplied from the high-frequency electrodes 92, 94 to the body tissues L1, L2 in a state in which the body tissues L1, L2 are held as described above.

A portion of the coating members 224, 234 in contact with the body tissues L1, L2 melts accompanying heating of the body tissues L1, L2 after energy is supplied to the body tissues L1, L2 from the high-frequency electrodes 92, 94. Then, the melted portion of the coating members 224, 234 spreads over the entire outer circumferential surface of the body tissues L1, L2 held by the main bodies 62, 72 of the first and second holding members 52, 54. That is, this is the same state as a state in which a fluid such as an adhesive is applied to the exterior surface of the body tissues L1, L2. Then, if the supply of energy to the high-frequency electrodes 92, 94 is stopped after the impedance Z reaches a predetermined threshold Z1, the temperature of the body tissue $L_T$ drops and also the substance that prevents fluid from infiltrating the body tissue $L_T$ is hardened.

At this point, a fluid such as an adhesive serves the role of preventing moisture from penetrating the joined body tissue $L_T$. Thus, the body tissues L1, L2 can maintain a state in which the body tissues L1, L2 are joined for a long time.

Figure 30:
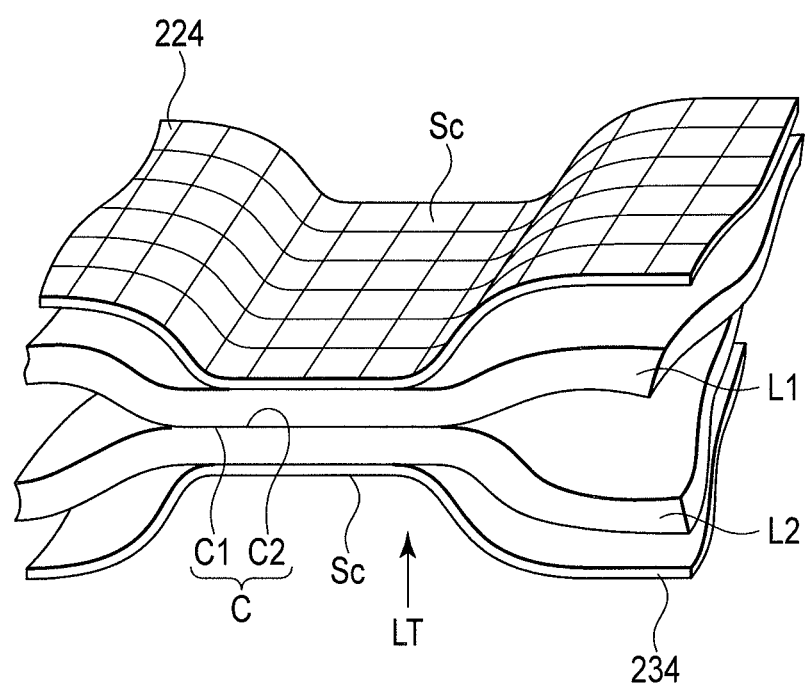
FIG. 30 is a rough perspective view showing the state in which the coating member is disposed on a surface of body tissues when the body tissues are treated by using the energy treatment device of the medical treatment system according to the seventh embodiment.
Figure 33:
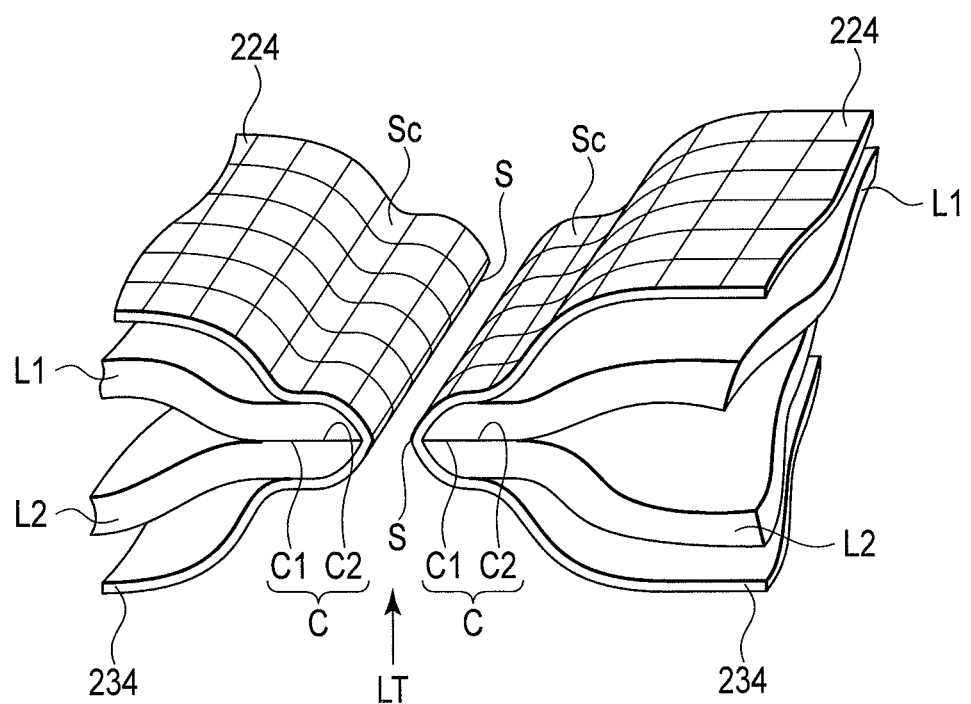
FIG. 33 is a rough perspective view showing the state in which a coating member is disposed on the surface of body tissues when the body tissues are treated by using the energy treatment device of the medical treatment system according to the eighth embodiment.

FIG. 30 shows a schematic diagram in which the body tissues L1, L2 are coated with the coating members 224, 234. If the body tissues L1, L2 are treated by using thermal energy or high-frequency energy in such a state, the outer surface of the joined body tissue $L_T$ is in a state of being coated with the substance that prevents fluid from infiltrating the body tissue $L_T$.

Eight Embodiment

Next, the eighth embodiment will be described using FIGS. 31A to 35. The present embodiment is a modification of the seventh embodiment and the same reference numerals are attached to the same members as those described in the seventh embodiment or members achieving the same action as the action of those in the seventh embodiment and a detailed description thereof is omitted.

As shown in FIGS. 31A and 31B, first and second holding members 52, 54 include cutter guiding grooves 172, 174 formed therein. A cutter 180 (see FIGS. 15A and 15B) having a long groove 184 can be loaded into or unloaded from the cutter guiding grooves 172, 174.

A plurality of heaters (an energy output portion) 242 is disposed on a back surface of a high-frequency electrode 92 disposed on a main body 62 of the first holding member 52. Similarly, though not shown, a plurality of heaters (an energy output portion) 252 is disposed on the back surface of a high-frequency electrode 94 disposed on a main body 72 of the second holding member 54. The heaters 242, 252 can be controlled by a high-frequency energy output portion 104. That is, the high-frequency energy output portion 104 can supply energy not only to the high-frequency electrodes 92, 94, but also to the heaters 242, 252. Incidentally, the high-frequency energy output portion 104 may be made to be capable of selectively or simultaneously supplying energy to both the high-frequency electrodes 92, 94 and the heaters 242, 252.

The high-frequency electrodes 92, 94 are each formed from a material having a high thermal conductivity and thus, if the heaters 242, 252 are heated by supplying energy from the high-frequency energy output portion 104 to the heaters 242, 252, heat is conducted from the heaters 242, 252 to the high-frequency electrodes 92, 94. The heat conducted to the high-frequency electrodes 92, 94 is spread, for example, concentrically from the heaters 242, 252.

Next, the action of a medical treatment system 10 according to the present embodiment will be described using FIG. 32. Here, it is assumed that the nonporous sheet-shaped coating members 224, 234 containing a conjugation adjunct are used.

The amount of output from the high-frequency energy output portion 104 to the heaters 242, 252 and the output time are suitably set (S181). It is assumed here that the output time to the heaters 242, 252 is 10 sec.

If the pedal of the foot switch 16 is pressed (S182), energy is supplied from the high-frequency energy output portion 104 to the heaters 242, 252 so that the heaters 242, 252 are heated (S183). It is determined whether 10 sec has passed after the supply of energy is started (S184). After energy is output from the high-frequency energy output portion 104 to the heaters 242, 252 for 10 sec, the supply of energy to the heaters 242, 252 is stopped (S185). Then, a buzzer sound is emitted from a speaker 110 to tell the stop of the supply of thermal energy and also to tell that a cutter 180 will operate (S186).

A portion of the nonporous sheet-shaped coating members 224, 234 in contact with the high-frequency electrodes 92, 94 is melted after heat from the heaters 242, 252 are conducted to the high-frequency electrodes 92, 94.

Then, the cutter 180 is advanced to the cutter guiding grooves to cut body tissues L1, L2 (S187). That is, a cut surface S of the body tissues L1, L2 is formed. Then, the cutter 180 is returned to the original position thereof (S188).

Then, energy is supplied from the high-frequency energy output portion 104 to the high-frequency electrodes 92, 94 (S189). If an impedance Z is determined to have reached a threshold Z1 (S1810), the output from the high-frequency energy output portion 104 to the high-frequency electrodes 92, 94 is stopped (S1811).

A buzzer sound is emitted from the speaker 110 to tell the stop of the supply of energy (S1812). Thus, a medical doctor or the like can make sure that a sequence of treatment has ended.

In the present embodiment, there is described a case when a sequence of treatment is carried out by combining both thermal energy by the heaters 242, 252 and high-frequency energy by the high-frequency electrodes 92, 94, but a sequence of treatment can be carried out using only thermal energy.

Next, the action (first action) of a medical treatment system 10 when the porous or mesh-shaped coating members 224, 234 containing a conjugation adjunct are used will be described using FIG. 34.

The amount of output of high-frequency energy or the like is set by operating a display unit 108 (S281). Then, the body tissues L1, L2 are held by the main bodies 62, 72 of the first and second holding members 52, 54 on which the coating members 224, 234 are disposed respectively. In this state, the pedal of the foot switch 16 is pressed (S282).

Energy is transmitted from the high-frequency energy output portion 104 to the high-frequency electrodes 92, 94 and a high-frequency current is passed through the body tissues L1, L2 (S283). When a high-frequency current is passed, the impedance Z drops from an initial value Z0 and then rises again (see FIG. 5A). When the impedance at the lowest point is Zmin and the next impedance measured after the impedance Zmin at the lowest point is Zmin+1, if the impedance Zmin+1 measured next is larger than the impedance Zmin at the lowest point and impedance Zmin+1 is smaller than the initial value Z0, the impedance Zmin at the lowest point can be determined (S284). If, as described above, the impedance Z is determined to rise again from the impedance Zmin at the lowest point, the supply of energy from the high-frequency energy output portion 104 is stopped (S285). At this point, a buzzer sound is emitted from the speaker 110 to tell the stop of the supply of high-frequency energy to the body tissues L1, L2 and also to tell that the cutter 108 will be operated (S286).

The cutter 180 slowly advances automatically along the cutter guiding grooves 172, 174 of the first and second holding members 52, 54 to cut the body tissues L1, L2 (S287) and returns to the original position thereof (S288). In this case, under control of a moving rate, position or the like, the cutter 180 moves from a state in which a movement regulation pin 42a of a shaft 24 is positioned in a locking portion 184a on the distal end side of a long groove 184 of the cutter 180 to a locking portion 184b on the proximal end side of the long groove 184, and moves again to be disposed in the locking portion 184a (original position) on the distal end side of the long groove 184.

Then, energy is supplied from the high-frequency energy output portion 104 to the heaters 242, 252 so that the heaters 242, 252 are heated (S289). When 10 sec passes after the supply of energy from the high-frequency energy output portion 104 to the heaters 242, 252 is started (S2810), the supply of energy is stopped (S2811).

The heaters 242, 252 conduct heat to the high-frequency electrodes 92, 94, and the high-frequency electrodes 92, 94 conduct the heat directly to body tissues, and thus, the body tissues (proteins) are integrally denatured and also fluid acting as a hindrance factor of linkage of proteins is removed.

Then, a buzzer sound is emitted from the speaker 110 to tell the end of a sequence of treatment (S2812).

Incidentally, the coating members 224, 234 may be melted by generating heat into the body tissues L1, L2 using high-frequency energy or by directly applying heat using the heaters 242, 252.

Next, the action (second action) of the medical treatment system 10 when the porous or mesh-shaped coating members 224, 234 are used will be described using FIG. 35.

Here, a case when, in contrast to the first action shown in FIG. 34, a sequence of treatment is carried out by high-frequency energy treatment by the high-frequency electrodes 92, 94 without using the heaters 242, 252.

Like the first action, the action is the same until the body tissues L1, L2 are cut by the cutter 180 to form a cut surface S (S381 to S388). After the cutter 180 is returned to the original position thereof, treatment using high-frequency energy is carried out by the high-frequency electrodes 92, 94 (S389). Then, if the threshold Z1 and the impedance Z are the same or the impedance Z is larger than the threshold Z1 (S3810), the supply of energy from the high-frequency energy output portion 104 is stopped (S3811). Then, the end of a sequence of treatment is told by emitting a buzzer sound from the speaker 110 (S3812).

According to the present embodiment, as described above, the following effect is achieved.

Treatment of body tissues by high-frequency energy and treatment of body tissues by thermal energy can suitably be combined and thus, optimal treatment for the body tissues can be carried out.

Ninth Embodiment

Figure 36A:
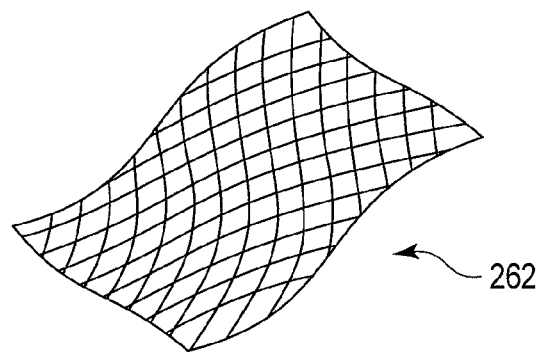
FIG. 36A is a rough perspective view showing a mesh-shaped coating member disposed between body tissues when the body tissues are treated to join by a medical treatment system according to a ninth embodiment.
Figure 36B:
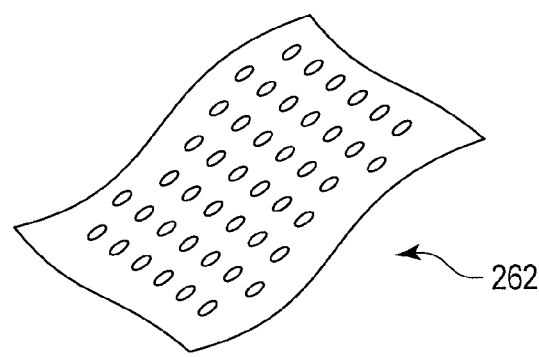
FIG. 36B is a rough perspective view showing a porous coating member disposed between body tissues when the body tissues are treated to join by the medical treatment system according to the ninth embodiment.
Figure 36C:
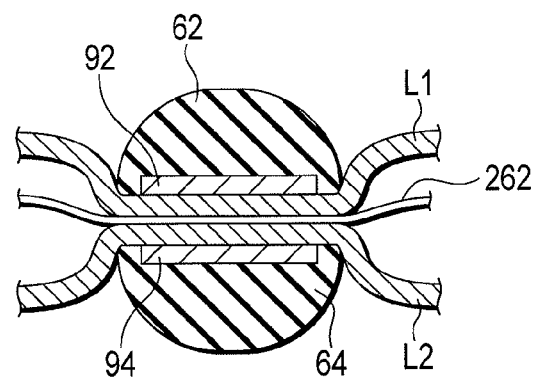
FIG. 36C is a rough transverse sectional view showing the state in which body tissues are treated to join by the medical treatment system while the body tissues to be joined are held by a treatment portion of an energy treatment device in a state in which the coating member is sandwiched between the body tissues to be joined according to the ninth embodiment.

Next, the ninth embodiment will be described using FIGS. 36A to 36C. The present embodiment is a modification of the seventh and eighth embodiments and the same reference numerals are attached to the same members as those described in the seventh and eighth embodiments or members achieving the same action as the action of those in the seventh and eighth embodiments and a detailed description thereof is omitted.

In the present embodiment, a case when a solid joined portion C is formed by thermal energy or high-frequency energy while a mesh-shaped (see FIG. 36A) or porous (see FIG. 36B) auxiliary joining member (join condition maintenance assistance portion) 262 including conjugation adjunct is sandwiched between contact surfaces C1, C2 of body tissues L1, L2 will be described.

As the auxiliary joining member 262, the same material as the material of coating members 224, 234 described in the seventh embodiment is suitably used and in such a case the material acts in the same manner as the coating members 224, 234.

The auxiliary joining member 262 is arranged between the body tissues L1, L2. The body tissues L1, L2 are held by first and second holding members 52, 54 of an energy treatment device 12. At this point, since the auxiliary joining member 262 is disposed between the body tissues L1, L2, the auxiliary joining member 262 is held between the body tissues L1, L2 by holding the body tissues L1, L2 by the first and second holding members 52, 54.

The auxiliary joining member 262 is formed in a mesh shape (FIG. 36A) or porous state (FIG. 36B) and thus, portions of contact surfaces C1, C2 of the body tissues L1, L2 are mutually in contact. Therefore, if a high-frequency current is passed between high-frequency electrodes 92, 94, the current is passed through the body tissues L1, L2 and the body tissues L1, L2 are thermogenic. The auxiliary joining member 262 melts due to heat generation of the body tissues L1, L2, leading to the same state as applying a fluid infiltration prevention substance to a body tissue $L_T$ to the entire contact surfaces C1, C2. Further, the substance that prevents fluid from penetrating the body tissue $L_T$ penetrates from the contact surfaces C1, C2 toward an exterior surface Sc in contact with the high-frequency electrodes 92, 94. Thus, the substance that prevents fluid from infiltrating the body tissue $L_T$ penetrates not only to the joint surface of the body tissues L1, L2, but also to tissues surrounding the joint surface. Therefore, the joined portion C of the body tissues L1, L2 can be formed not only in the contact surfaces C1, C2, but also in a wider area of the body tissues L1, L2. That is, the joined portion C here includes not only the joint surface, but also tissues therearound.

The high-frequency current is passed to the body tissues L1, L2 in this state until an impedance Z reaches a threshold Z1. After the impedance Z reaches the threshold Z1, the supply of energy is stopped. At this point, the joint surface of the joined portion C of the body tissues L1, L2 is joined by the substance that prevents moisture from penetrating the body tissue $L_T$ while collagens are joined by a treatment of the body tissues L1, L2 by high-frequency energy.

According to the present embodiment, as described above, the following effect is achieved.

By arranging the auxiliary joining member 262 between the body tissues L1, L2 to join the body tissues L1, L2, a large joining force can be obtained because, in addition to the joining force of the body tissues L1, L2 obtained when high-frequency energy is used, the contact surfaces C1, C2 can be joined by a substance like an adhesive. Moreover, since the substance like an adhesive is a fluid infiltration prevention material to the body tissue $L_T$, the substance like an adhesive can prevent fluid from infiltrating to the joint surface of the body tissues L1, L2 to be able to maintain a large joining force for a long time.

Tenth Embodiment

Next, the tenth embodiment will be described using FIGS. 37 to 41. The present embodiment is a modification of the first to ninth embodiments and the same reference numerals are attached to the same members as those described in the first to ninth embodiments or members achieving the same action as the action of those in the first to ninth embodiments and a detailed description thereof is omitted.

Figure 37A:
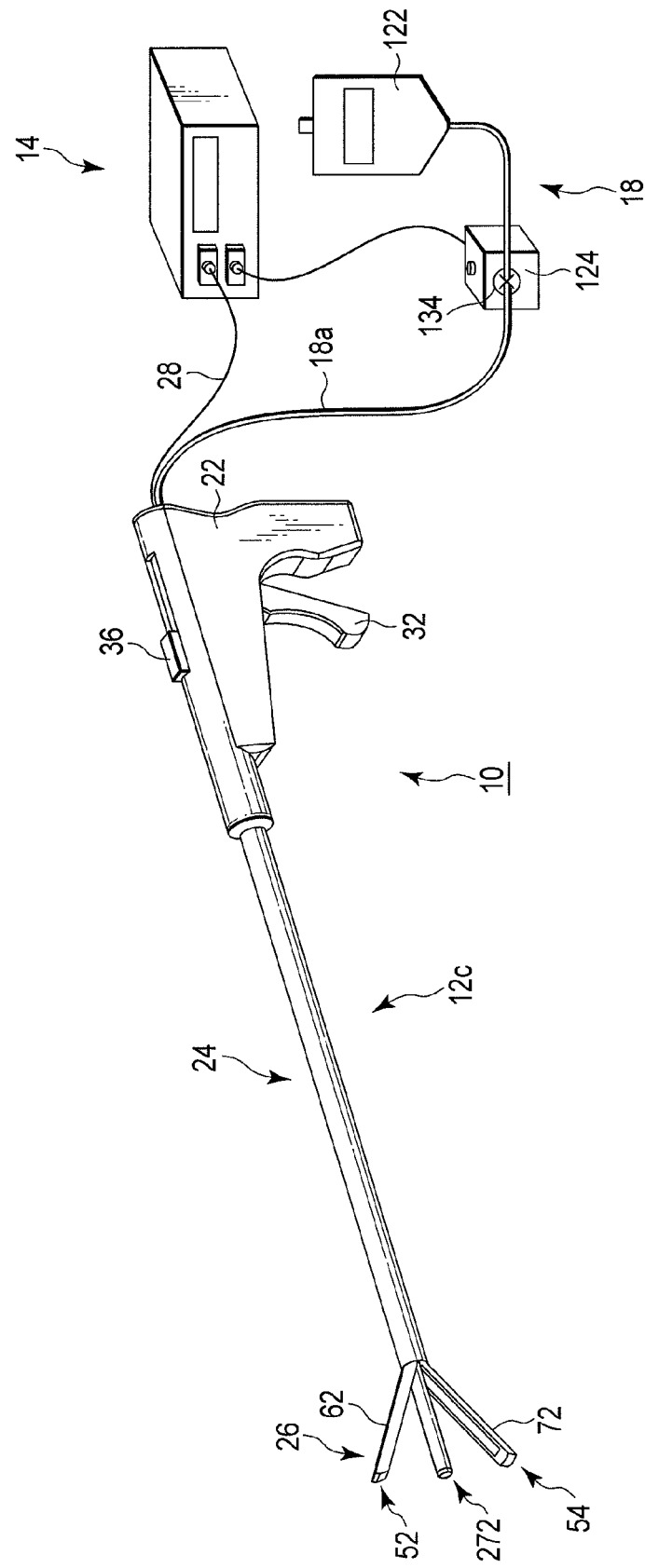
FIG. 37A is a schematic diagram showing a medical treatment system according to a tenth embodiment.
Figure 37B:
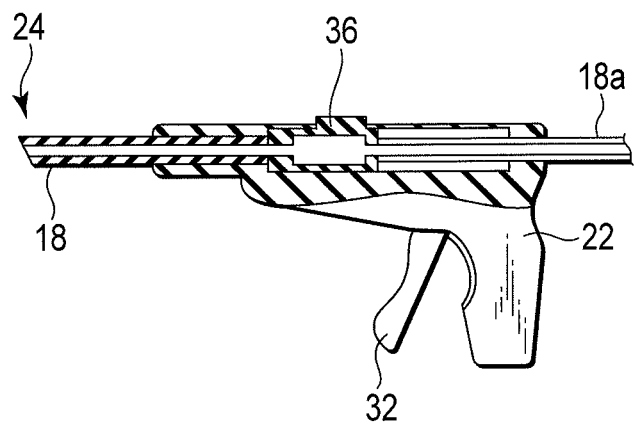
FIG. 37B is a rough partial longitudinal sectional view showing a handle of an energy treatment device of a medical treatment system according to the tenth embodiment.
Figure 38:
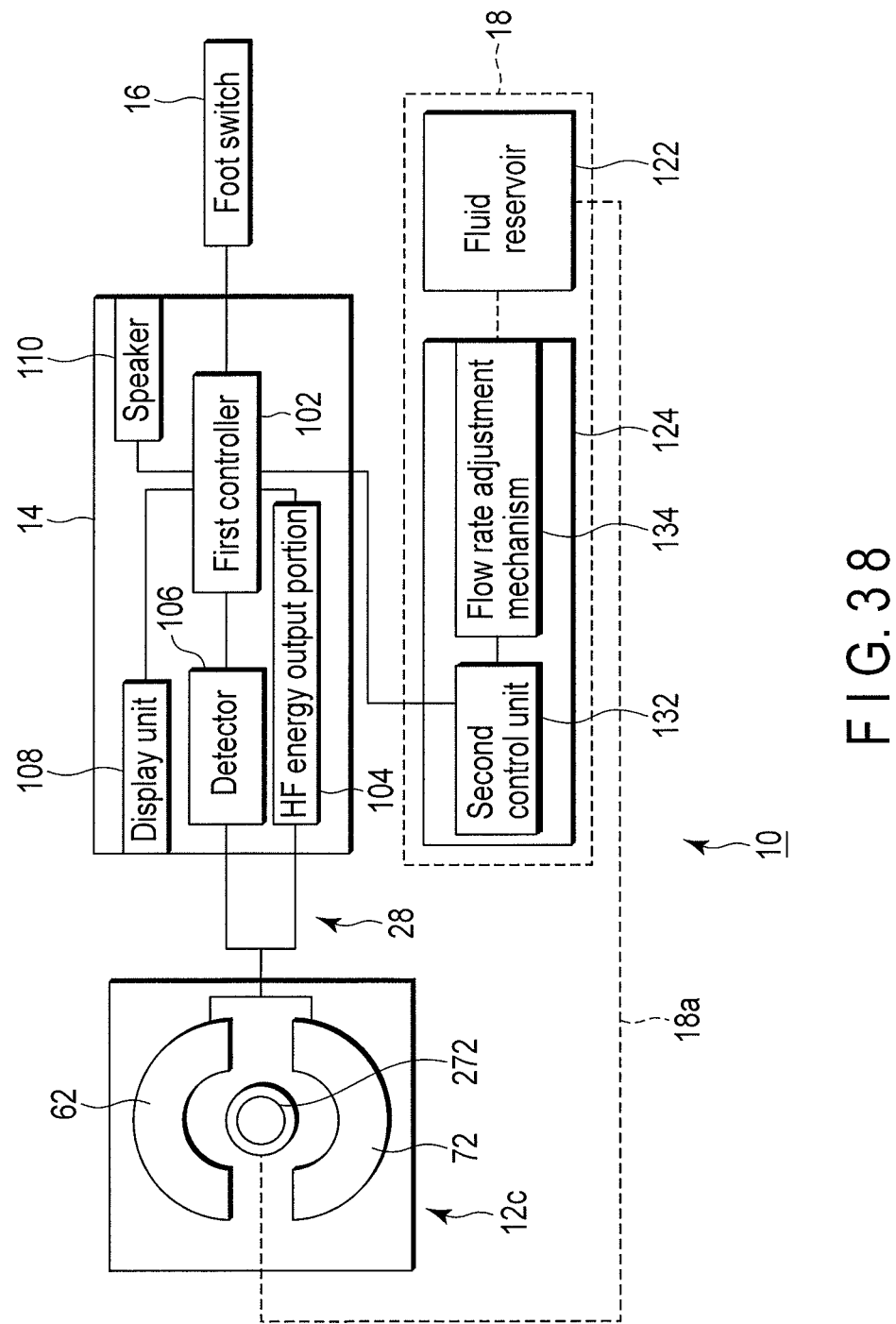
FIG. 38 is a rough block diagram showing the medical treatment system according to the tenth embodiment.
Figure 39A:
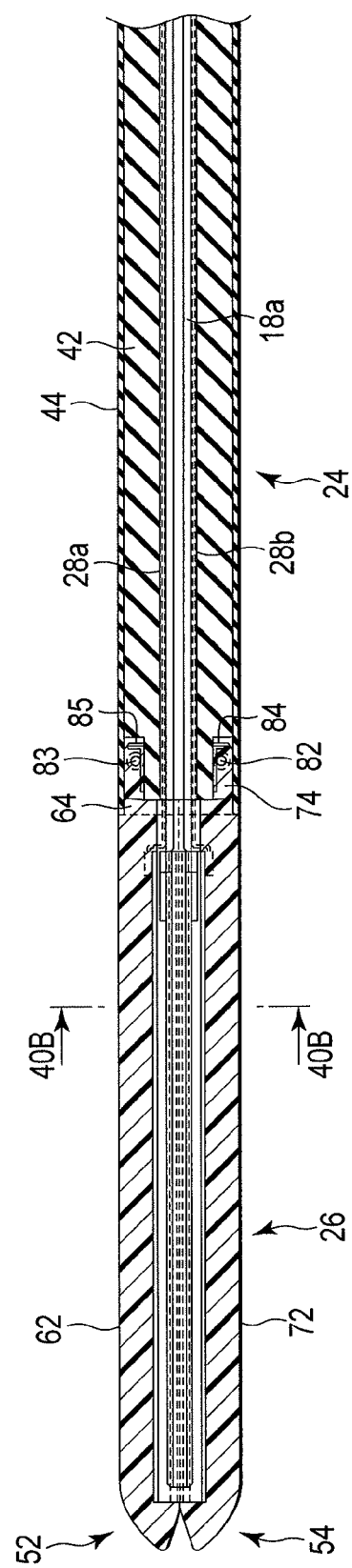
FIG. 39A is a rough longitudinal sectional view showing a closed treatment portion and a shaft of the energy treatment device of the bipolar type of the medical treatment system according to the tenth embodiment.

As shown in FIGS. 39A and 39B, a base 64 of a first holding member 52 is pivotally rotatably supported by a support pin 83 with respect to a pipe 42. The support pin 83 is disposed in parallel with a support pin 82 described in the first embodiment. The base 64 of the first holding member 52 is energized, like an elastic member 84 of a base 74 of a second holding member 54, by an elastic member 85 such as a plate spring. In the present embodiment, as shown in FIGS. 37A and 39B, both a first holding member 52 and a second holding member 54 of a treatment portion 26 of an energy treatment device 12c preferably open symmetrically with respect to the center axis of a shaft 24.

Figure 15B:
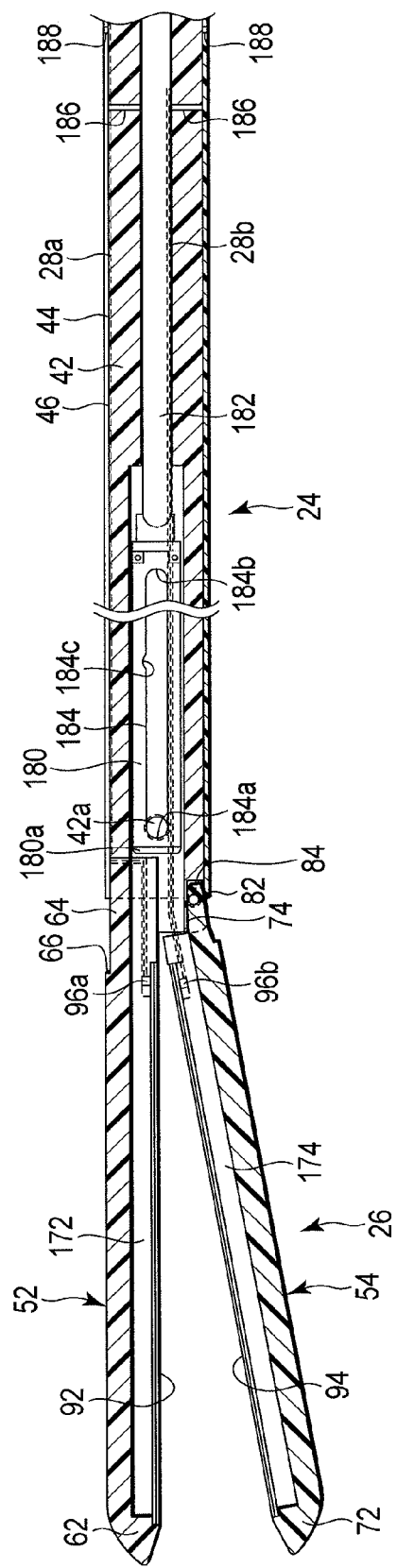
FIG. 15B is a rough longitudinal sectional view showing the open treatment portion and the shaft of the energy treatment device of the medical treatment system according to the third embodiment.

In the present embodiment, as shown in FIGS. 37A, 38, 39A, and 39B, a pipe-shaped member (join condition maintenance assistance portion) 272 is disposed as an auxiliary treatment device instead of a cutter 180 (see FIGS. 15A and 15B). The proximal end of the pipe-shaped member 272 is connected, as shown in FIGS. 39A and 39B, to a hose 18a.

As shown in FIG. 39B, a plurality of side holes 272a is formed on the side of a tip portion of the pipe-shaped member 272. The pipe-shaped member 272 can move between inside the shaft 24 and inside the treatment portion 26 by operating a pipe-shaped member movement knob 36 disposed on a handle 22 and can detect the position of the pipe-shaped member 272 relative to the treatment portion 26 or the shaft 24.

Figure 40B:
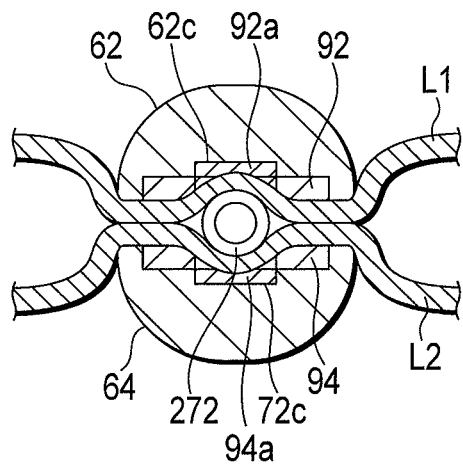
FIG. 40B is a rough transverse sectional view along a 40B-40B line in FIG. 39A showing the state in which body tissues are held by the treatment portion of the energy treatment device of the medical treatment system according to the tenth embodiment.
Figure 41:
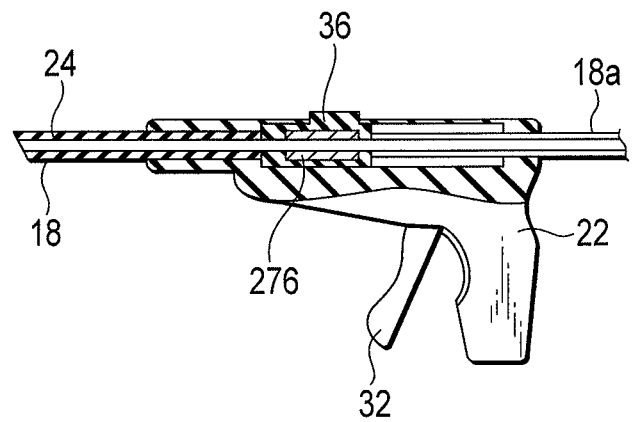
FIG. 41 is a rough partial longitudinal sectional view showing a modification of the handle of the energy treatment device of the medical treatment system according to the tenth embodiment.

As shown in FIGS. 40A and 40B, a main body 62 of a first holding member 52 has a recess (pipe-shaped member guiding groove) 62c forming a space to move the pipe-shaped member 272 forward and backward formed therein. The width of the recess 62c is preferably formed slightly larger than an outside diameter of the pipe-shaped member 272. A high-frequency electrode 92a is also disposed on the recess 62c. The high-frequency electrode 92a disposed on the recess 62c and a high-frequency electrode 92c disposed on an inner side of a holding surface 62a of the main body 62 are at the same potential.

Incidentally, a recess 72c is also formed, as shown in FIG. 40B, in a main body 72 of a second holding member 54 and a high-frequency electrode 94a at the same potential as a high-frequency electrode 94 is disposed on the recess 72c.

Next, the action of a medical treatment system 10 according to the present embodiment will be described.

As shown in FIG. 40B, the pipe-shaped member 272 of the energy treatment device 12c is arranged between body tissues L1, L2 to be joined. Then, the body tissues L1, L2 are held by the main bodies 62, 72 of the first and second holding members 52, 54 and the pipe-shaped member 272 is sandwiched between the body tissues L1, L2. At this point, the mesh-shaped or porous coating members 224, 234 (see FIGS. 28B and 28C) containing a conjugation adjunct, described in the seventh embodiment, are disposed outside the body tissues L1, L2 to be joined.

In this state, a substance (conjugation adjunct), such as an adhesive, that prevents fluid from infiltrating the body tissue $L_T$ is introduced from a fluid reservoir 122 to the pipe-shaped member 272 through a hose 18a. Thus, the substance that prevents fluid from infiltrating the body tissue $L_T$ is applied to the body tissues L1, L2 from the side holes 272a of the pipe-shaped member 272. In this state, the pipe-shaped member 272 is pulled out from between the main bodies 62, 72 of the first and second holding members 52, 54 by operating the pipe-shaped member movement knob 36. Thus, contact surfaces C1, C2 of the body tissues L1, L2 are in contact via the substance that prevents fluid from infiltrating the body tissue $L_T$.

Then, energy is supplied from a high-frequency energy output portion 104 to high-frequency electrodes 92, 94. Thus, the substance that prevents fluid from infiltrating the body tissue $L_T$ on the joint surface is heated and also the joint surfaces are joined. The mesh-shaped or porous coating members 224, 234 melt due to heat from the body tissues L1, L2 to coat the outer side of the body tissues L1, L2 to be joined.

As more energy is supplied to the high-frequency electrodes 92, 94 or the supply of energy is stopped, the substance that prevents fluid from penetrating the body tissue $L_T$ is hardened. At this point, the substance disposed on the joint surface of the body tissues L1, L2 to prevent fluid from penetrating the body tissue $L_T$ penetrates from the contact surfaces C1, C2 of the body tissues L1, L2 toward the high-frequency electrodes 92, 92a, 94, 94a. Thus, the substance that prevents moisture from penetrating the body tissue $L_T$ acts to maintain the joined state of the body tissues L1, L2.

According to the present embodiment, as described above, the following effect is achieved.

A fluid infiltration prevention substance to the body tissue $L_T$ can directly be applied to between the body tissues L1, L2. That is, the substance that reliably prevents fluid from penetrating the body tissue $L_T$ can be applied to between the contact surfaces C1, C2 of the body tissues L1, L2. Thus, when the body tissues L1, L2 are joined using high-frequency energy or the like, since the substance that prevents fluid from penetrating the body tissue $L_T$ is disposed between the contact surfaces C1, C2, even if a force to release joining of the body tissues L1, L2 acts, fluid can be prevented from penetrating the joint surface of the body tissues L1, L2 so that the joined state can be maintained.

Incidentally, a case when the coating members 224, 234 are used has been described in the present embodiment, but the coating members 224, 234 are not necessarily needed.

Also in the present embodiment, a case when the pipe-shaped member 272 is used, instead of the cutter 180, has been described, but an ultrasonic transducer 276 (see FIG. 41) may be disposed at the proximal end of the pipe-shaped member 272. That is, the pipe-shaped member 272 functions as an energy output portion that outputs ultrasonic energy to the body tissues L1, L2. In such a case, after pre-treatment to expose collagen to the contact surfaces C1, C2 of the body tissues L1, L2 by an ultrasonic device using the pipe-shaped member 272, the body tissues L1, L2 can be joined by the substance that prevents fluid from penetrating the body tissue $L_T$.

Eleventh Embodiment

Next, the eleventh embodiment will be described using FIGS. 42A to 42C. The present embodiment is a modification of the first to tenth embodiments. In the above embodiments, a case when treatment is carried out using high-frequency energy, thermal energy by heating of the heaters 242, 252, ultrasonic energy or the like has been described, but in the present embodiment, a first holding member 52 when treatment is carried out using thermal energy by laser light will be described.

Figure 42A:
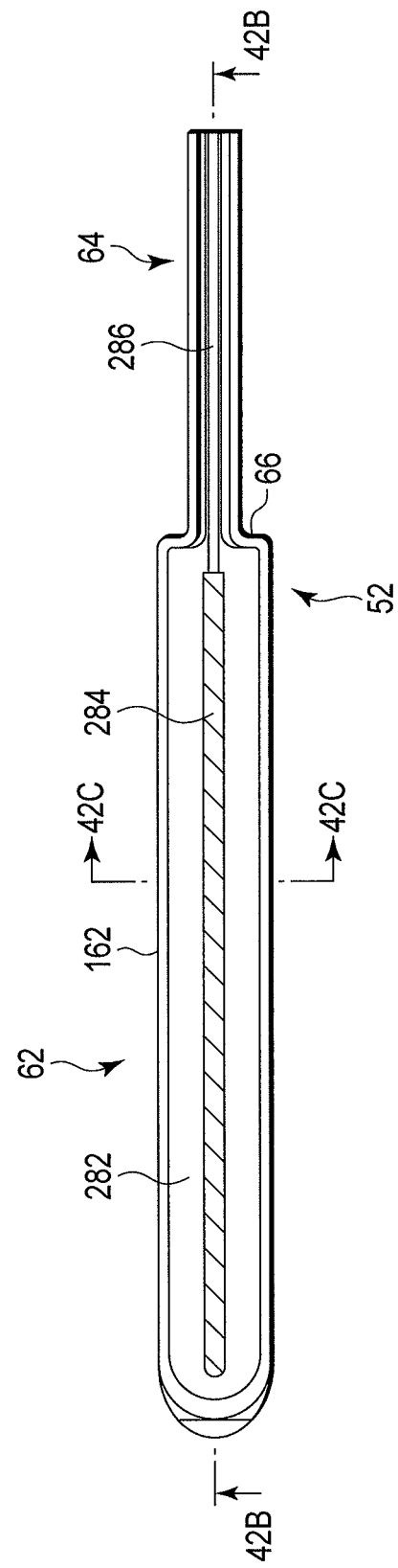
FIG. 42A is a rough plan view viewed from an arrow 42A direction in FIGS. 42B and 42C, and shows a first holding member of a treatment portion of an energy treatment device of a medical treatment system according to an eleventh embodiment.

As shown in FIGS. 42A to 42C, the first holding member 52 includes a heat exchanger plate (energy output portion) 282, instead of a high-frequency electrode 92, disposed therein. The heat exchanger plate 282 has a concave 282a formed therein. A diffuser 284 as an output member or an energy output portion is disposed in the concave 282a of the heat exchanger plate 282. A fiber (energy output portion) 286 is inserted into the diffuser 284. Thus, if laser light is incident to the fiber 286, the laser light is diffused to the outside from the diffuser 284. Energy of the laser light is converted into thermal energy by the heat exchanger plate 282 being irradiated therewith. Thus, the heat exchanger plate 282 can be used like the high-frequency electrode 92 (see FIGS. 31A and 31B) to which heat is conducted from the heater 242, as described in the eighth embodiment.

A fluid duct 162 shown in FIGS. 42A to 42C has an opening 162a (see FIGS. 11A to 11C) and thus, a substance that prevents fluid from penetrating a body tissue $L_T$ can be applied to the outer circumferential surface of the body tissue $L_T$.

Instead of the fluid duct 162, an edge (holding surface) 62a of a main body 62 of the first holding member 52 may be formed to carry out treatment using a coating member 224 (see FIG. 27A) described in the seventh embodiment. That is, treatment can be carried out in the same manner as in the above embodiments when laser light as energy is used.

By using the heat exchanger plate 282 as, for example, the high-frequency electrode 92, various kinds of treatment such as suitable treatment combining thermal energy and high-frequency energy, treatment using only thermal energy, and treatment using only high-frequency energy can be carried out.

Twelfth Embodiment

Next, the twelfth embodiment will be described using FIGS. 43 to 46B. The present embodiment is a modification of the first to eleventh embodiments. Here, a circular type bipolar energy treatment device (medical treatment device) 12d to carry out treatment, for example, through the abdominal wall or outside the abdominal wall is taken as an example of the energy treatment device.

Figure 43:
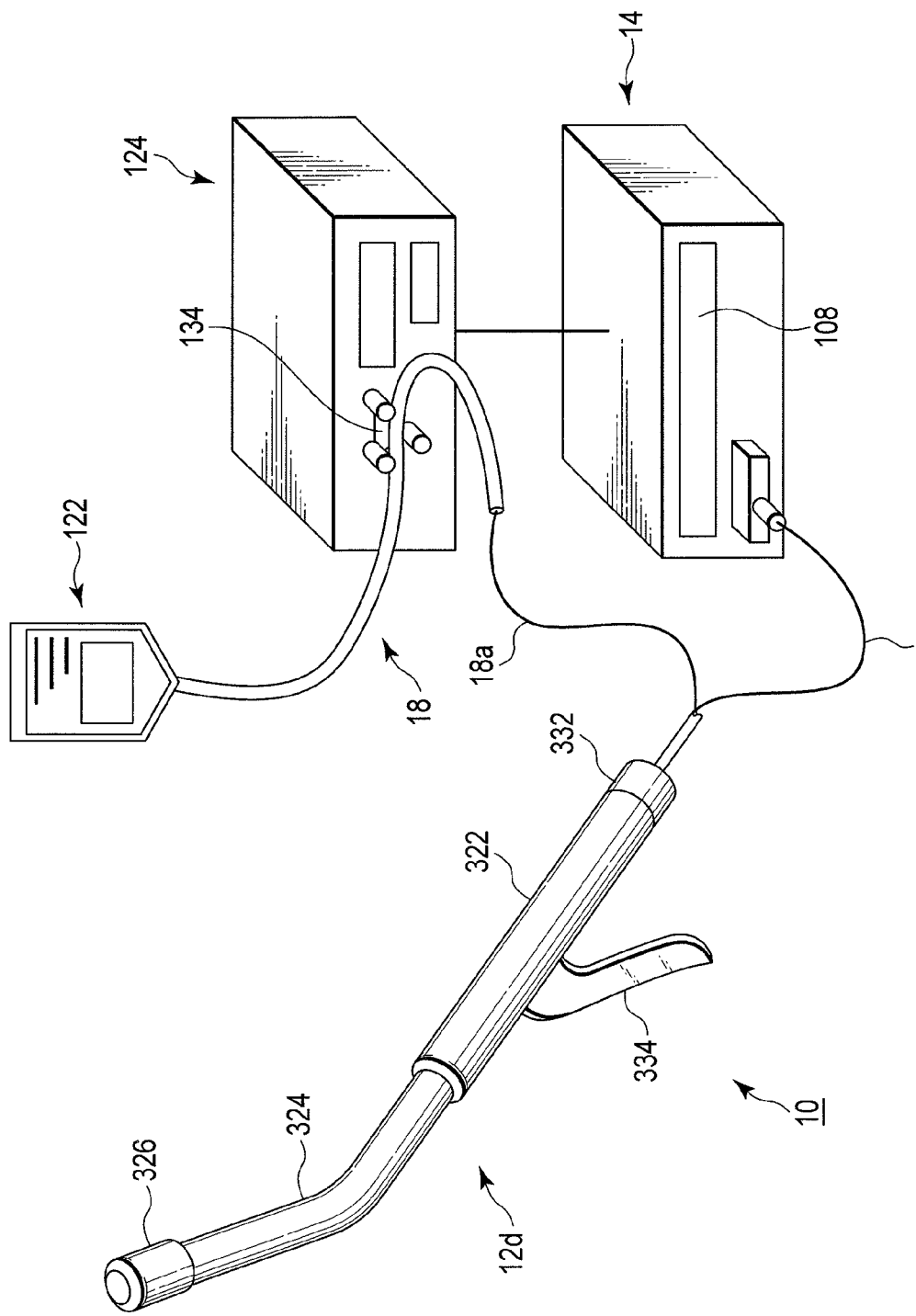
FIG. 43 is a schematic diagram showing a medical treatment system according to a twelfth embodiment.

As shown in FIG. 43, the energy treatment device 12d includes a handle 322, a shaft 324, and a treatment portion (holding portion) 326 that can be opened and closed. An energy source 14 is connected to the handle 322 via a cable 28 and also a fluid source 18 connected to the handle 322 via a hose 18a.

A treatment portion opening/closing knob 332 and a cutter driving lever 334 are disposed on the handle 322. The treatment portion opening/closing knob 332 is rotatable with respect to the handle 322. If the treatment portion opening/closing knob 332 is rotated, for example, clockwise with respect to the handle 322, a detachable-side holding member 354 described later of the treatment portion 326 is detached from a main body-side holding member 352 (see FIG. 46B) and if the treatment portion opening/closing knob 332 is rotated counterclockwise, the detachable-side holding member 354 is brought closer to the main body-side holding member 352 (see FIG. 46A).

The shaft 324 is formed in a cylindrical shape. In consideration of insertability into body tissues, the shaft 324 is made to be curved appropriately. It is, needless to say, that the shaft 324 is also suitably formed in a straight shape.

Figure 44A:
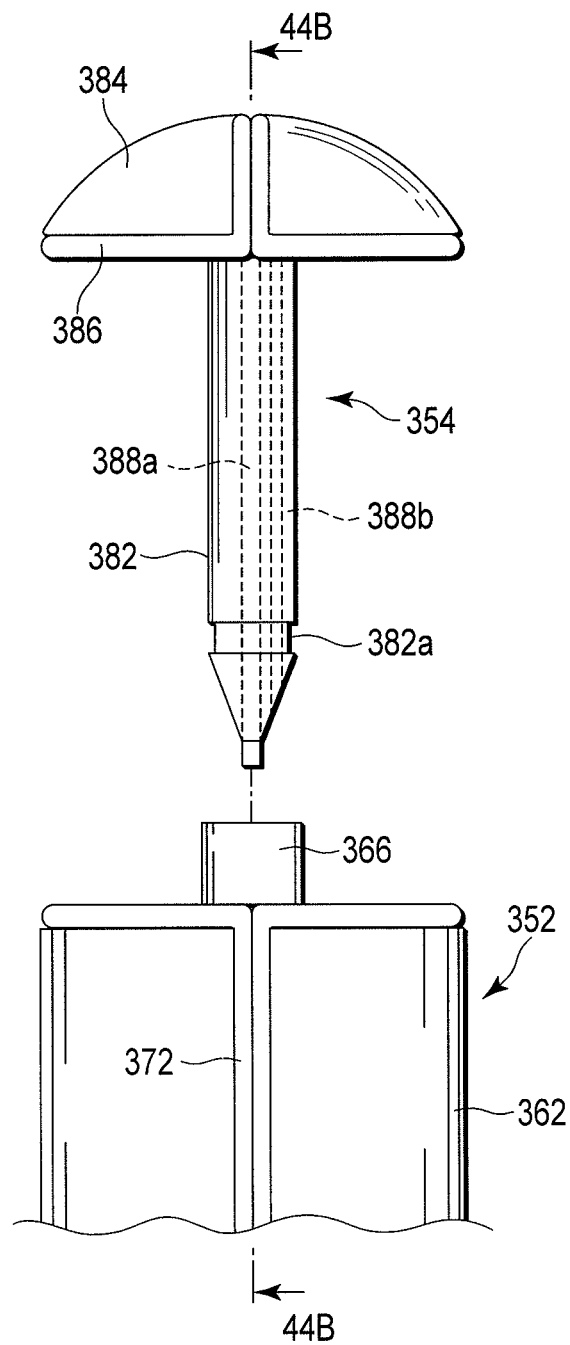
FIG. 44A is a rough front view showing the state in which a main body-side holding member and a detachable-side holding member of a treatment portion of a bipolar type energy treatment device of the medical treatment system are detached according to the twelfth embodiment.
Figure 44B:
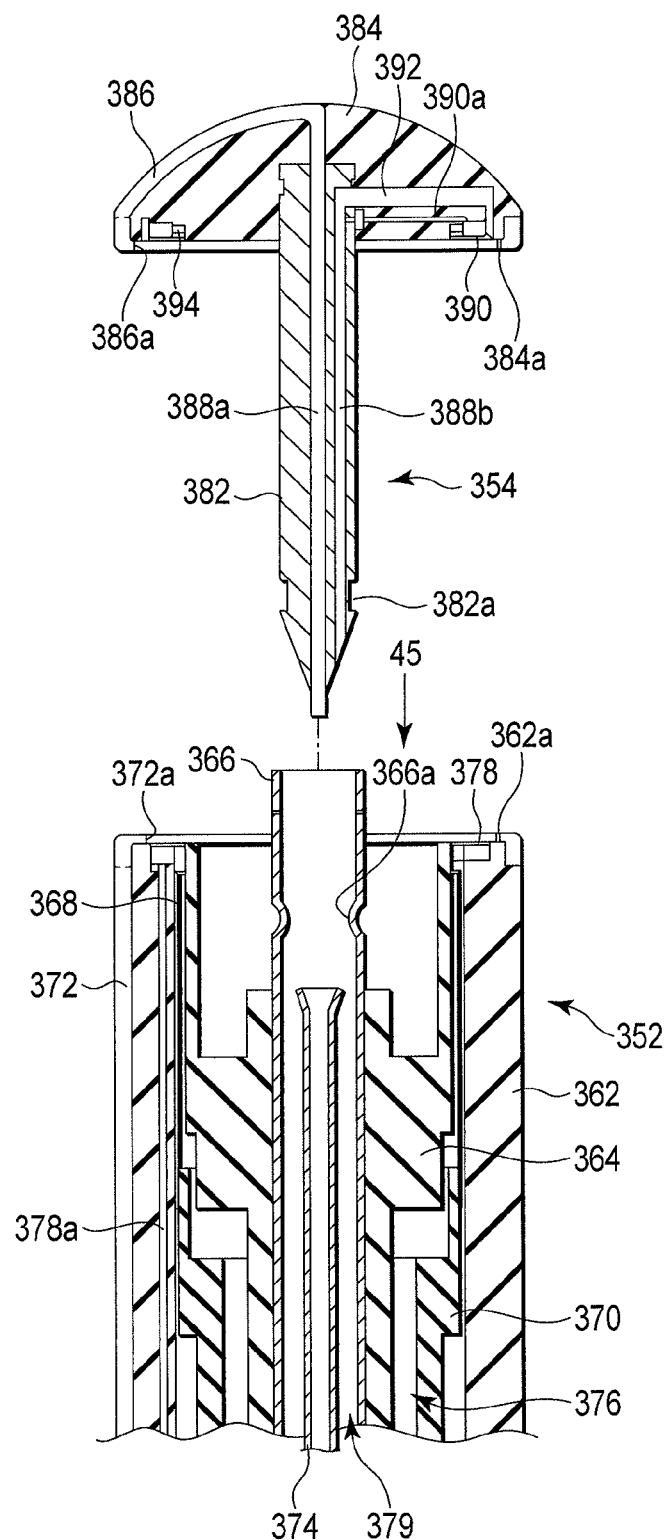
FIG. 44B is a rough longitudinal sectional view along a 44B-44B line in FIG. 44A, and shows the state in which the main body-side holding member and the detachable-side holding member of the treatment portion of the energy treatment device of the medical treatment system are detached according to the twelfth embodiment.

The treatment portion 326 is disposed at the distal end of the shaft 324. As shown in FIGS. 44A and 44B, the treatment portion 326 includes the main body-side holding member (first holding member) 352 formed at the distal end of the shaft 324 and the detachable-side holding member (second holding member) 354 detachable from the main body-side holding member 352.

The main body-side holding member 352 includes a cylinder body 362, a frame 364, an electrical connection pipe 366, a cutter 368, a cutter pusher 370, and first and second fluid ducts 372, 374. The cylinder body 362 and the frame 364 have insulating properties. The cylinder body 362 is coupled to the distal end of the shaft 324. The frame 364 is disposed in a state of being fixed with respect to the cylinder body 362.

Figure 46B:
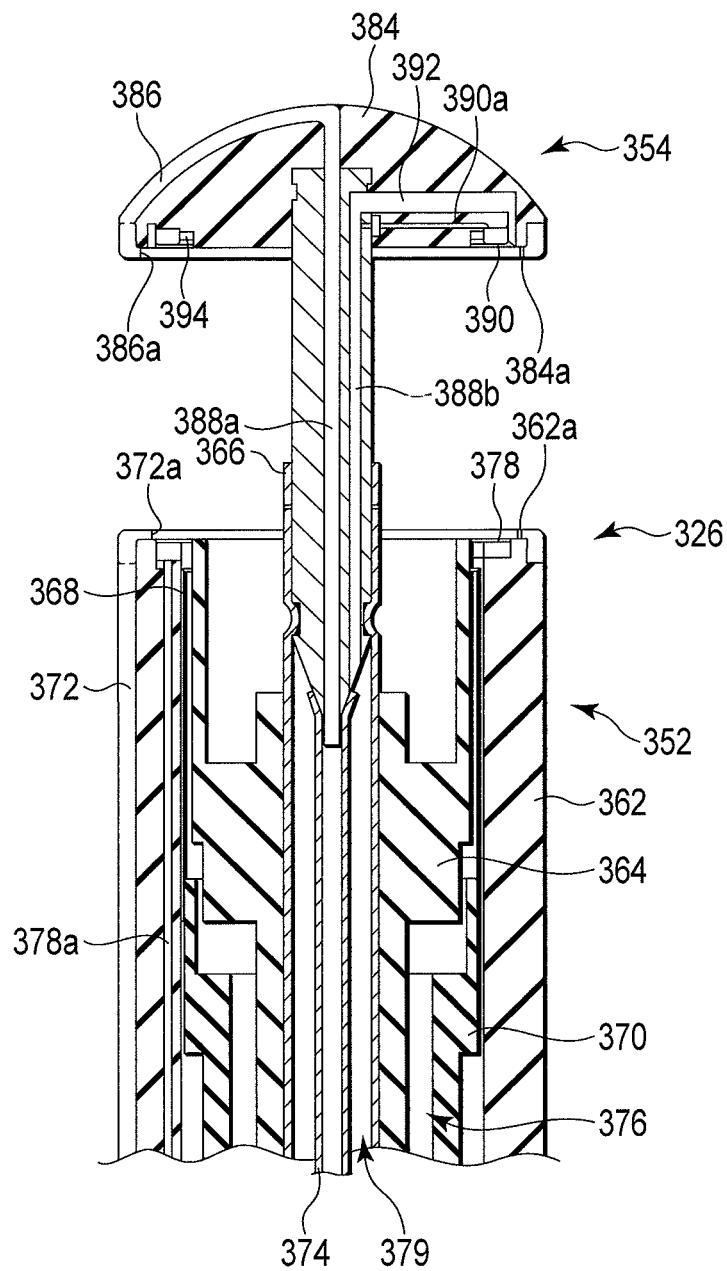
FIG. 46B is a rough longitudinal sectional view showing the state in which the main body-side holding member and the detachable-side holding member of the treatment portion of the bipolar type energy treatment device of the medical treatment system are open according to the twelfth embodiment.

The frame 364 has a center axis which is opened. The electrical connection pipe 366 is disposed in the opened center axis of the frame 364 movably within a predetermined range along the center axis of the frame 364. If the treatment portion opening/closing knob 332 of the handle 322 is rotated, as shown in FIGS. 46A and 46B, the electrical connection pipe 366 can move within the predetermined range through, for example, ball screw (not shown) action. The electrical connection pipe 366 has a projection 366a projecting inwards in a diameter direction formed thereon so that a connector 382a of an electrical connection shaft 382 described later can be engaged and released.

A second fluid duct 374 to pass a fluid to the detachable-side holding member 354 is disposed inside the electrical connection pipe 366. Like the electrical connection pipe 366, the second fluid duct 374 is movable within a predetermined range.

As shown in FIG. 44B, a space is formed between the cylinder body 362 and the frame 364. The cutter 368 in a cylindrical shape is disposed in the space between the cylinder body 362 and the frame 364. The proximal end of the cutter 368 is connected to the tip portion of the cutter pusher 368a disposed inside the shaft 324. The cutter 368 is fixed to the outer circumferential surface of the cutter pusher 370. Though not shown, the proximal end of the cutter pusher 370 is connected to the cutter driving lever 334 of the handle 322. Thus, if the cutter driving lever 334 of the handle 322 is operated, the cutter 368 moves via the cutter pusher 370.

A first fluid airway (fluid channel) 376 is formed between the cutter pusher 370 and the frame 364. Also, a fluid discharge port (not shown) which is configured to discharge a fluid passing through the first fluid airway 376 to the outside is formed in the shaft 324 or the handle 322.

As shown in FIGS. 44B and 45, a first high-frequency electrode 378 in an annular shape is formed as an output member or an energy discharge unit at the tip end of the cylinder body 362. The tip end of a first electrical connection line 378a is fixed to the first high-frequency electrode 378. The first electrical connection line 378a is connected to the cable 28 via the main body-side holding member 352, the shaft 324, and the handle 322.

An edge 362a of the cylinder body 362 is formed in a position higher than the first high-frequency electrode 378 on the outer side of the first high-frequency electrode 378. That is, the edge 362a of the main body-side holding member 352 is closer to a head portion 384 described later of the detachable-side holding member 354 than the first high-frequency electrode 378.

As shown in FIGS. 44A and 44B, the first fluid duct 372 is disposed on the outer circumferential surface of the cylinder body 362 of the main body-side holding member 352. The first fluid duct 372 is disposed on the outer side of the edge 362a of the cylinder body 362. Then, an opening (conjugation maintenance assistance portion) 372a is formed in a portion of the first fluid duct 372 disposed on the outer side of the edge 362a. The first fluid duct 372 is disposed along the outer circumferential surface of the shaft 324 from the outer circumferential surface of the cylinder body 362 of the main body-side holding member 352 and coupled to the hose 18a at the proximal end of the shaft 324 or in a portion of the handle 322.

The detachable-side holding member 354 includes the electrical connection shaft 382 having the connector 382a, the head portion 384, and a fluid duct 386. The head portion 384 is formed in a substantially semi-spherical shape. The connector 382a of the electrical connection shaft 382 is formed on the side closer to one end of the electrical connection shaft 382. The electrical connection shaft 382 has a circular transverse section, one end thereof is formed in a tapering shape, and the other end is fixed to the head portion 384. The connector 382a of the electrical connection shaft 382 is formed in a concave shape enabling engagement with the projection 366a of the electrical connection pipe 366 on the side closer to one end of the electrical connection shaft 382. The outer circumferential surface of a portion other than the connector 382a of the electrical connection shaft 382 is insulated by coating or the like.

The electrical connection shaft 382 has first and second ducts 388a, 388b formed so as to pass through one end and the other end thereof. The first duct 388a is formed to pass through the center axis of the electrical connection shaft 382. When the connector 382a of the electrical connection shaft 382 of the detachable-side holding member 354 is fitted to the projection 366a of the electrical connection pipe 366 of the main body-side holding member 352, the first duct 388a is communicatively connected to the second fluid duct 374 of the main body-side holding member 352. The second duct 388b is communicatively connected to a second fluid airway (fluid channel) 379 between the electrical connection pipe 366 and the second fluid duct 374.

The head portion 384 has an edge 384a formed thereon. A second high-frequency electrode 390 in an annular shape is disposed as an output member or an energy discharge unit on the inner side of the edge 384a. One end of a second electrical connection line 390a is fixed to the second high-frequency electrode 390. The other end of the second electrical connection line 390a is electrically connected to the electrical connection shaft 382.

A fluid discharge groove 392 in an annular shape is formed between the edge 384a of the head portion 384 and the second high-frequency electrode 390. The fluid discharge groove 392 is communicatively connected to the second duct 388b of the electrical connection shaft 382. Incidentally, the surface of the second high-frequency electrode 390 is in a state of being drawn to the edge 384a of the head portion 384. That is, the contact surface of the edge 384a of the detachable-side holding member 354 is closer to the main body-side holding member 352 than the second high-frequency electrode 390. Thus, a vapor or a liquid discharged from body tissues L1, L2 that have come into contact with the second high-frequency electrode 390 enters the fluid discharge groove 392.

A cutter receiving portion 394 to receive the cutter 368 disposed on the main body-side holding member 352 is formed inside the second high-frequency electrode 390 in an annular shape.

Further, the fluid discharge groove 392 is communicatively connected to the head portion 384 and the second duct 388b of the electrical connection shaft 382. The second duct 388b is communicatively connected to the second fluid airway (fluid channel) 379 of the electrical connection pipe 366. The shaft 324 or the handle 322 has a fluid discharge port (not shown) that discharges the fluid having passed through the second fluid airway 379 to the outside formed therein.

The electrical connection pipe 366 is connected to the cable 28 via the shaft 324 and the handle 322. Thus, when the connector 382a of the electrical connection shaft 382 of the detachable-side holding member 354 is engaged with the projection 366a of the electrical connection pipe 366, the second high-frequency electrode 390 and the electrical connection pipe 366 are electrically connected.

As shown in FIGS. 44A and 44B, the fluid duct 386 is disposed on the outer circumferential surface of the head portion 384 of the detachable-side holding member 354. The fluid duct 386 is disposed on the outer side of the edge 384a of the head portion 384. A portion of the fluid duct 386 disposed on the outer side of the edge 384a of the head portion 384 has an opening (conjugation maintenance assistance portion) 386a formed therein. The fluid duct 386 is communicatively connected to the first duct 388a inside the electrical connection shaft 382 from the outer circumferential surface of the head portion 384 of the detachable-side holding member 354. The first duct 388a of the electrical connection shaft 382 is connected to the second fluid duct 374 disposed inside the electrical connection pipe 366 of the main body-side holding member 352.

Next, the action of a medical treatment system 10 according to the present embodiment will be described.

As shown in FIG. 46A, the treatment portion 326 and the shaft 324 of the energy treatment device 12c are inserted into the abdominal cavity through, for example, the abdominal wall while the main body-side holding member 352 is closed with respect to the detachable-side holding member 354. The main body-side holding member 352 and the detachable-side holding member 354 of the energy treatment device 12c are opposed across body tissues to be treated.

The treatment portion opening/closing knob 332 of the handle 322 is operated to sandwich the body tissues L1, L2 to be treated between the main body-side holding member 352 and the detachable-side holding member 354. At this point, the treatment portion opening/closing knob 332 of the handle 322 is rotated, for example, clockwise with respect to the handle 322. Then, as shown in FIG. 46B, the electrical connection pipe 366 is moved to the side of the distal end portion thereof with respect to the frame 364 of the shaft 324 of the electrical connection pipe 366. Thus, the interval between the main body-side holding member 352 and the detachable-side holding member 354 increases so that the detachable-side holding member 354 can be separated from the main body-side holding member 352.

Then, the body tissues L1, L2 to be treated are arranged between the first high-frequency electrode 378 of the main body-side holding member 352 and the second high-frequency electrode 390 of the detachable-side holding member 354. The electrical connection shaft 382 of the detachable-side holding member 354 is inserted into the electrical connection pipe 366 of the main body-side holding member 352. In this state, the treatment portion opening/closing knob 332 of the handle 322 is rotated, for example, counterclockwise. Thus, the detachable-side holding member 354 is closed with respect to the main body-side holding member 352. In this manner, the body tissues L1, L2 to be treated are held between the main body-side holding member 352 and the detachable-side holding member 354.

In this state, the foot switch or hand switch is operated to supply energy from the energy source 14 to each of the first high-frequency electrode 378 and the second high-frequency electrode 390 via the cable 28. The first high-frequency electrode 378 passes a high-frequency current to the second high-frequency electrode 390 via the body tissues L1, L2. Thus, the body tissues L1, L2 between the first high-frequency electrode 378 and the second high-frequency electrode 390 are heated.

At this point, a fluid such as a vapor and a liquid arises from a heated portion of the body tissues L1, L2. The surface of the first high-frequency electrode 378 exposed to the side of the detachable-side holding member 354 is positioned slightly lower than the edge 362a of the main body-side holding member 352 while the first high-frequency electrode 378 is fixed to the main body-side holding member 352. Similarly, the surface of the second high-frequency electrode 390 exposed to the side of the main body-side holding member 352 is positioned slightly lower than the edge 384a of the head portion 384 of the detachable-side holding member 354 while the second high-frequency electrode 390 is fixed to the detachable-side holding member 354.

Thus, the edge 362a of the main body-side holding member 352 discharges a fluid arising from the body tissue L1 in contact with the first high-frequency electrode 378 to the second fluid airway 379 inside the electrical connection pipe 366 through the fluid discharge groove 392 and the second duct 388b. Also, the edge 384a of the detachable-side holding member 354 discharges a fluid arising from the body tissue L2 in contact with the second high-frequency electrode 390 to the first fluid airway 376 between the cylinder body 362 and the frame 364. Therefore, the edge 362a of the main body-side holding member 352 and the edge 384a of the detachable-side holding member 354 each serve the role as a barrier portion (dam) to prevent a fluid arising from the body tissues L1, L2 from leaking to the outside of the main body-side holding member 352 and the detachable-side holding member 354.

Then, while the main body-side holding member 352 and the detachable-side holding member 354 are closed, a fluid arising from the body tissue L1 flows into the first fluid airway 376 and a fluid arising from the body tissue L2 flows into the second fluid airway 379 by the edge 362a of the main body-side holding member 352 and the edge 384a of the detachable-side holding member 354 being kept in contact. Thus, a fluid arising from the body tissues L1, L2 is passed from the first and second fluid airways 376, 379 to the side of the handle 322 before being discharged to the outside of the energy treatment device 12d.

After the body tissues L1, L2 are joined, an adhesive is passed from each of the openings 372a, 386a of the first and second fluid ducts 372, 386. Then, the adhesive containing a conjugation adjunct is applied to the outer circumferential surface of the treated body tissues L1, L2. Thus, the outer circumferential surface of the body tissues $L_T$ coated with the adhesive.

According to the present embodiment, as described above, the following effect is achieved.

Close contact of contact surfaces C1, C2 of the body tissues L1, L2 can be made more reliable by treating the body tissues L1, L2 for conjugation while an impedance Z of the body tissues L1, L2 is measured. After the body tissues L1, L2 are treated for conjugation, moisture can be prevented from infiltrating into a joined portion C of a body tissue $L_T$ treated for conjugation by coating the outer circumference of the body tissue $L_T$ treated for conjugation with an adhesive or the like. Therefore, a state in which the contact surfaces C1, C2 of the body tissues L1, L2 are closely in contact (state in which the body tissue $L_T$ is joined) can be maintained for a long time.

Thirteenth Embodiment

Next, the thirteenth embodiment will be described using FIGS. 47A and 47B. The present embodiment is a modification of the twelfth embodiment and the same reference numerals are attached to the same members as those described in the twelfth embodiment or members achieving the same action as the action of those in the twelfth embodiment and a detailed description thereof is omitted.

Figure 47A:
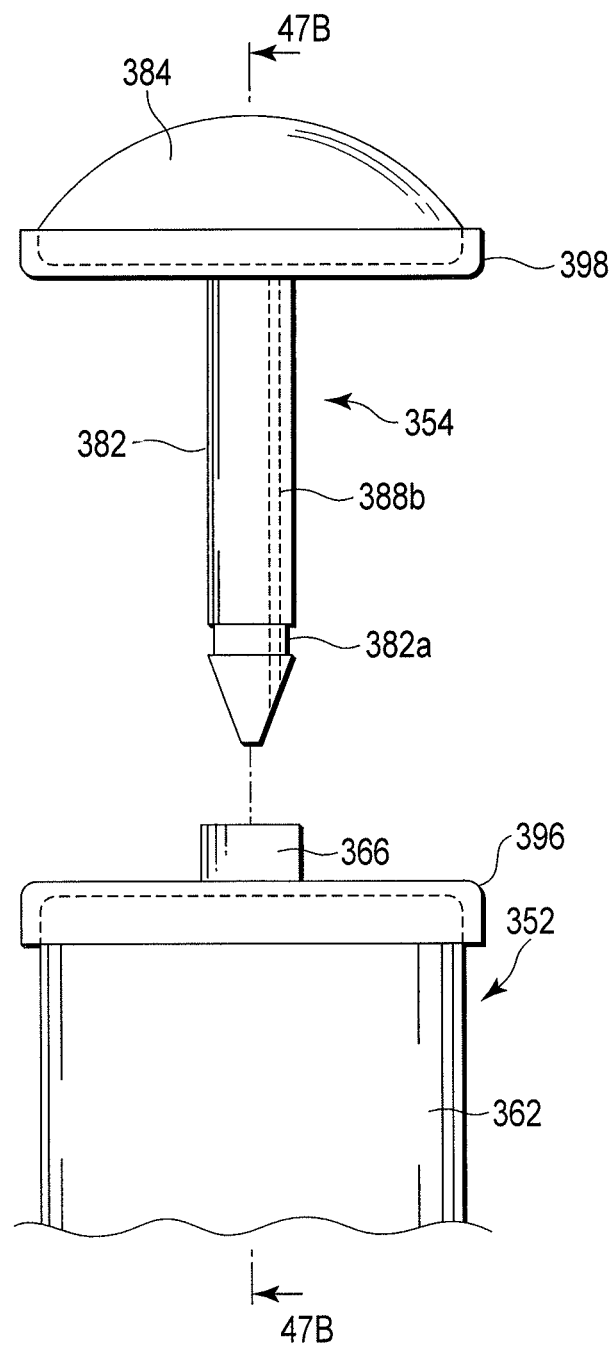
FIG. 47A is a rough front view showing the state in which a main body-side holding member and a detachable-side holding member of a treatment portion of a bipolar type energy treatment device of a medical treatment system are detached according to a thirteenth embodiment.
Figure 47B:
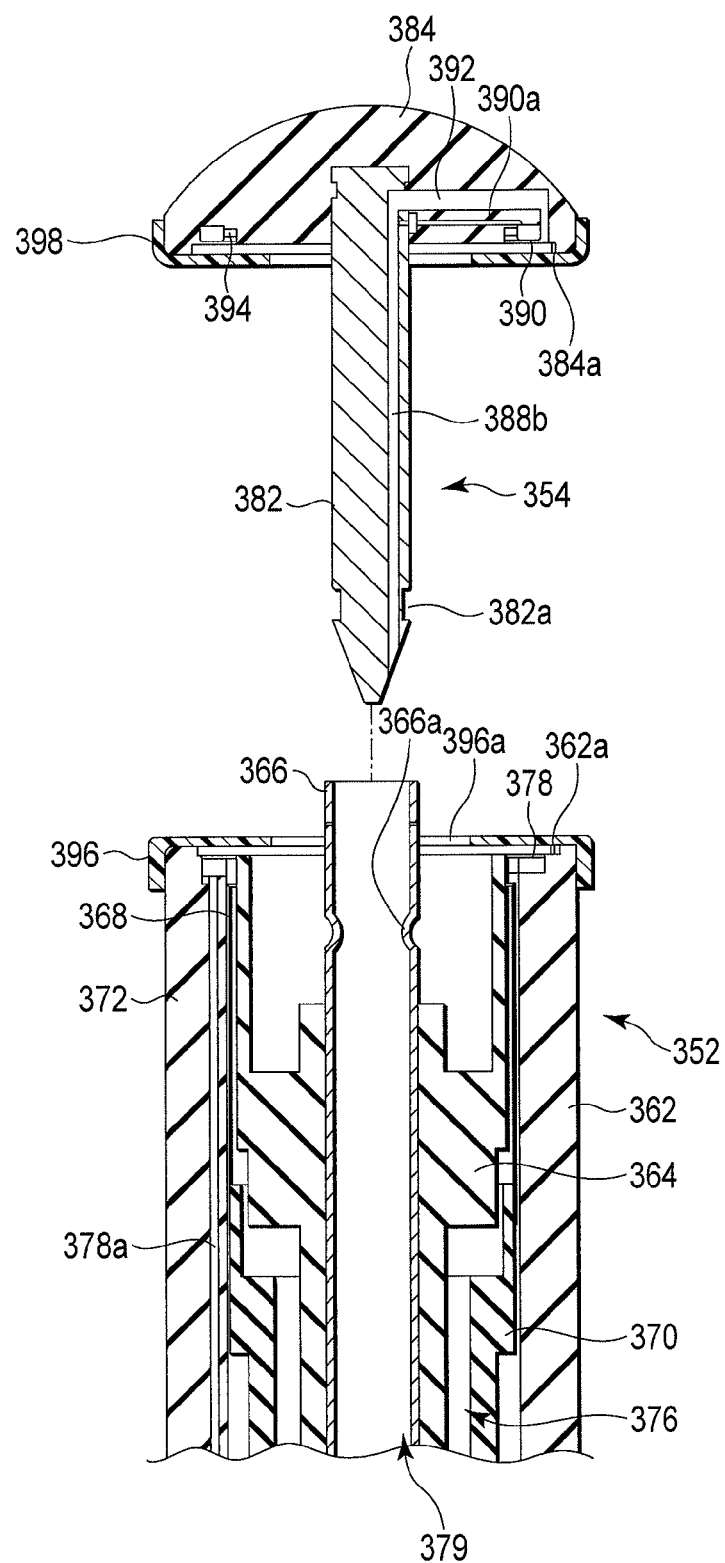
FIG. 47B is a rough longitudinal sectional view along a 47B-47B line in FIG. 47A, and shows the state in which the main body-side holding member and the detachable-side holding member of the treatment portion of the energy treatment device of the medical treatment system are detached according to the thirteenth embodiment.

As shown in FIGS. 47A and 47B, a main body-side holding member 352 and a detachable-side holding member 354 have coating members (join condition maintenance assistance portions) 396, 398 in various sheet shapes such as a nonporous shape, porous shape, and mesh shape containing a conjugation adjunct, instead fluid ducts 372, 386 (see FIGS. 44A and 44B) described in the twelfth embodiment, disposed therein. The coating members 396, 398 are formed from components similar to those of coating members 224, 234 described in the seventh embodiment.

The coating members 396, 398 are each formed in a substantially annular shape. That is, the coating members 396, 398 have openings 396a, 398a therewithin. The opening 396a of the coating member 396 disposed on the main body-side holding member 352 causes an electrical connection pipe 366 of the main body-side holding member 352 to project. The opening 398a of the coating member 398 disposed on the detachable-side holding member 354 causes an electrical connection shaft 382 of the detachable-side holding member 354 to project.

By carrying out treatment in this state, the outer circumference of the body tissues L1, L2 can be coated so that fluid can be prevented from infiltrating the body tissues L1, L2.

In the present embodiment, a case when high-frequency electrodes 378, 390 are used has been described, but it is also preferable to use other type of energy such as a heater and laser light.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical treatment apparatus to treat and join body tissues, comprising:
    a first holding member having a holding surface;
    a second holding member having a holding surface opposed to the holding surface of the first holding member and configured to form a contact surface for the body tissues to be treated;
    an energy output portion which is provided on the first holding member and which is configured to supply energy to the body tissues and join the body tissues;
    a fluid source which is provided outside of the first holding member and the second holding member and which is configured to discharge a fluid infiltration prevention substance, wherein said substance helps prevent infiltration of body fluid from the body tissues; and
    a fluid conduit having insulating properties and a plurality of openings, the fluid conduit surrounding the energy output portion on the holding surface of the first holding member, which is configured to hold the body tissues together with the holding surface of the second holding member and which receives the substance, wherein the fluid conduit projects from a surface of the energy output portion to form a barrier, and the fluid infiltration prevention substance flows through the openings.

2. The medical treatment apparatus according to claim 1, wherein the fluid infiltration prevention substance comprises bioabsorbable materials.

3. The medical treatment apparatus according to claim 1, further comprising a cutter configured to cut the body tissues to be treated.

4. The medical treatment apparatus according to claim 1, wherein: the fluid conduit is a pipe including the openings, and
    the pipe is configured to contact the body tissues directly and apply the fluid infiltration prevention substance through the openings.

5. The medical treatment apparatus according to claim 1, wherein:
    the fluid infiltration prevention substance contains a compound and
    the compound is the substance which is configured to coat the body tissues by a physical action, a chemical action, or both actions and which is configured to assist in maintaining the body tissues joined.

6. The medical treatment apparatus according to claim 5, wherein the compound is at least one of protein, glucide, polymer, and hardener.

7. The medical treatment apparatus according to claim 1, wherein the energy output portion is configured to output heat to the body tissues by at least one of high frequency energy, microwave, heat, laser, and ultrasonic vibration.

8. A medical treatment system comprising:
   the medical treatment apparatus according to claim 1;
   an energy source connected to the medical treatment apparatus to supply energy to body tissues;
   a detector which is configured to detect at least one of a temperature, impedance and a phase of the body tissues to be treated; and
   a controller which is configured to control an output that controls the energy output portion based on information provided by the detector.

9. The medical treatment apparatus according to claim 1, wherein
   the medical treatment apparatus includes a hose connected to the fluid source, the hose passing the fluid infiltration prevention substance from the fluid source to the fluid conduit.

10. The medical treatment apparatus according to claim 1, wherein the openings are configured to be directed toward the energy output portion.

11. The medical treatment apparatus according to claim 10, wherein the openings are configured to be directed toward a center axis which extends from a distal portion of the energy output portion to a proximal portion of the energy output portion.

12. The medical treatment apparatus according to claim 1, wherein the fluid conduit projects from an outer surface of the energy output portion.

* * * * *